(12) United States Patent
Yamazaki

(10) Patent No.: US 10,085,629 B2
(45) Date of Patent: Oct. 2, 2018

(54) OBSERVATION SYSTEM

(71) Applicant: OLYMPUS CORPORATION, Tokyo (JP)

(72) Inventor: Kenji Yamazaki, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/586,423

(22) Filed: May 4, 2017

(65) Prior Publication Data

US 2017/0231480 A1    Aug. 17, 2017

Related U.S. Application Data

(63) Continuation of application No. PCT/JP2015/078643, filed on Oct. 8, 2015.

(30) Foreign Application Priority Data

Mar. 25, 2015  (JP) ................. 2015-062812

(51) Int. Cl.
*A61B 1/06* (2006.01)
*A61B 1/00* (2006.01)
(Continued)

(52) U.S. Cl.
CPC .......... *A61B 1/0684* (2013.01); *A61B 1/0002* (2013.01); *A61B 1/00006* (2013.01);
(Continued)

(58) Field of Classification Search
CPC ....... A61B 1/0684; A61B 1/06; A61B 1/0638; A61B 1/00006; A61B 1/0002;
(Continued)

(56) References Cited

U.S. PATENT DOCUMENTS

2003/0229270 A1* 12/2003 Suzuki ................ A61B 1/043
600/178
2012/0147166 A1    6/2012 Minetoma et al.
(Continued)

FOREIGN PATENT DOCUMENTS

EP     2462860 A1    6/2012
EP     2481342 A1    8/2012
(Continued)

OTHER PUBLICATIONS

International Search Report dated Dec. 28, 2015 issued in PCT/JP2015/078643.

*Primary Examiner* — Peter Luong
(74) *Attorney, Agent, or Firm* — Scully, Scott, Murphy & Presser, P.C.

(57) ABSTRACT

An observation system includes: a light source portion configured to generate light of a first wavelength band, and light of a second wavelength band; an emphasizing processing portion configured to perform processing for highlighting a structure positioned in a layer of a predetermined depth in the biological tissue, to an image obtained by picking up an image of return light from the biological tissue; a selecting portion configured to change an emphasis amount; and a control portion configured to increase a ratio of a light quantity of the light of the second wavelength band to the light quantity of the light of the first wavelength band when the emphasis amount is increased, or decrease the ratio of the light quantity of the light of the second wavelength band to the light quantity of the light of the first wavelength band when the emphasis amount is decreased.

6 Claims, 26 Drawing Sheets

(51) Int. Cl.
*A61B 1/05* (2006.01)
*A61B 5/02* (2006.01)
*A61B 5/00* (2006.01)
*A61B 1/04* (2006.01)
*A61B 5/145* (2006.01)
*A61B 5/024* (2006.01)
*A61B 5/026* (2006.01)

(52) U.S. Cl.
CPC .............. *A61B 1/043* (2013.01); *A61B 1/051* (2013.01); *A61B 1/06* (2013.01); *A61B 1/0638* (2013.01); *A61B 5/0059* (2013.01); *A61B 5/02028* (2013.01); *A61B 5/0261* (2013.01); *A61B 5/02416* (2013.01); *A61B 5/145* (2013.01)

(58) Field of Classification Search
CPC ..... A61B 1/051; A61B 1/043; A61B 5/02028; A61B 5/0059; A61B 5/02416; A61B 5/0261; A61B 5/145
See application file for complete search history.

(56) References Cited

U.S. PATENT DOCUMENTS

| | | | |
|---|---|---|---|
| 2012/0154565 A1* | 6/2012 | Kaku | ................. A61B 1/00009 348/68 |
| 2012/0197077 A1 | 8/2012 | Kaku | |

FOREIGN PATENT DOCUMENTS

| | | |
|---|---|---|
| EP | 2666403 A1 | 11/2013 |
| JP | 2012-125289 A | 7/2012 |
| JP | 2012-152414 A | 8/2012 |
| JP | 2013-202167 A | 10/2013 |
| JP | 2013-244041 A | 12/2013 |

* cited by examiner

OBSERVATION SYSTEM

CROSS REFERENCE TO RELATED APPLICATION

This application is a continuation application of PCT/JP2015/078643 filed on Oct. 8, 2015 and claims benefit of Japanese Application No. 2015-062812 filed in Japan on Mar. 25, 2015, the entire contents of which are incorporated herein by this reference.

BACKGROUND OF THE INVENTION

1. Field of the Invention

The present invention relates to an observation system, and in particular to an observation system used for observing biological tissue.

2. Description of the Related Art

In endoscope observation, a technique for generating and displaying an observation image in which a mucosal structure and/or a structure of a blood vessel or the like included in biological tissue is emphasized by irradiating the biological tissue with illumination light having a predetermined center wavelength set according to an extinction coefficient with respect to blood is conventionally known.

Specifically, for example, Japanese Patent Application Laid-Open Publication No. 2013-202167 discloses a configuration of generating and displaying an observation image in which surface blood vessels and middle-deep blood vessels of biological tissue are emphasized by irradiating the biological tissue with white light formed of narrowband light, a center wavelength of which is 445 nm, and fluorescence originated from a fluorescent material excited by the narrowband light of 445 nm and narrowband light, the center wavelength of which is 405 nm, as illumination light, when a blood vessel emphasizing observation mode is set in an endoscope system. In addition, Japanese Patent Application Laid-Open Publication No. 2013-202167 discloses that contour emphasizing processing is executed to an image signal including a lot of information on the middle-deep blood vessels when generating the observation image.

SUMMARY OF THE INVENTION

An observation system of one aspect of the present invention includes: a light source portion configured to generate light of a first wavelength band scattered or absorbed in a layer of a predetermined depth in biological tissue, and light of a second wavelength band scattered or absorbed in the layer of the predetermined depth in the biological tissue and having a higher extinction coefficient with respect to blood than the extinction coefficient with respect to blood of the first wavelength band, as illumination light for illuminating the biological tissue; an emphasizing processing portion configured to perform emphasizing processing for highlighting a structure positioned in the layer of the predetermined depth in the biological tissue, to an image obtained by picking up an image of return light from the biological tissue illuminated by the illumination light; a selecting portion configured to change an emphasis amount of the emphasizing processing performed in the emphasizing processing portion; and a control portion configured to increase a ratio of a light quantity of the light of the second wavelength band to the light quantity of the light of the first wavelength band when the emphasis amount is increased by the selecting portion, or decrease the ratio of the light quantity of the light of the second wavelength band to the light quantity of the light of the first wavelength band when the emphasis amount is decreased by the selecting portion.

DETAILED DESCRIPTION OF THE PREFERRED EMBODIMENT(S)

Hereinafter, embodiments of the present invention will be described with reference to the drawings.
(First Embodiment)

FIG. 1 to FIG. 25 relate to the first embodiment of the present invention.

Figure 1:
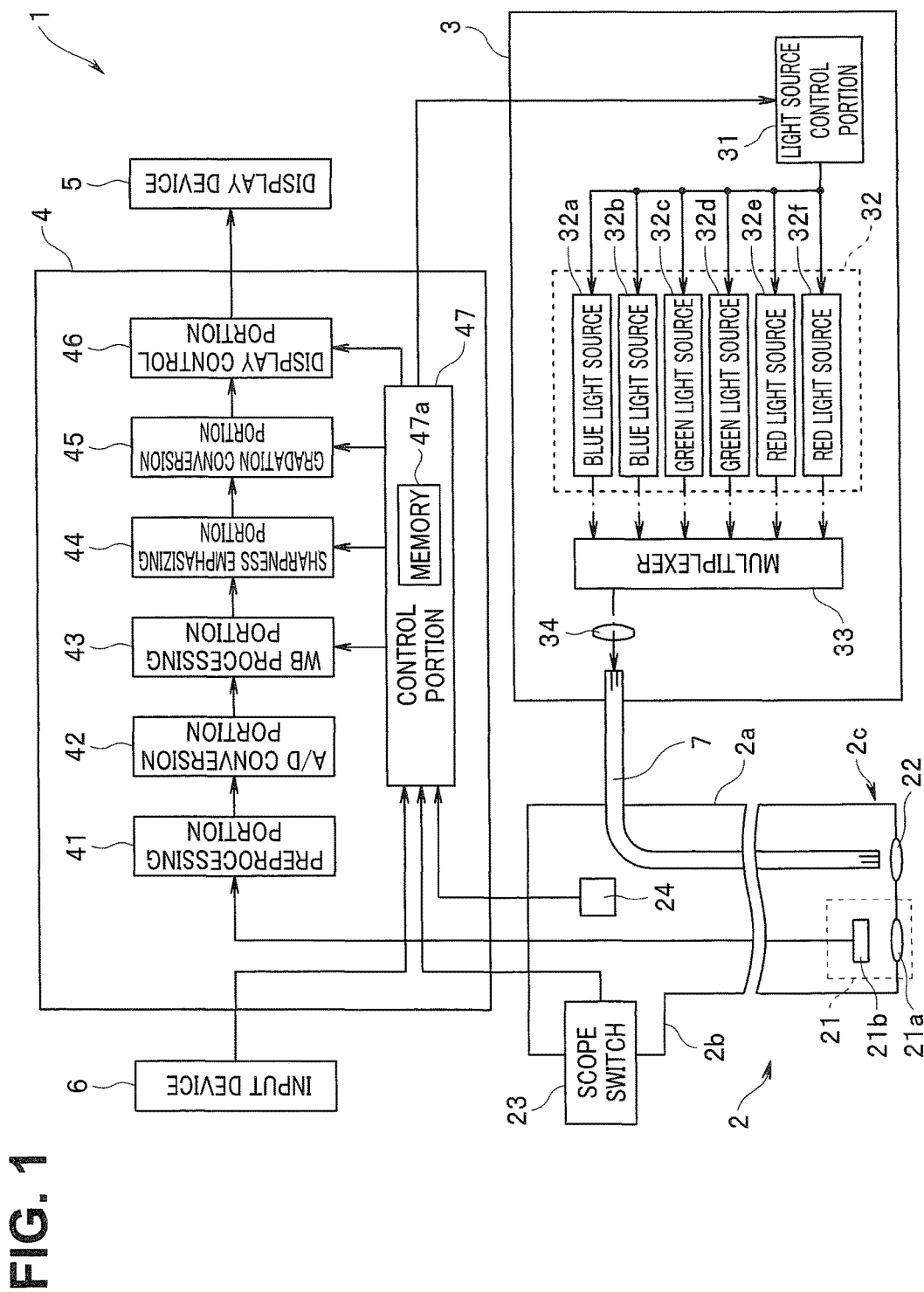
FIG. 1 is a diagram illustrating a configuration of a main part of an observation system relating to a first embodiment.

An observation system 1 includes, as illustrated in FIG. 1, an endoscope 2 insertable into a subject and configured to pick up an image of an object such as biological tissue inside the subject and output an image pickup signal, a light source device 3 configured to supply illumination light used for observing the object through a light guide 7 inserted and arranged inside the endoscope 2, a processor 4 configured to generate and output a video signal or the like according to the image pickup signal outputted from the endoscope 2, a display device 5 configured to display an observation image or the like according to the video signal outputted from the processor 4, and an input device 6 provided with a switch and/or a button or the like capable of giving an instruction or the like according to an input operation by a user such as an operator to the processor 4. FIG. 1 is a diagram illustrating a configuration of a main part of the observation system relating to the first embodiment.

The endoscope 2 includes an insertion portion 2a formed in an elongated shape insertable into the subject, and an operation portion 2b provided on a proximal end side of the insertion portion 2a. In addition, the endoscope 2 is configured to be attachably and detachably connected to the processor 4, through a universal cable (not shown in the figure) incorporating a signal line used for transmitting various signals such as the image pickup signal outputted from an image pickup portion 21, for example. Furthermore, the endoscope 2 is configured to be attachably and detachably connected to the light source device 3 through a light guide cable (not shown in the figure) incorporating at least a portion of the light guide 7.

On a distal end portion 2c of the insertion portion 2a, the image pickup portion 21 for picking up an image of the object such as the biological tissue inside the subject, an emission end portion of the light guide 7, and an illumination optical system 22 configured to irradiate the object with the illumination light transmitted by the light guide 7 are provided.

The image pickup portion 21 is configured to pick up an image of return light from the object illuminated by the illumination light emitted through the illumination optical system 22 and output the image pickup signal. Specifically, the image pickup portion 21 includes an objective optical system 21a configured to form the image of the return light emitted from the object, and an image pickup device 21b configured by disposing a plurality of pixels for receiving the return light and picking up the image in a matrix shape in accordance with an image forming position of the objective optical system 21a.

The image pickup device 21b includes an image sensor such as a CCD or a CMOS for example, and is configured to generate the image pickup signal by picking up the image of the return light formed by the objective optical system 21a and output the generated image pickup signal to the processor 4.

The operation portion 2b is configured having a shape that can be gripped and operated by the user. In addition, the operation portion 2b is provided with a scope switch 23 configured including one or more switches with which the processor 4 can be instructed according to an input operation of the user.

Furthermore, inside the operation portion 2b, a scope memory 24 storing endoscope information including information indicating an ID number intrinsic to the endoscope 2 or the like is provided. Note that the endoscope information stored in the scope memory 24 is read by a control portion 47 (to be described later) of the processor 4, when the endoscope 2 and the processor 4 are electrically connected and a power source of the processor 4 is turned on.

The light source device 3 is configured including a light source control portion 31, a light source unit 32, a multiplexer 33, and a converging lens 34.

The light source control portion 31 is configured including a drive circuit for driving respective light sources of the light source unit 32, for example. In addition, the light source control portion 31 is configured to generate and output a light source drive signal for driving the respective light sources of the light source unit 32 according to an illumination control signal and an emission light quantity ratio control signal outputted from the processor 4.

The light source unit 32 is configured including blue light sources 32a and 32b, green light sources 32c and 32d, and red light sources 32e and 32f.

The respective light sources of the light source unit 32 are configured to individually emit or quench the light at timing according to the light source drive signal outputted from the light source control portion 31. In addition, the respective light sources of the light source unit 32 are configured to emit the light by an emission light quantity according to the light source drive signal outputted from the light source control portion 31.

The blue light source 32a is provided with a blue LED for example, and is configured to emit BS light which is blue light, a center wavelength of which is set between 400 nm and 440 nm. Specifically, the blue light source 32a is configured to emit the BS light, the center wavelength of which is set at 415 nm, for example. That is, the BS light has a characteristic that the BS light is scattered and/or reflected in a surface layer of the biological tissue and an extinction coefficient with respect to blood becomes high compared to BL light to be described later. Note that the emission light quantity of the blue light source 32a is assumed to be stipulated as a total light quantity obtained by integrating intensity of the light of respective wavelengths included in a wavelength band of the BS light.

The blue light source 32b is provided with the blue LED for example, and is configured to emit the BL light which is the blue light, the center wavelength of which is set between 450 nm and 490 nm. Specifically, the blue light source 32b is configured to emit the BL light, the center wavelength of which is set at 475 nm, for example. That is, the BL light has the characteristic that the BL light is scattered and/or reflected in the surface layer of the biological tissue and the extinction coefficient with respect to blood becomes low compared to the BS light. Note that the emission light quantity of the blue light source 32b is assumed to be stipulated as the total light quantity obtained by integrating the intensity of the light of the respective wavelengths included in the wavelength band of the BL light.

The green light source 32c is provided with a green LED for example, and is configured to emit GS light which is green light, the center wavelength of which is set between 500 nm and 530 nm. Specifically, the green light source 32c is configured to emit the GS light, the center wavelength of which is set at 520 nm, for example. That is, the GS light has the characteristic that the GS light is scattered and/or reflected in a middle layer more on a surface layer side than a deep layer of the biological tissue and the extinction coefficient with respect to blood becomes low compared to GL light to be described later. Note that the emission light quantity of the green light source 32c is assumed to be stipulated as the total light quantity obtained by integrating the intensity of the light of the respective wavelengths included in the wavelength band of the GS light.

The green light source 32d is provided with the green LED for example, and is configured to emit the GL light which is the green light, the center wavelength of which is set between 540 nm and 580 nm. Specifically, the green light source 32d is configured to emit the GL light, the center wavelength of which is set at 540 nm, for example. That is, the GL light has the characteristic that the GL light is scattered and/or reflected in the middle layer more on the surface layer side than the deep layer of the biological tissue and the extinction coefficient with respect to blood becomes high compared to the GS light. Note that the emission light quantity of the green light source 32d is assumed to be stipulated as the total light quantity obtained by integrating the intensity of the light of the respective wavelengths included in the wavelength band of the GL light.

The red light source 32e is provided with a red LED for example, and is configured to emit RS light which is red light, the center wavelength of which is set between 590 nm and 610 nm. Specifically, the red light source 32e is configured to emit the RS light, the center wavelength of which is set at 600 nm, for example. That is, the RS light has the characteristic that the RS light is scattered and/or reflected in the deep layer of the biological tissue and the extinction coefficient with respect to blood becomes high compared to RL light to be described later. Note that the emission light quantity of the red light source 32e is assumed to be stipulated as the total light quantity obtained by integrating the intensity of the light of the respective wavelengths included in the wavelength band of the RS light.

The red light source 32f is provided with the red LED for example, and is configured to emit the RL light which is the red light, the center wavelength of which is set between 620 nm and 700 nm. Specifically, the red light source 32f is configured to emit the RL light, the center wavelength of which is set at 630 nm, for example. That is, the RL light has the characteristic that the RL light is scattered and/or reflected in the deep layer of the biological tissue and the extinction coefficient with respect to blood becomes low compared to the RS light. Note that the emission light quantity of the red light source 32f is assumed to be stipulated as the total light quantity obtained by integrating the intensity of the light of the respective wavelengths included in the wavelength band of the RL light.

The multiplexer 33 is configured to multiplex the light emitted from the light source unit 32 and emit the light to the converging lens 34.

The converging lens 34 is configured to converge the light emitted through the multiplexer 33 and makes the light be incident on an incident end portion of the light guide 7.

The processor 4 is configured including a preprocessing portion 41, an A/D conversion portion 42, a white balance processing portion (abbreviated as a WB processing portion, hereinafter) 43, a sharpness emphasizing portion 44, a gradation conversion portion 45, a display control portion 46, and the control portion 47.

The preprocessing portion 41 is configured including a signal processing circuit, for example. In addition, the preprocessing portion 41 is configured to execute predetermined signal processing such as amplification and noise elimination to the image pickup signal outputted from the image pickup portion 21 of the endoscope 2, and output the image pickup signal to the A/D conversion portion 42.

The A/D conversion portion 42 is configured including an A/D conversion circuit, for example. In addition, the A/D conversion portion 42 is configured to generate image data by executing processing such as A/D conversion to the image pickup signal outputted from the preprocessing portion 41, and output the generated image data to the WB processing portion 43.

The WB processing portion 43 is configured including a white balance processing circuit, for example. In addition, the WB processing portion 43 is configured to execute white balance processing to the image data outputted from the A/D conversion portion 42 according to control of the control portion 47, and output the image data to which the white balance processing is executed to the sharpness emphasizing portion 44.

The sharpness emphasizing portion 44 is configured including a sharpness emphasizing processing circuit, for example. In addition, the sharpness emphasizing portion 44 is configured to execute spatial filter processing corresponding to emphasizing processing for highlighting one or more structures included in the biological tissue to the image data outputted from the WB processing portion 43 according to the control of the control portion 47, and output the image data to which the spatial filter processing is executed to the gradation conversion portion 45. In other words, the sharpness emphasizing portion 44 executes sharpness emphasizing processing for emphatically displaying sharpness of one or more structures included in the biological tissue to the image data outputted from the WB processing portion 43 according to the control of the control portion 47, and output the image data to which the sharpness emphasizing processing is executed to the gradation conversion portion 45.

The gradation conversion portion 45 is configured including a gradation conversion circuit, for example. In addition, the gradation conversion portion 45 is configured to execute gradation conversion processing corresponding to the emphasizing processing for highlighting one or more structures included in the biological tissue to the image data outputted from the sharpness emphasizing portion 44 according to the control of the control portion 47, and output the image data to which the gradation conversion processing is executed to the display control portion 46. In other words, the gradation conversion portion 45 executes contrast emphasizing processing for emphatically displaying contrast of one or more structures included in the biological tissue to the image data outputted from the sharpness emphasizing portion 44 according to the control of the control portion 47, and output the image data to which the contrast emphasizing processing is executed to the display control portion 46.

The display control portion 46 is configured including a display control circuit, for example. In addition, the display control portion 46 is configured to generate the video signal by allocating the image data outputted from the gradation conversion portion 45 to an R channel, a G channel and a B channel of the display device 5 according to the control of the control portion 47, and output the generated video signal to the display device 5.

The control portion 47 includes a control circuit configured by an FPGA or a CPU, for example. In addition, the control portion 47 is provided with a memory 47a storing information on a plurality of spatial filters available for the spatial filter processing by the sharpness emphasizing portion 44 and a plurality of gradation conversion functions available for the gradation conversion processing by the gradation conversion portion 45 or the like beforehand. Furthermore, the control portion 47 is configured to read the endoscope information stored in the scope memory 24 when the endoscope 2 and the processor 4 are electrically connected and the power source of the processor 4 is turned on.

The control portion 47 is configured to generate the illumination control signal for illuminating an object by a predetermined illumination pattern such as a time-division illumination pattern and output the signal to the light source control portion 31. In addition, the control portion 47 is configured to generate the emission light quantity ratio control signal for setting a light quantity ratio of the emission light quantities of the respective light sources of the light source unit 32 according to desired sharpness selected in a sharpness emphasizing switch (not shown in the figure) provided in the input device 6 and/or the scope switch 23, and output the signal to the light source control portion 31.

The control portion 47 is configured to perform control for causing the white balance processing using a predetermined white balance coefficient to be performed to the WB processing portion 43. Note that the predetermined white balance coefficient is assumed to be stored beforehand in the memory 47a as a value used for causing the image data obtained by picking up an image of a white reference object to be displayed (visually recognized) at the display device 5 as a white observation image.

The control portion 47 is configured to read the spatial filter according to the desired sharpness selected in the sharpness emphasizing switch provided in the input device 6 and/or the scope switch 23 from the memory 47a, and perform control for causing the spatial filter processing using the read spatial filter to be performed to the sharpness emphasizing portion 44.

The control portion 47 is configured to read the gradation conversion function according to desired contrast selected in a contrast emphasizing switch (not shown in the figure) provided in the input device 6 and/or the scope switch 23 from the memory 47a, and perform control for causing the gradation conversion processing using the read gradation conversion function to be performed to the gradation conversion portion 45.

The control portion 47 is configured to perform control for causing each image data outputted from the gradation conversion portion 45 to be allocated to a color channel according to the return light emitted from the object illuminated by the predetermined illumination pattern to the display control portion 46.

Subsequently, specific operations or the like of the observation system 1 relating to the present embodiment will be described below. Note that, hereinafter, unless mentioned otherwise, a case that the sharpness of one of four of "off", "weak", "middle" and "strong" can be selected as the desired sharpness (emphasis degree) in the sharpness emphasizing switch will be described as an example. In addition, hereinafter, unless mentioned otherwise, the case that the contrast of one of two of "normal" and "high" can be selected as the desired contrast (emphasis degree) in the contrast emphasizing switch will be described as an example.

First, a user connects respective portions of the observation system 1, supplies power, then performs an operation of switching an illumination switch (not shown in the figure) provided in the scope switch 23 and/or the input device 6 from off to on, for example, and thus gives an instruction for causing the illumination light to be supplied from the light source device 3 to the endoscope 2 to the control portion 47. In addition, the user gives an instruction for not highlighting the structure included in the biological tissue by performing the operation of selecting the sharpness "off" in the sharpness emphasizing switch provided in the scope switch 23 and/or the input device 6, for example, to the control portion 47.

When detecting that the power source of the processor 4 is turned on and the illumination switch is turned on, the control portion 47 generates the illumination control signal for illuminating the object by a time division illumination pattern IP1, and outputs the signal to the light source control portion 31. Specifically, when detecting that the power source of the processor 4 is turned on and the illumination switch is turned on, the control portion 47 generates the illumination control signal for illuminating the object by the illumination pattern IP1 of cyclically repeating an illumination period PA of making the blue light sources 32a and 32b simultaneously emit the light, an illumination period PB of making the green light sources 32c and 32d simultaneously emit the light and an illumination period PC of making the red light sources 32e and 32f simultaneously emit the light in the order for example, and outputs the signal to the light source control portion 31. Note that the order of the respective illumination periods in the illumination pattern IP1 may not be the order of PA→PB→PC.

In addition, when detecting that the sharpness "off" is selected in the sharpness emphasizing switch, the control portion 47 generates the emission light quantity ratio control signal for setting the emission light quantities of the respective light sources of the light source unit 32 to a mutually same emission light quantity EA for example, and outputs the signal to the light source control portion 31.

The light source control portion 31 generates and outputs the light source drive signal for making the blue light sources 32a and 32b simultaneously emit the light while making the green light sources 32c and 32d and the red light sources 32e and 32f quench the light in the illumination period PA, making the green light sources 32c and 32d simultaneously emit the light while making the blue light sources 32a and 32b and the red light sources 32e and 32f quench the light in the illumination period PB, and making the red light sources 32e and 32f simultaneously emit the light while making the blue light sources 32a and 32b and the green light sources 32c and 32d quench the light in the illumination period PC, according to the illumination control signal outputted from the control portion 47.

In addition, the light source control portion 31 generates and outputs the light source drive signal for making the respective light sources of the light source unit 32 emit the light by the emission light quantity EA when the sharpness "off" is selected in the sharpness emphasizing switch, according to the emission light quantity ratio control signal outputted from the control portion 47.

Figure 2:
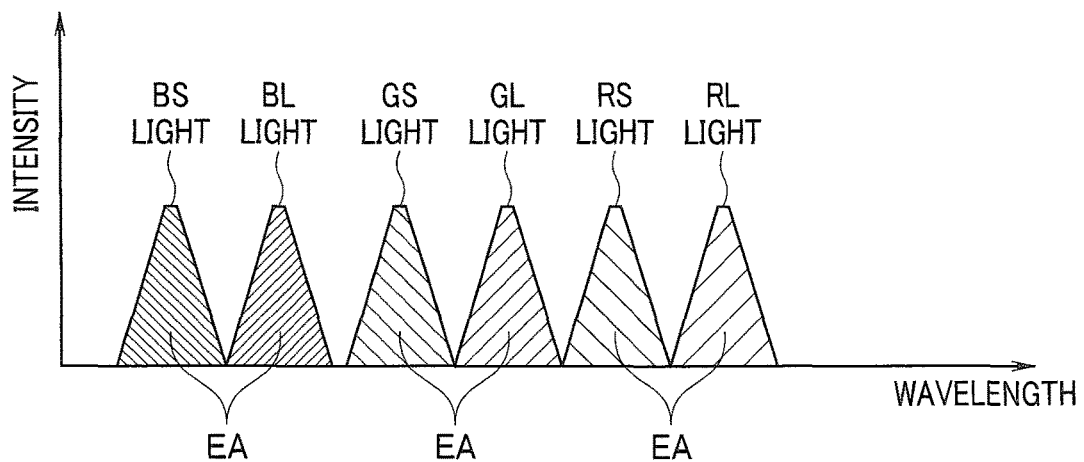
FIG. 2 is a diagram for describing one example of illumination light supplied from a light source device in the first embodiment.

Then, according to the operations of the control portion 47 and the light source control portion 31 as described above, in the illumination period PA of the illumination pattern IP1, for example, as illustrated in FIG. 2, the illumination light including the BS light emitted by the emission light quantity EA and the BL light emitted by the emission light quantity EA is supplied from the light source device 3, return light LA including the BS light and the BL light is emitted from the object illuminated by the illumination light, and image data ILA obtained by picking up the image of the return light LA is outputted from the A/D conversion portion 42 to the WB processing portion 43.

In addition, according to the operations of the control portion 47 and the light source control portion 31 as described above, in the illumination period PB of the illumination pattern IP1, for example, as illustrated in FIG. 2, the illumination light including the GS light emitted by the emission light quantity EA and the GL light emitted by the emission light quantity EA is supplied from the light source device 3, return light LB including the GS light and the GL light is emitted from the object illuminated by the illumination light, and image data ILB obtained by picking up the image of the return light LB is outputted from the A/D conversion portion 42 to the WB processing portion 43.

In addition, according to the operations of the control portion 47 and the light source control portion 31 as described above, in the illumination period PC of the illumination pattern IP1, for example, as illustrated in FIG. 2, the illumination light including the RS light emitted by the emission light quantity EA and the RL light emitted by the emission light quantity EA is supplied from the light source device 3, return light LC including the RS light and the RL light is emitted from the object illuminated by the illumination light, and image data ILC obtained by picking up the image of the return light LC is outputted from the A/D conversion portion 42 to the WB processing portion 43.

The control portion 47 performs the control for causing the white balance processing using the predetermined white balance coefficient to be performed to each image data successively outputted from the A/D conversion portion 42 to the WB processing portion 43.

Figure 3:
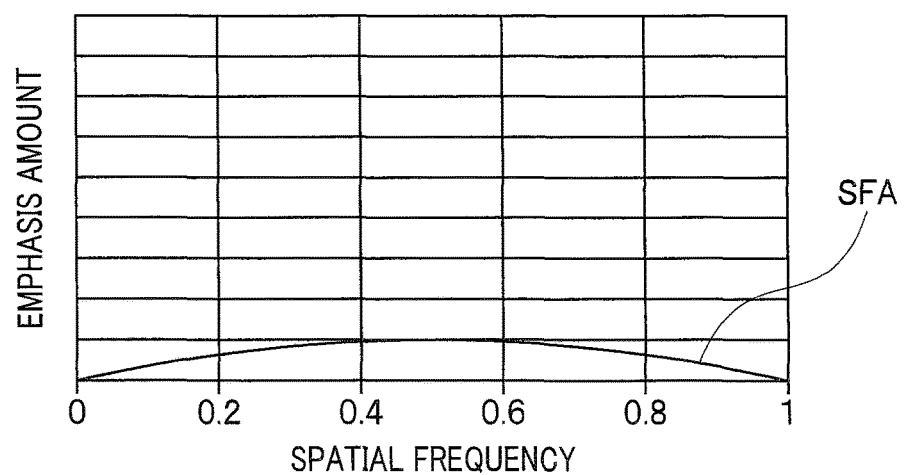
FIG. 3 is a diagram illustrating one example of a filter characteristic of a spatial filter used in spatial filter processing in the first embodiment.

When detecting that the sharpness "off" is selected in the sharpness emphasizing switch, for example, the control portion 47 reads a spatial filter SFA designed to have a filter characteristic as illustrated in FIG. 3 from the memory 47a, and performs the control for causing the spatial filter processing using the read spatial filter SFA to be performed to the sharpness emphasizing portion 44. Note that the filter characteristic in FIG. 3 is illustrated as a characteristic of such a mountain shape that a spatial frequency emphasized by a maximum emphasis amount is present in a middle band.

The sharpness emphasizing portion 44 executes the spatial filter processing using the spatial filter SFA to each of the image data ILA, ILB and ILC outputted from the WB processing portion 43 when the sharpness "off" is selected in the sharpness emphasizing switch according to the control of the control portion 47, and outputs the image data to which the spatial filter processing is executed to the gradation conversion portion 45.

Note that, in the present embodiment, the spatial filter SFA does not have the filter characteristic for highlighting one or more structures included in the biological tissue. Therefore, the sharpness emphasizing portion 44 of the present embodiment does not execute the spatial filter processing for highlighting one or more structures included in the biological tissue to the image data outputted from the WB processing portion 43 when the sharpness "off" is selected in the sharpness emphasizing switch.

Figure 4:
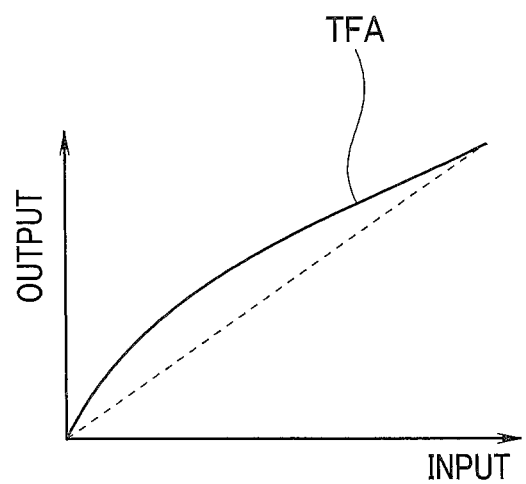
FIG. 4 is a diagram illustrating one example of a gradation conversion function used in gradation conversion processing in the first embodiment.

When detecting that the contrast "normal" is selected in the contrast emphasizing switch, for example, the control portion 47 reads a gradation conversion function TFA having an input/output characteristic as illustrated in FIG. 4 from the memory 47a, and performs the control for causing the gradation conversion processing using the read gradation conversion function TFA to be performed to each image data successively outputted from the sharpness emphasizing portion 44 to the gradation conversion portion 45.

Note that, in the present embodiment, the gradation conversion function TFA does not have the input/output characteristic for highlighting one or more structures included in the biological tissue. Therefore, the gradation conversion portion 45 of the present embodiment does not execute the gradation conversion processing for highlighting one or more structures included in the biological tissue to the image data outputted from the sharpness emphasizing portion 44 when the contrast "normal" is selected in the contrast emphasizing switch.

The control portion 47 performs the control for making the image data ILA outputted from the gradation conversion portion 45 be allocated to the B channel of the display device 5, making the image data ILB outputted from the gradation conversion portion 45 be allocated to the G channel of the display device 5, and making the image data ILC outputted from the gradation conversion portion 45 be allocated to the R channel of the display device 5 to the display control portion 46.

Then, according to the operation of the control portion 47 or the like as described above, when the sharpness "off" is selected in the sharpness emphasizing switch, an observation image in which the structure included in the biological tissue can be observed with visibility almost equal to the visibility in a natural state that the emphasizing processing is not applied is displayed at the display device 5.

On the other hand, the user arranges the distal end portion 2c at a position at which the image of the biological tissue of an observation target existing inside the subject can be picked up, by inserting the insertion portion 2a of the endoscope 2 into the subject. Then, for example, by appropriately selecting the sharpness in the sharpness emphasizing switch according to an observation distance between the distal end portion 2c and the biological tissue of the observation target, the user gives the instruction for highlighting a desired structure included in the biological tissue of the observation target to the control portion 47.

Specifically, for example, in the case that the observation distance between the distal end portion 2c and the biological tissue of the observation target belongs to a distant view, by performing the operation of selecting the sharpness "weak" in the sharpness emphasizing switch, the user gives the instruction for highlighting a blood vessel of a large diameter existing in the deep layer of the biological tissue of the observation target to the control portion 47.

When detecting that the sharpness "weak" is selected in the sharpness emphasizing switch, for example, the control portion 47 generates the emission light quantity ratio control signal for setting the emission light quantity of the blue light sources 32a and 32b and the emission light quantity of the green light sources 32c and 32d to the mutually same emission light quantity EA, setting the emission light quantity of the red light source 32e to an emission light quantity EB larger than the emission light quantity EA, and setting the emission light quantity of the red light source 32f to an emission light quantity EC smaller than the emission light quantity EA, and outputs the signal to the light source control portion 31. Note that, when setting the emission light quantity at the sharpness "weak", the control portion 47 performs adjustment for equalizing a value obtained by adding the emission light quantity EA of the two red light sources 32e and 32f (doubling the emission light quantity EA) at the sharpness "off" and a value obtained by adding the emission light quantities EB and EC.

The light source control portion 31 generates and outputs the light source drive signal for making the blue light sources 32a and 32b and the green light sources 32c and 32d emit the light by the emission light quantity EA, making the red light source 32e emit the light by the emission light quantity EB, and making the red light source 32f emit the light by the emission light quantity EC, when the sharpness "weak" is selected in the sharpness emphasizing switch, according to the emission light quantity ratio control signal outputted from the control portion 47.

Figure 5:
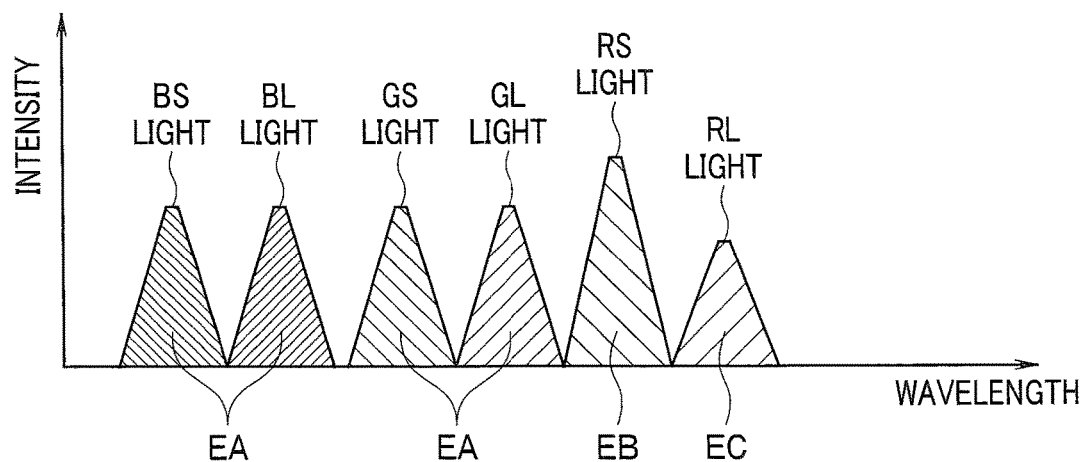
FIG. 5 is a diagram for describing one example of the illumination light supplied from the light source device in the first embodiment.

Then, according to the operations of the control portion 47 and the light source control portion 31 as described above, in the illumination period PA of the illumination pattern IP1, for example, as illustrated in FIG. 5, the illumination light including the BS light emitted by the emission light quantity EA and the BL light emitted by the emission light quantity EA is supplied from the light source device 3, the return light LA including the BS light and the BL light is emitted from the object illuminated by the illumination light, and the image data ILA obtained by picking up the image of the return light LA is outputted from the A/D conversion portion 42 to the WB processing portion 43.

In addition, according to the operations of the control portion 47 and the light source control portion 31 as described above, in the illumination period PB of the illumination pattern IP1, for example, as illustrated in FIG. 5, the illumination light including the GS light emitted by the emission light quantity EA and the GL light emitted by the emission light quantity EA is supplied from the light source device 3, the return light LB including the GS light and the GL light is emitted from the object illuminated by the illumination light, and the image data ILB obtained by picking up the image of the return light LB is outputted from the A/D conversion portion 42 to the WB processing portion 43.

In addition, according to the operations of the control portion 47 and the light source control portion 31 as described above, in the illumination period PC of the illumination pattern IP1, for example, as illustrated in FIG. 5, the illumination light including the RS light emitted by the emission light quantity EB and the RL light emitted by the emission light quantity EC is supplied from the light source device 3, return light LF including the RS light and the RL light is emitted from the object illuminated by the illumination light, and image data ILF obtained by picking up the image of the return light LF is outputted from the A/D conversion portion 42 to the WB processing portion 43.

Figure 6:
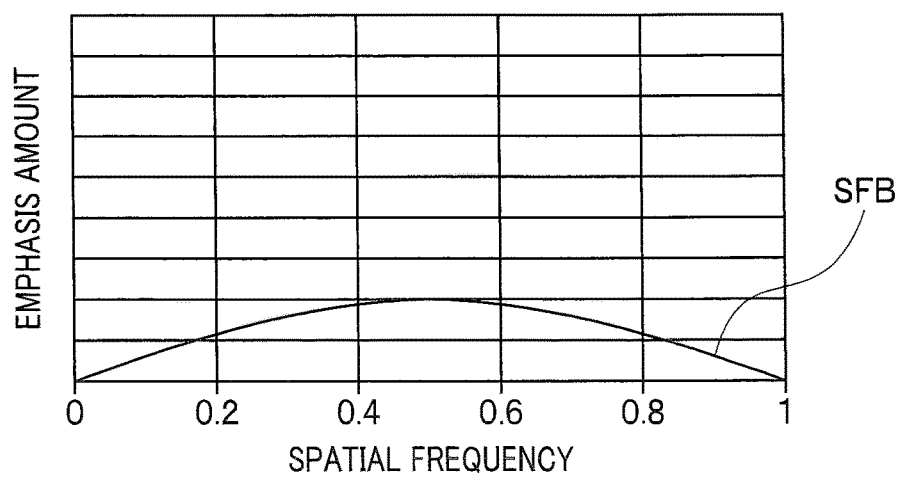
FIG. 6 is a diagram illustrating one example of the filter characteristic of the spatial filter used in the spatial filter processing in the first embodiment.

When detecting that the sharpness "weak" is selected in the sharpness emphasizing switch, for example, the control portion 47 reads a spatial filter SFB designed to have the filter characteristic as illustrated in FIG. 6 from the memory 47a, and performs the control for causing the spatial filter processing using the read spatial filter SFB to be performed to the sharpness emphasizing portion 44. Note that the filter characteristic in FIG. 6 is illustrated as the characteristic that the spatial frequency emphasized by the maximum emphasis amount is the same as the spatial frequency of the spatial filter SFA and the emphasis amount in the entire spatial frequency band is equal to or larger than the emphasis amount of the spatial filter SFA.

The sharpness emphasizing portion 44 executes the spatial filter processing using the spatial filter SFB to each of the image data ILA, ILB and ILF outputted from the WB processing portion 43 when the sharpness "weak" is selected in the sharpness emphasizing switch according to the control of the control portion 47, and outputs the image data to which the spatial filter processing is executed to the gradation conversion portion 45.

The control portion 47 performs the control for making the image data ILA outputted from the gradation conversion portion 45 be allocated to the B channel of the display device 5, making the image data ILB outputted from the gradation conversion portion 45 be allocated to the G channel of the display device 5, and making the image data ILF outputted from the gradation conversion portion 45 be allocated to the R channel of the display device 5 to the display control portion 46.

Then, according to the operation of the control portion 47 or the like as described above, when the sharpness "weak" is selected in the sharpness emphasizing switch, the observation image in which the blood vessel of the large diameter existing in the deep layer of the biological tissue of the observation target is emphasized is displayed at the display device 5. In other words, according to the operation of the control portion 47 or the like as described above, when the sharpness "weak" is selected in the sharpness emphasizing switch, the observation image in which the visibility of the blood vessel of the large diameter existing in the deep layer of the biological tissue of the observation target is improved more than the visibility at the sharpness "off" is displayed at the display device 5.

On the other hand, for example, in the case that the observation distance between the distal end portion 2c and the biological tissue of the observation target belongs to an intermediate view, by performing the operation of selecting the sharpness "middle" in the sharpness emphasizing switch, the user gives the instruction for highlighting the blood vessel of the large diameter existing in the deep layer of the biological tissue of the observation target and the blood vessel existing in the middle layer of the biological tissue of the observation target respectively to the control portion 47.

When detecting that the sharpness "middle" is selected in the sharpness emphasizing switch, for example, the control portion 47 generates the emission light quantity ratio control signal for setting the emission light quantity of the blue light sources 32a and 32b to the mutually same emission light quantity EA, setting the emission light quantity of the green light source 32d and the red light source 32e to the mutually same emission light quantity EB, and setting the emission light quantity of the green light source 32c and the red light source 32f to the mutually same emission light quantity EC, and outputs the signal to the light source control portion 31. Note that, when setting the emission light quantity at the sharpness "middle", the control portion 47 performs the adjustment for equalizing the value obtained by adding the emission light quantity EA of the two green light sources 32c and 32d (doubling the emission light quantity EA) at the sharpness "off" and the value obtained by adding the emission light quantities EB and EC.

The light source control portion 31 generates and outputs the light source drive signal for making the blue light sources 32a and 32b emit the light by the emission light quantity EA, making the green light source 32d and the red light source 32e emit the light by the emission light quantity EB, and making the green light source 32c and the red light source 32f emit the light by the emission light quantity EC, when the sharpness "middle" is selected in the sharpness emphasizing switch, according to the emission light quantity ratio control signal outputted from the control portion 47.

Figure 7:
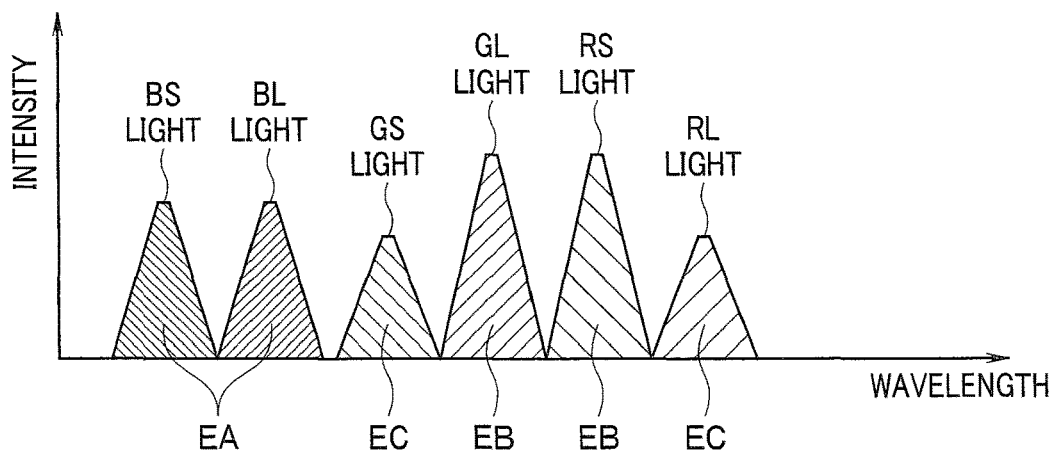
FIG. 7 is a diagram for describing one example of the illumination light supplied from the light source device in the first embodiment.

Then, according to the operations of the control portion 47 and the light source control portion 31 as described above, in the illumination period PA of the illumination pattern IP1, for example, as illustrated in FIG. 7, the illumination light including the BS light emitted by the emission light quantity EA and the BL light emitted by the emission light quantity EA is supplied from the light source device 3, the return light LA including the BS light and the BL light is emitted from the object illuminated by the illumination light, and the image data ILA obtained by picking up the image of the return light LA is outputted from the A/D conversion portion 42 to the WB processing portion 43.

In addition, according to the operations of the control portion 47 and the light source control portion 31 as described above, in the illumination period PB of the illumination pattern IP1, for example, as illustrated in FIG. 7, the illumination light including the GS light emitted by the emission light quantity EC and the GL light emitted by the emission light quantity EB is supplied from the light source device 3, return light LE including the GS light and the GL light is emitted from the object illuminated by the illumination light, and image data ILE obtained by picking up the image of the return light LE is outputted from the A/D conversion portion 42 to the WB processing portion 43.

In addition, according to the operations of the control portion 47 and the light source control portion 31 as described above, in the illumination period PC of the illumination pattern IP1, for example, as illustrated in FIG. 7, the illumination light including the RS light emitted by the emission light quantity EB and the RL light emitted by the emission light quantity EC is supplied from the light source device 3, the return light LF including the RS light and the RL light is emitted from the object illuminated by the illumination light, and the image data ILF obtained by picking up the image of the return light LF is outputted from the A/D conversion portion 42 to the WB processing portion 43.

Figure 8:
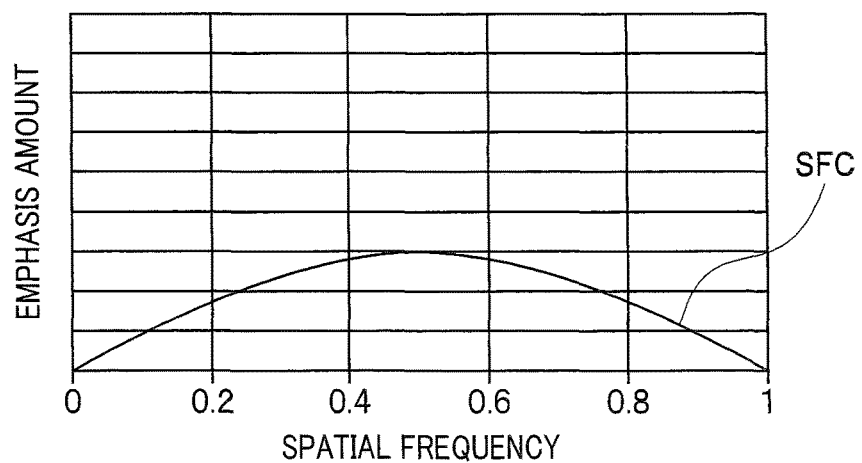
FIG. 8 is a diagram illustrating one example of the filter characteristic of the spatial filter used in the spatial filter processing in the first embodiment.

When detecting that the sharpness "middle" is selected in the sharpness emphasizing switch, for example, the control portion 47 reads a spatial filter SFC designed to have the filter characteristic as illustrated in FIG. 8 from the memory 47a, and performs the control for causing the spatial filter processing using the read spatial filter SFC to be performed to the sharpness emphasizing portion 44. Note that the filter characteristic in FIG. 8 is illustrated as the characteristic that the spatial frequency emphasized by the maximum emphasis amount is the same as the spatial frequency of the spatial filters SFA and SFB and the emphasis amount in the entire spatial frequency band is equal to or larger than the emphasis amount of the spatial filter SFB.

The sharpness emphasizing portion 44 executes the spatial filter processing using the spatial filter SFC to each of the image data ILA, ILE and ILF outputted from the WB processing portion 43 when the sharpness "middle" is selected in the sharpness emphasizing switch according to the control of the control portion 47, and outputs the image data to which the spatial filter processing is executed to the gradation conversion portion 45.

The control portion 47 performs the control for making the image data ILA outputted from the gradation conversion portion 45 be allocated to the B channel of the display device 5, making the image data ILE outputted from the gradation conversion portion 45 be allocated to the G channel of the display device 5, and making the image data ILF outputted from the gradation conversion portion 45 be allocated to the R channel of the display device 5 to the display control portion 46.

Then, according to the operation of the control portion 47 or the like as described above, when the sharpness "middle" is selected in the sharpness emphasizing switch, the observation image in which the blood vessel of the large diameter existing in the deep layer of the biological tissue of the observation target and the blood vessel existing in the middle layer of the biological tissue of the observation target are respectively emphasized is displayed at the display device 5. In other words, according to the operation of the control portion 47 or the like as described above, when the sharpness "middle" is selected in the sharpness emphasizing switch, the observation image in which the visibility of the blood vessel of the large diameter existing in the deep layer of the biological tissue of the observation target and the blood vessel existing in the middle layer of the biological tissue of the observation target is improved respectively more than the visibility at the sharpness "off" is displayed at the display device 5.

On the other hand, for example, in the case that the observation distance between the distal end portion 2c and the biological tissue of the observation target belongs to a close view, by performing the operation of selecting the sharpness "strong" in the sharpness emphasizing switch, the user gives the instruction for highlighting the blood vessel of the large diameter existing in the deep layer of the biological tissue of the observation target, the blood vessel existing in the middle layer of the biological tissue of the observation target, and a capillary and a mucosal structure existing in the surface layer of the biological tissue of the observation target respectively to the control portion 47.

When detecting that the sharpness "strong" is selected in the sharpness emphasizing switch, for example, the control portion 47 generates the emission light quantity ratio control signal for setting the emission light quantity of the blue light source 32a, the green light source 32d and the red light source 32e to the mutually same emission light quantity EB, and setting the emission light quantity of the blue light source 32b, the green light source 32c and the red light source 32f to the mutually same emission light quantity EC, and outputs the signal to the light source control portion 31. Note that, when setting the emission light quantity at the sharpness "strong", the control portion 47 performs the adjustment for equalizing the value obtained by adding the emission light quantity EA of the two blue light sources 32a and 32b (doubling the emission light quantity EA) at the sharpness "off" and the value obtained by adding the emission light quantities EB and EC.

The light source control portion 31 generates and outputs the light source drive signal for making the blue light source 32a, the green light source 32d and the red light source 32e emit the light by the emission light quantity EB, and making the blue light source 32b, the green light source 32c and the red light source 32f emit the light by the emission light quantity EC, when the sharpness "strong" is selected in the sharpness emphasizing switch, according to the emission light quantity ratio control signal outputted from the control portion 47.

Figure 9:
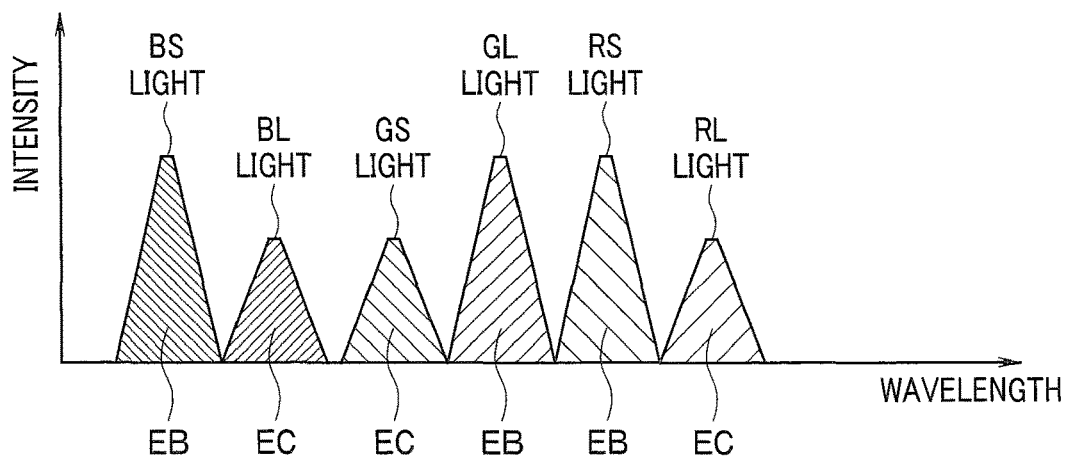
FIG. 9 is a diagram for describing one example of the illumination light supplied from the light source device in the first embodiment.

Then, according to the operations of the control portion 47 and the light source control portion 31 as described above, in the illumination period PA of the illumination pattern IP1, for example, as illustrated in FIG. 9, the illumination light including the BS light emitted by the emission light quantity EB and the BL light emitted by the emission light quantity EC is supplied from the light source device 3, return light LD including the BS light and the BL light is emitted from the object illuminated by the illumination light, and image data ILD obtained by picking up the image of the return light LD is outputted from the A/D conversion portion 42 to the WB processing portion 43.

In addition, according to the operations of the control portion 47 and the light source control portion 31 as described above, in the illumination period PB of the illumination pattern IP1, for example, as illustrated in FIG. 9, the illumination light including the GS light emitted by the emission light quantity EC and the GL light emitted by the emission light quantity EB is supplied from the light source device 3, the return light LE including the GS light and the GL light is emitted from the object illuminated by the illumination light, and the image data ILE obtained by picking up the image of the return light LE is outputted from the A/D conversion portion 42 to the WB processing portion 43.

In addition, according to the operations of the control portion 47 and the light source control portion 31 as described above, in the illumination period PC of the illumination pattern IP1, for example, as illustrated in FIG. 9, the illumination light including the RS light emitted by the emission light quantity EB and the RL light emitted by the emission light quantity EC is supplied from the light source device 3, the return light LF including the RS light and the RL light is emitted from the object illuminated by the illumination light, and the image data ILF obtained by picking up the image of the return light LF is outputted from the A/D conversion portion 42 to the WB processing portion 43.

Figure 10:
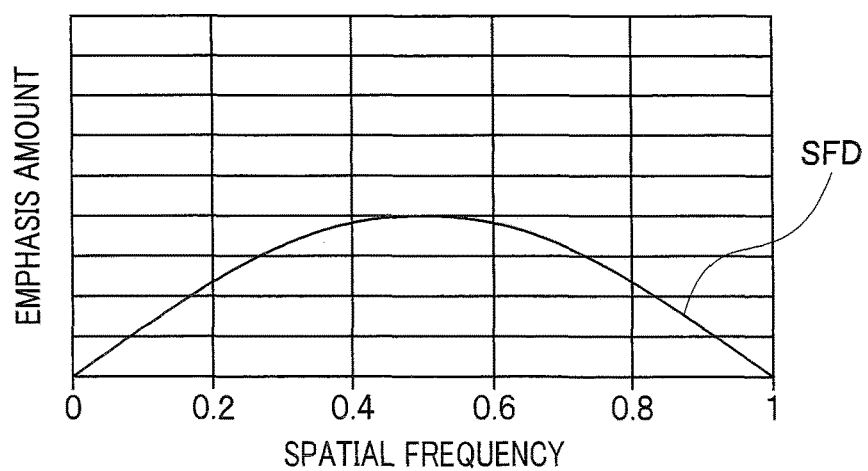
FIG. 10 is a diagram illustrating one example of the filter characteristic of the spatial filter used in the spatial filter processing in the first embodiment.

When detecting that the sharpness "strong" is selected in the sharpness emphasizing switch, for example, the control portion 47 reads a spatial filter SFD designed to have the filter characteristic as illustrated in FIG. 10 from the memory 47a, and performs the control for causing the spatial filter processing using the read spatial filter SFD to be performed to the sharpness emphasizing portion 44. Note that the filter characteristic in FIG. 10 is illustrated as the characteristic that the spatial frequency emphasized by the maximum emphasis amount is the same as the spatial frequency of the spatial filters SFA to SFC and the emphasis amount in the entire spatial frequency band is equal to or larger than the emphasis amount of the spatial filter SFC.

The sharpness emphasizing portion 44 executes the spatial filter processing using the spatial filter SFD to each of the image data ILD, ILE and ILF outputted from the WB processing portion 43 when the sharpness "strong" is selected in the sharpness emphasizing switch according to the control of the control portion 47, and outputs the image data to which the spatial filter processing is executed to the gradation conversion portion 45.

The control portion 47 performs the control for making the image data ILD outputted from the gradation conversion portion 45 be allocated to the B channel of the display device 5, making the image data ILE outputted from the gradation conversion portion 45 be allocated to the G channel of the display device 5, and making the image data ILF outputted from the gradation conversion portion 45 be allocated to the R channel of the display device 5 to the display control portion 46.

Then, according to the operation of the control portion 47 or the like as described above, when the sharpness "strong" is selected in the sharpness emphasizing switch, the observation image in which the blood vessel of the large diameter existing in the deep layer of the biological tissue of the observation target, the blood vessel existing in the middle layer of the biological tissue of the observation target, and the capillary and the mucosal structure existing in the surface layer of the biological tissue of the observation target are respectively emphasized is displayed at the display device 5. In other words, according to the operation of the control portion 47 or the like as described above, when the sharpness "strong" is selected in the sharpness emphasizing switch, the observation image in which the visibility of the blood vessel of the large diameter existing in the deep layer of the biological tissue of the observation target, the blood vessel existing in the middle layer of the biological tissue of the observation target, and the capillary and the mucosal structure existing in the surface layer of the biological tissue of the observation target is improved respectively more than the visibility at the sharpness "off" is displayed at the display device 5.

Figure 11:
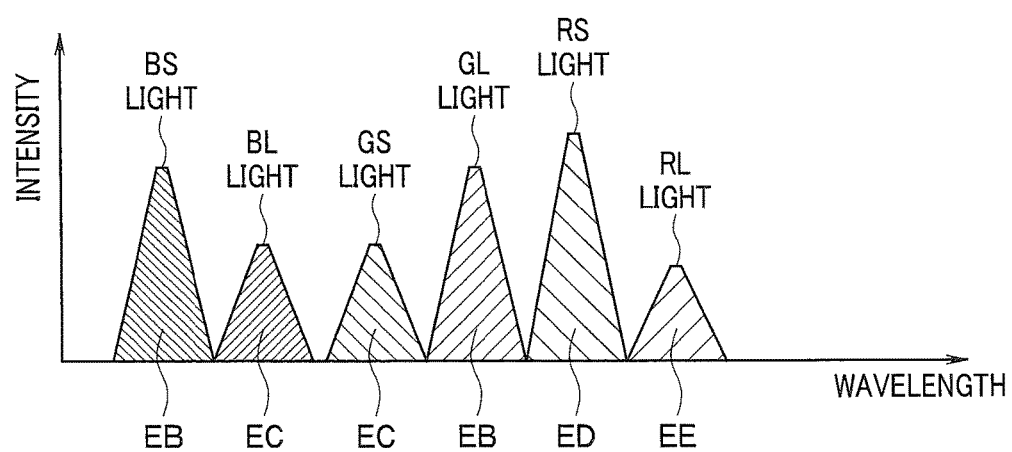
FIG. 11 is a diagram for describing one example of the illumination light supplied from the light source device in the first embodiment.
Figure 12:
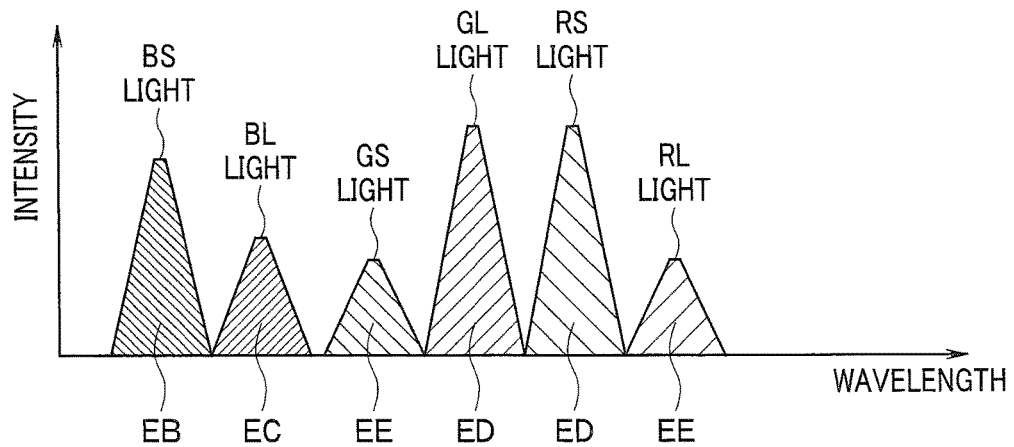
FIG. 12 is a diagram for describing one example of the illumination light supplied from the light source device in the first embodiment.
Figure 13:
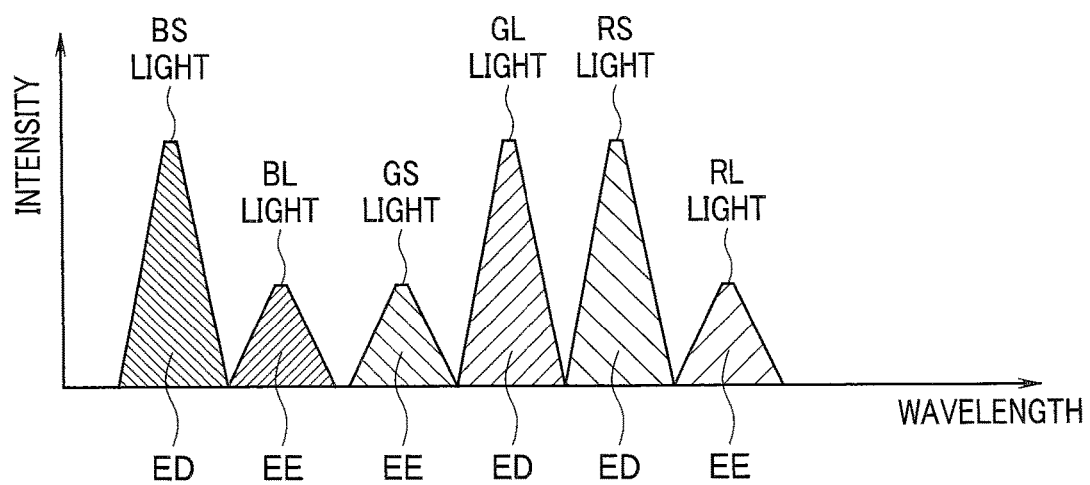
FIG. 13 is a diagram for describing one example of the illumination light supplied from the light source device in the first embodiment.

Note that, in the case of setting the emission light quantities of the respective light sources at the sharpness "off" as in FIG. 9, for example, the control portion 47 of the present embodiment may set the emission light quantities of the respective light sources at the sharpness "weak" as in FIG. 11, set the emission light quantities of the respective light sources at the sharpness "middle" as in FIG. 12, and set the emission light quantities of the respective light sources at the sharpness "strong" as in FIG. 13.

Specifically, when detecting that the sharpness "weak" is selected in the sharpness emphasizing switch, for example, the control portion 47 generates the emission light quantity ratio control signal for setting the emission light quantity of the blue light source 32a and the green light source 32d to the mutually same emission light quantity EB, setting the emission light quantity of the blue light source 32b and the green light source 32c to the mutually same emission light quantity EC, setting the emission light quantity of the red light source 32e to an emission light quantity ED larger than the emission light quantity EB, and setting the emission light quantity of the red light source 32f to an emission light quantity EE smaller than the emission light quantity EC, and outputs the signal to the light source control portion 31. Note that, when setting the emission light quantity at the sharpness "weak", the control portion 47 performs the adjustment for equalizing the value obtained by adding the emission light quantity EB of the red light source 32e and the emission light quantity EC of the red light source 32f at the sharpness "off" and the value obtained by adding the emission light quantities ED and EE.

The light source control portion 31 generates and outputs the light source drive signal for making the blue light source 32a and the green light source 32d emit the light by the emission light quantity EB, making the blue light source 32b and the green light source 32c emit the light by the emission light quantity EC, making the red light source 32e emit the light by the emission light quantity ED, and making the red light source 32f emit the light by the emission light quantity EE, when the sharpness "weak" is selected in the sharpness emphasizing switch, according to the emission light quantity ratio control signal outputted from the control portion 47.

Then, according to the operations of the control portion 47 and the light source control portion 31 as described above, in the illumination period PA of the illumination pattern IP1, for example, as illustrated in FIG. 11, the illumination light including the BS light emitted by the emission light quantity EB and the BL light emitted by the emission light quantity EC is supplied from the light source device 3.

In addition, according to the operations of the control portion 47 and the light source control portion 31 as described above, in the illumination period PB of the illumination pattern IP1, for example, as illustrated in FIG. 11, the illumination light including the GS light emitted by the emission light quantity EC and the GL light emitted by the emission light quantity EB is supplied from the light source device 3.

In addition, according to the operations of the control portion 47 and the light source control portion 31 as described above, in the illumination period PC of the illumination pattern IP1, for example, as illustrated in FIG. 11, the illumination light including the RS light emitted by the emission light quantity ED and the RL light emitted by the emission light quantity EE is supplied from the light source device 3.

Note that, in the case that the emission light quantities of the respective light sources at the sharpness "weak" are set as in FIG. 11, the spatial filter processing using the spatial filter SFB may be performed in the sharpness emphasizing portion 44.

On the other hand, when detecting that the sharpness "middle" is selected in the sharpness emphasizing switch, for example, the control portion 47 generates the emission light quantity ratio control signal for setting the emission light quantity of the blue light source 32a to the emission light quantity EB, setting the emission light quantity of the blue light source 32b to the emission light quantity EC, setting the emission light quantity of the green light source 32d and the red light source 32e to the mutually same emission light quantity ED, and setting the emission light quantity of the green light source 32c and the red light source 32f to the mutually same emission light quantity EE, and outputs the signal to the light source control portion 31. Note that, when setting the emission light quantity at the sharpness "middle", the control portion 47 performs the adjustment for equalizing the value obtained by adding the emission light quantity EC of the green light source 32c and the emission light quantity EB of the green light source 32d at the sharpness "off" and the value obtained by adding the emission light quantities ED and EE.

The light source control portion 31 generates and outputs the light source drive signal for making the blue light source 32a emit the light by the emission light quantity EB, making the blue light source 32b emit the light by the emission light quantity EC, making the green light source 32d and the red light source 32e emit the light by the emission light quantity ED, and making the green light source 32c and the red light source 32f emit the light by the emission light quantity EE, when the sharpness "middle" is selected in the sharpness emphasizing switch, according to the emission light quantity ratio control signal outputted from the control portion 47.

Then, according to the operations of the control portion 47 and the light source control portion 31 as described above, in the illumination period PA of the illumination pattern IP1, for example, as illustrated in FIG. 12, the illumination light including the BS light emitted by the emission light quantity EB and the BL light emitted by the emission light quantity EC is supplied from the light source device 3.

In addition, according to the operations of the control portion 47 and the light source control portion 31 as described above, in the illumination period PB of the illumination pattern IP1, for example, as illustrated in FIG. 12, the illumination light including the GS light emitted by the emission light quantity EE and the GL light emitted by the emission light quantity ED is supplied from the light source device 3.

In addition, according to the operations of the control portion 47 and the light source control portion 31 as described above, in the illumination period PC of the illumination pattern IP1, for example, as illustrated in FIG. 12, the illumination light including the RS light emitted by the emission light quantity ED and the RL light emitted by the emission light quantity EE is supplied from the light source device 3.

Note that, in the case that the emission light quantities of the respective light sources at the sharpness "middle" are set as in FIG. 12, the spatial filter processing using the spatial filter SFC may be performed in the sharpness emphasizing portion 44.

On the other hand, when detecting that the sharpness "strong" is selected in the sharpness emphasizing switch, for example, the control portion 47 generates the emission light quantity ratio control signal for setting the emission light quantity of the blue light source 32a, the green light source 32d and the red light source 32e to the mutually same emission light quantity ED, and setting the emission light quantity of the blue light source 32b, the green light source 32c and the red light source 32f to the mutually same emission light quantity EE, and outputs the signal to the light source control portion 31. Note that, when setting the emission light quantity at the sharpness "strong", the control portion 47 performs the adjustment for equalizing the value obtained by adding the emission light quantity EB of the blue light source 32a and the emission light quantity EC of the blue light source 32b at the sharpness "off" and the value obtained by adding the emission light quantities ED and EE.

The light source control portion 31 generates and outputs the light source drive signal for making the blue light source 32a, the green light source 32d and the red light source 32e emit the light by the emission light quantity ED, and making the blue light source 32b, the green light source 32c and the red light source 32f emit the light by the emission light quantity EE, when the sharpness "strong" is selected in the sharpness emphasizing switch, according to the emission light quantity ratio control signal outputted from the control portion 47.

Then, according to the operations of the control portion 47 and the light source control portion 31 as described above, in the illumination period PA of the illumination pattern IP1, for example, as illustrated in FIG. 13, the illumination light including the BS light emitted by the emission light quantity ED and the BL light emitted by the emission light quantity EE is supplied from the light source device 3.

In addition, according to the operations of the control portion 47 and the light source control portion 31 as described above, in the illumination period PB of the illumination pattern IP1, for example, as illustrated in FIG. 13, the illumination light including the GS light emitted by the emission light quantity EE and the GL light emitted by the emission light quantity ED is supplied from the light source device 3.

In addition, according to the operations of the control portion 47 and the light source control portion 31 as described above, in the illumination period PC of the illumination pattern IP1, for example, as illustrated in FIG. 13, the illumination light including the RS light emitted by the emission light quantity ED and the RL light emitted by the emission light quantity EE is supplied from the light source device 3.

Note that, in the case that the emission light quantities of the respective light sources at the sharpness "strong" are set as in FIG. 13, the spatial filter processing using the spatial filter SFD may be performed in the sharpness emphasizing portion 44.

Note that, in the present embodiment, for example, when the emission light quantities of the respective light sources of the light source unit 32 are set to the emission light quantities as illustrated in FIG. 5, the spatial filter processing using the spatial filter SFA may be executed to the image data ILA and ILB, and the spatial filter processing using the spatial filter SFB may be executed to the image data ILF. In addition, in the present embodiment, for example, when the emission light quantities of the respective light sources of the light source unit 32 are set to the emission light quantities as illustrated in FIG. 7, the spatial filter processing using the spatial filter SFA may be executed to the image data ILA, the spatial filter processing using the spatial filter SFB may be executed to the image data ILE, and the spatial filter processing using the spatial filter SFC may be executed to the image data ILF. Furthermore, in the present embodiment, for example, when the emission light quantities of the respective light sources of the light source unit 32 are set to the emission light quantities as illustrated in FIG. 9, the spatial filter processing using the spatial filter SFB may be executed to the image data ILD, the spatial filter processing using the spatial filter SFC may be executed to the image data ILE, and the spatial filter processing using the spatial filter SFD may be executed to the image data ILF. That is, according to the present embodiment, when the emission light quantity ratio of the illumination light supplied from the light source device 3 is changed from the emission light quantity ratio at the sharpness "off", only the filter characteristic of the spatial filter applied to the image data corresponding to the changed emission light quantity ratio may be changed according to the sharpness selected in the sharpness emphasizing switch.

On the other hand, in the present embodiment, combinations of the emission light quantities of the respective light sources at the sharpness other than the sharpness "off" and the filter characteristic of the spatial filter may be the combinations illustrated in FIG. 14 to FIG. 19 for example, instead of the combinations illustrated in FIG. 5 to FIG. 10. The specific operations or the like performed in such a case will be described below. Note that, hereinafter, specific descriptions relating to parts to which the already-described operations or the like are applicable will be appropriately omitted for simplification. In addition, in the descriptions relating to FIG. 14 to FIG. 19, the case that the sharpness of one of the four of "off", "for the distant view", "for the intermediate view" and "for the close view" can be selected as the desired sharpness (emphasis degree) in the sharpness emphasizing switch will be described as an example.

For example, in the case that the observation distance between the distal end portion 2c and the biological tissue of the observation target belongs to the distant view, by performing the operation of selecting the sharpness "for the distant view" in the sharpness emphasizing switch, the user gives the instruction for highlighting the blood vessel of the large diameter existing in the deep layer of the biological tissue of the observation target to the control portion 47.

When detecting that the sharpness "for the distant view" is selected in the sharpness emphasizing switch, for example, the control portion 47 generates the emission light quantity ratio control signal for setting the emission light quantity of the blue light sources 32a and 32b and the emission light quantity of the green light sources 32c and 32d to the mutually same emission light quantity EA, setting the emission light quantity of the red light source 32e to the emission light quantity EB, and setting the emission light quantity of the red light source 32f to the emission light quantity EC, and outputs the signal to the light source control portion 31. Note that, when setting the emission light quantity at the sharpness "for the distant view", the control portion 47 performs the adjustment for equalizing the value obtained by adding the emission light quantity EA of the two red light sources 32e and 32f (doubling the emission light quantity EA) at the sharpness "off" and the value obtained by adding the emission light quantities EB and EC.

The light source control portion 31 generates and outputs the light source drive signal for making the blue light sources 32a and 32b and the green light sources 32c and 32d emit the light by the emission light quantity EA, making the red light source 32e emit the light by the emission light quantity EB, and making the red light source 32f emit the light by the emission light quantity EC, when the sharpness "for the distant view" is selected in the sharpness emphasizing switch, according to the emission light quantity ratio control signal outputted from the control portion 47.

Figure 14:
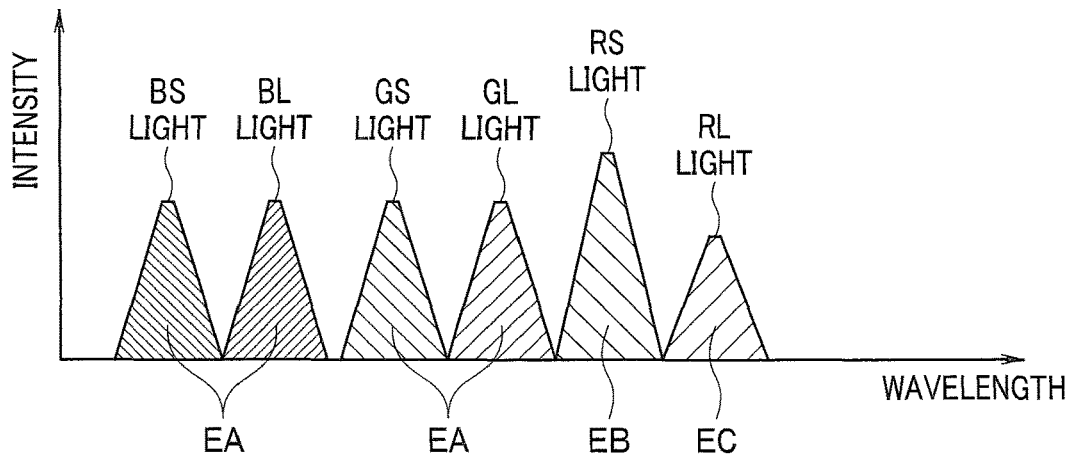
FIG. 14 is a diagram for describing one example of the illumination light supplied from the light source device in the first embodiment.

Then, according to the operations of the control portion 47 and the light source control portion 31 as described above, in the illumination period PA of the illumination pattern IP1, for example, as illustrated in FIG. 14, the illumination light including the BS light emitted by the emission light quantity EA and the BL light emitted by the emission light quantity EA is supplied from the light source device 3, the return light LA including the BS light and the BL light is emitted from the object illuminated by the illumination light, and the image data ILA obtained by picking up the image of the return light LA is outputted from the A/D conversion portion 42 to the WB processing portion 43.

In addition, according to the operations of the control portion 47 and the light source control portion 31 as described above, in the illumination period PB of the illumination pattern IP1, for example, as illustrated in FIG. 14, the illumination light including the GS light emitted by the emission light quantity EA and the GL light emitted by the emission light quantity EA is supplied from the light source device 3, the return light LB including the GS light and the GL light is emitted from the object illuminated by the illumination light, and the image data ILB obtained by picking up the image of the return light LB is outputted from the A/D conversion portion 42 to the WB processing portion 43.

In addition, according to the operations of the control portion 47 and the light source control portion 31 as described above, in the illumination period PC of the illumination pattern IP1, for example, as illustrated in FIG. 14, the illumination light including the RS light emitted by the emission light quantity EB and the RL light emitted by the emission light quantity EC is supplied from the light source device 3, the return light LF including the RS light and the RL light is emitted from the object illuminated by the illumination light, and the image data ILF obtained by picking up the image of the return light LF is outputted from the A/D conversion portion 42 to the WB processing portion 43.

Figure 15:
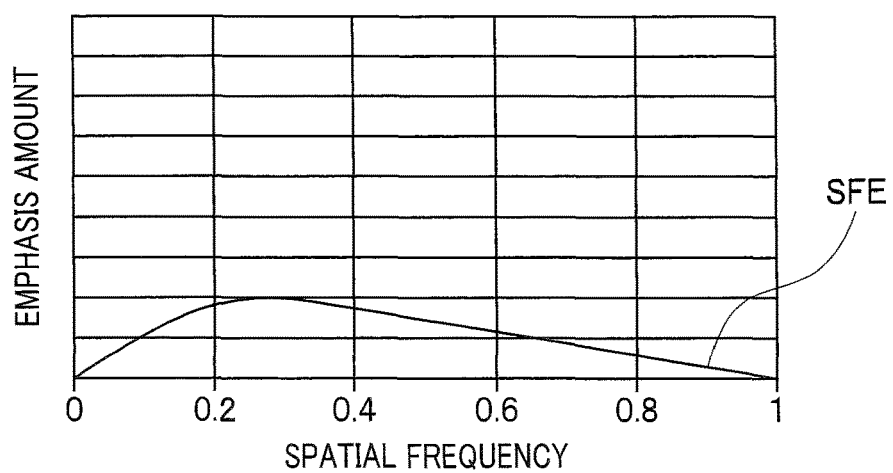
FIG. 15 is a diagram illustrating one example of the filter characteristic of the spatial filter used in the spatial filter processing in the first embodiment.

When detecting that the sharpness "for the distant view" is selected in the sharpness emphasizing switch, for example, the control portion 47 reads a spatial filter SFE designed to have the filter characteristic as illustrated in FIG. 15 from the memory 47a, and performs the control for causing the spatial filter processing using the read spatial filter SFE to be performed to the sharpness emphasizing portion 44. Note that the filter characteristic in FIG. 15 is illustrated as the characteristic that the spatial frequency emphasized by the maximum emphasis amount is shifted to a low band side more than the spatial frequency of the spatial filter SFA and the emphasis amount at the spatial frequency of the low band to the middle band is equal to or larger than the emphasis amount of the spatial filter SFA.

The sharpness emphasizing portion 44 executes the spatial filter processing using the spatial filter SFE to each of the image data ILA, ILB and ILF outputted from the WB processing portion 43 when the sharpness "for the distant view" is selected in the sharpness emphasizing switch according to the control of the control portion 47, and outputs the image data to which the spatial filter processing is executed to the gradation conversion portion 45.

The control portion 47 performs the control for making the image data ILA outputted from the gradation conversion portion 45 be allocated to the B channel of the display device 5, making the image data ILB outputted from the gradation conversion portion 45 be allocated to the G channel of the display device 5, and making the image data ILF outputted from the gradation conversion portion 45 be allocated to the R channel of the display device 5 to the display control portion 46.

Then, according to the operation of the control portion 47 or the like as described above, when the sharpness "for the distant view" is selected in the sharpness emphasizing switch, the observation image in which the blood vessel of the large diameter existing in the deep layer of the biological tissue of the observation target is emphasized is displayed at the display device 5. In other words, according to the operation of the control portion 47 or the like as described above, when the sharpness "for the distant view" is selected in the sharpness emphasizing switch, the observation image in which the visibility of the blood vessel of the large diameter existing in the deep layer of the biological tissue of the observation target is improved more than the visibility at the sharpness "off" is displayed at the display device 5.

On the other hand, for example, in the case that the observation distance between the distal end portion 2c and the biological tissue of the observation target belongs to the intermediate view, by performing the operation of selecting the sharpness "for the intermediate view" in the sharpness emphasizing switch, the user gives the instruction for highlighting the blood vessel existing in the middle layer of the biological tissue of the observation target to the control portion 47.

When detecting that the sharpness "for the intermediate view" is selected in the sharpness emphasizing switch, for example, the control portion 47 generates the emission light quantity ratio control signal for setting the emission light quantity of the blue light sources 32a and 32b and the emission light quantity of the red light sources 32e and 32f to the mutually same emission light quantity EA, setting the emission light quantity of the green light source 32d to the emission light quantity EB, and setting the emission light quantity of the green light source 32c to the emission light quantity EC, and outputs the signal to the light source control portion 31. Note that, when setting the emission light quantity at the sharpness "for the intermediate view", the control portion 47 performs the adjustment for equalizing the value obtained by adding the emission light quantity EA of the two green light sources 32c and 32d (doubling the emission light quantity EA) at the sharpness "off" and the value obtained by adding the emission light quantities EB and EC.

The light source control portion 31 generates and outputs the light source drive signal for making the blue light sources 32a and 32b and the red light sources 32e and 32f emit the light by the emission light quantity EA, making the green light source 32d emit the light by the emission light quantity EB, and making the green light source 32c emit the light by the emission light quantity EC, when the sharpness "for the intermediate view" is selected in the sharpness emphasizing switch, according to the emission light quantity ratio control signal outputted from the control portion 47.

Figure 16:
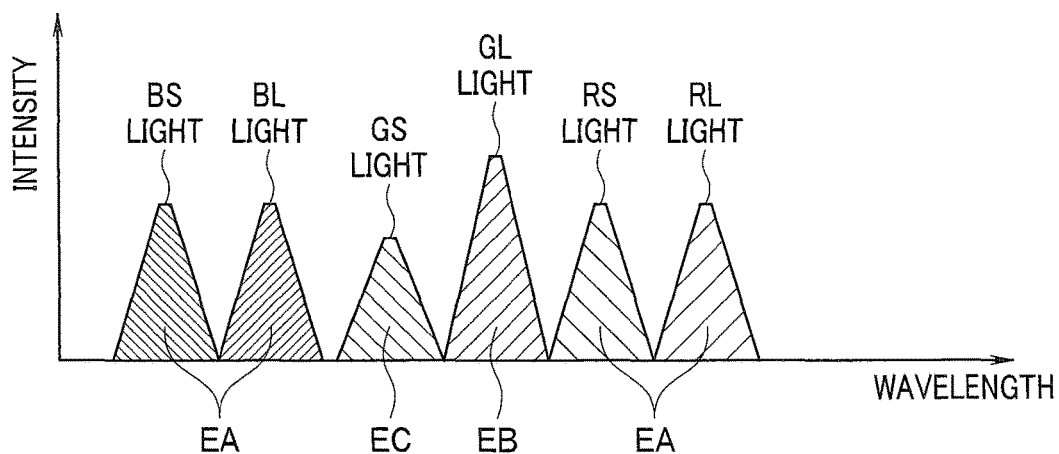
FIG. 16 is a diagram for describing one example of the illumination light supplied from the light source device in the first embodiment.

Then, according to the operations of the control portion 47 and the light source control portion 31 as described above, in the illumination period PA of the illumination pattern IP1, for example, as illustrated in FIG. 16, the illumination light including the BS light emitted by the emission light quantity EA and the BL light emitted by the emission light quantity EA is supplied from the light source device 3, the return light LA including the BS light and the BL light is emitted from the object illuminated by the illumination light, and the image data ILA obtained by picking up the image of the return light LA is outputted from the A/D conversion portion 42 to the WB processing portion 43.

In addition, according to the operations of the control portion 47 and the light source control portion 31 as described above, in the illumination period PB of the illumination pattern IP1, for example, as illustrated in FIG. 16, the illumination light including the GS light emitted by the emission light quantity EC and the GL light emitted by the emission light quantity EB is supplied from the light source device 3, the return light LE including the GS light and the GL light is emitted from the object illuminated by the illumination light, and the image data ILE obtained by picking up the image of the return light LE is outputted from the A/D conversion portion 42 to the WB processing portion 43.

In addition, according to the operations of the control portion 47 and the light source control portion 31 as described above, in the illumination period PC of the illumination pattern IP1, for example, as illustrated in FIG. 16, the illumination light including the RS light emitted by the emission light quantity EA and the RL light emitted by the emission light quantity EA is supplied from the light source device 3, the return light LC including the RS light and the RL light is emitted from the object illuminated by the illumination light, and the image data ILC obtained by picking up the image of the return light LC is outputted from the A/D conversion portion 42 to the WB processing portion 43.

Figure 17:
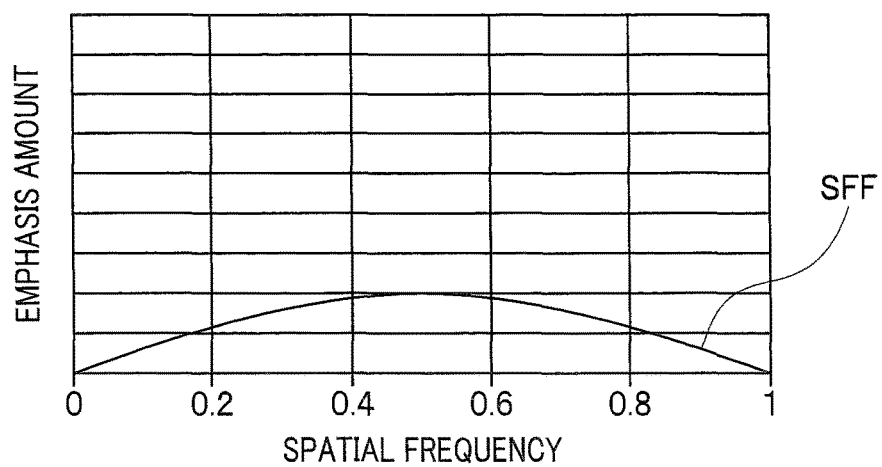
FIG. 17 is a diagram illustrating one example of the filter characteristic of the spatial filter used in the spatial filter processing in the first embodiment.

When detecting that the sharpness "for the intermediate view" is selected in the sharpness emphasizing switch, for example, the control portion 47 reads a spatial filter SFF designed to have the filter characteristic as illustrated in FIG. 17 from the memory 47a, and performs the control for causing the spatial filter processing using the read spatial filter SFF to be performed to the sharpness emphasizing portion 44. Note that the filter characteristic in FIG. 17 is illustrated as the characteristic that the spatial frequency emphasized by the maximum emphasis amount is the same as the spatial frequency of the spatial filter SFA and the emphasis amount in the almost entire spatial frequency band is equal to or larger than the emphasis amount of the spatial filter SFA.

The sharpness emphasizing portion 44 executes the spatial filter processing using the spatial filter SFF to each of the image data ILA, ILE and ILC outputted from the WB processing portion 43 when the sharpness "for the intermediate view" is selected in the sharpness emphasizing switch according to the control of the control portion 47, and outputs the image data to which the spatial filter processing is executed to the gradation conversion portion 45.

The control portion 47 performs the control for making the image data ILA outputted from the gradation conversion portion 45 be allocated to the B channel of the display device 5, making the image data ILE outputted from the gradation conversion portion 45 be allocated to the G channel of the display device 5, and making the image data ILC outputted from the gradation conversion portion 45 be allocated to the R channel of the display device 5 to the display control portion 46.

Then, according to the operation of the control portion 47 or the like as described above, when the sharpness "for the intermediate view" is selected in the sharpness emphasizing switch, the observation image in which the blood vessel existing in the middle layer of the biological tissue of the observation target are respectively emphasized is displayed at the display device 5. In other words, according to the operation of the control portion 47 or the like as described above, when the sharpness "for the intermediate view" is selected in the sharpness emphasizing switch, the observation image in which the visibility of the blood vessel existing in the middle layer of the biological tissue of the observation target is improved more than the visibility at the sharpness "off" is displayed at the display device 5.

On the other hand, for example, in the case that the observation distance between the distal end portion 2c and the biological tissue of the observation target belongs to the close view, by performing the operation of selecting the sharpness "for the close view" in the sharpness emphasizing switch, the user gives the instruction for highlighting the capillary and the mucosal structure existing in the surface layer of the biological tissue of the observation target to the control portion 47.

When detecting that the sharpness "for the close view" is selected in the sharpness emphasizing switch, for example, the control portion 47 generates the emission light quantity ratio control signal for setting the emission light quantity of the green light sources 32c and 32d and the emission light quantity of the red light sources 32e and 32f to the mutually same emission light quantity EA, setting the emission light quantity of the blue light source 32a to the emission light quantity EB, and setting the emission light quantity of the blue light source 32b to the emission light quantity EC, and outputs the signal to the light source control portion 31. Note that, when setting the emission light quantity at the sharpness "for the close view", the control portion 47 performs the adjustment for equalizing the value obtained by adding the emission light quantity EA of the two blue light sources 32a and 32b (doubling the emission light quantity EA) at the sharpness "off" and the value obtained by adding the emission light quantities EB and EC.

The light source control portion 31 generates and outputs the light source drive signal for making the green light sources 32c and 32d and the red light sources 32e and 32f emit the light by the emission light quantity EA, making the blue light source 32a emit the light by the emission light quantity EB, and making the blue light source 32b emit the light by the emission light quantity EC, when the sharpness "for the close view" is selected in the sharpness emphasizing switch, according to the emission light quantity ratio control signal outputted from the control portion 47.

Figure 18:
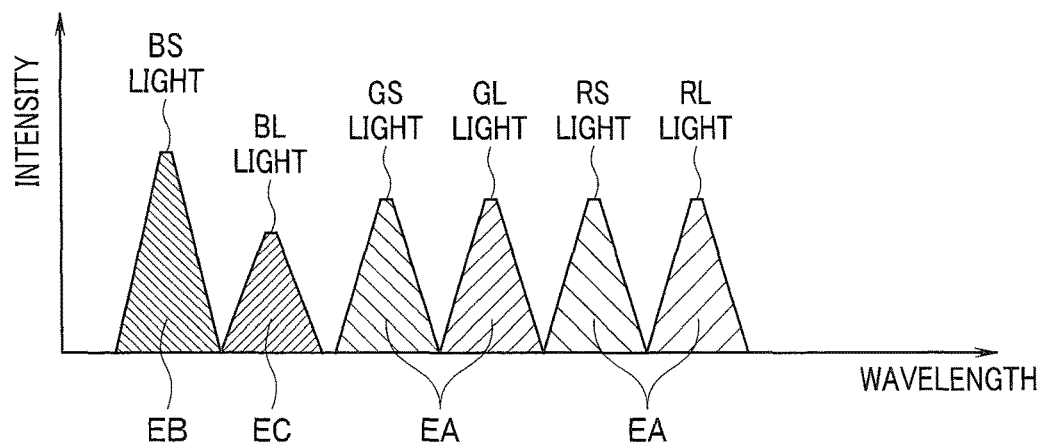
FIG. 18 is a diagram for describing one example of the illumination light supplied from the light source device in the first embodiment.

Then, according to the operations of the control portion 47 and the light source control portion 31 as described above, in the illumination period PA of the illumination pattern IP1, for example, as illustrated in FIG. 18, the illumination light including the BS light emitted by the emission light quantity EB and the BL light emitted by the emission light quantity EC is supplied from the light source device 3, the return light LD including the BS light and the BL light is emitted from the object illuminated by the illumination light, and the image data ILD obtained by picking up the image of the return light LD is outputted from the A/D conversion portion 42 to the WB processing portion 43.

In addition, according to the operations of the control portion 47 and the light source control portion 31 as described above, in the illumination period PB of the illumination pattern IP1, for example, as illustrated in FIG. 18, the illumination light including the GS light emitted by the emission light quantity EA and the GL light emitted by the emission light quantity EA is supplied from the light source device 3, the return light LB including the GS light and the GL light is emitted from the object illuminated by the illumination light, and the image data ILB obtained by picking up the image of the return light LB is outputted from the A/D conversion portion 42 to the WB processing portion 43.

In addition, according to the operations of the control portion 47 and the light source control portion 31 as described above, in the illumination period PC of the illumination pattern IP1, for example, as illustrated in FIG. 18, the illumination light including the RS light emitted by the emission light quantity EA and the RL light emitted by the emission light quantity EA is supplied from the light source device 3, the return light LC including the RS light and the RL light is emitted from the object illuminated by the illumination light, and the image data ILC obtained by picking up the image of the return light LC is outputted from the A/D conversion portion 42 to the WB processing portion 43.

Figure 19:
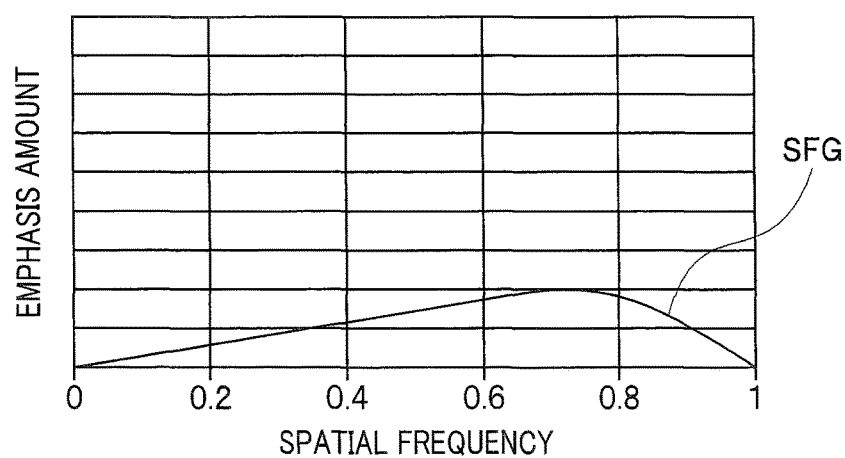
FIG. 19 is a diagram illustrating one example of the filter characteristic of the spatial filter used in the spatial filter processing in the first embodiment.

When detecting that the sharpness "for the close view" is selected in the sharpness emphasizing switch, for example, the control portion 47 reads a spatial filter SFG designed to have the filter characteristic as illustrated in FIG. 19 from the memory 47a, and performs the control for causing the spatial filter processing using the read spatial filter SFG to be performed to the sharpness emphasizing portion 44. Note that the filter characteristic in FIG. 19 is illustrated as the characteristic that the spatial frequency emphasized by the maximum emphasis amount is shifted to a high band side more than the spatial frequency of the spatial filter SFA and the emphasis amount at the spatial frequency of the middle band to the high band is equal to or larger than the emphasis amount of the spatial filter SFA.

The sharpness emphasizing portion 44 executes the spatial filter processing using the spatial filter SFG to each of the image data ILD, ILB and ILC outputted from the WB processing portion 43 when the sharpness "for the close view" is selected in the sharpness emphasizing switch according to the control of the control portion 47, and outputs the image data to which the spatial filter processing is executed to the gradation conversion portion 45.

The control portion 47 performs the control for making the image data ILD outputted from the gradation conversion portion 45 be allocated to the B channel of the display device 5, making the image data ILB outputted from the gradation conversion portion 45 be allocated to the G channel of the display device 5, and making the image data ILC outputted from the gradation conversion portion 45 be allocated to the R channel of the display device 5 to the display control portion 46.

Then, according to the operation of the control portion 47 or the like as described above, when the sharpness "for the close view" is selected in the sharpness emphasizing switch, the observation image in which the capillary and the mucosal structure existing in the surface layer of the biological tissue of the observation target are emphasized is displayed at the display device 5. In other words, according to the operation of the control portion 47 or the like as described above, when the sharpness "for the close view" is selected in the sharpness emphasizing switch, the observation image in which the visibility of the capillary and the mucosal structure existing in the surface layer of the biological tissue of the observation target is improved more than the visibility at the sharpness "off" is displayed at the display device 5.

Figure 20:
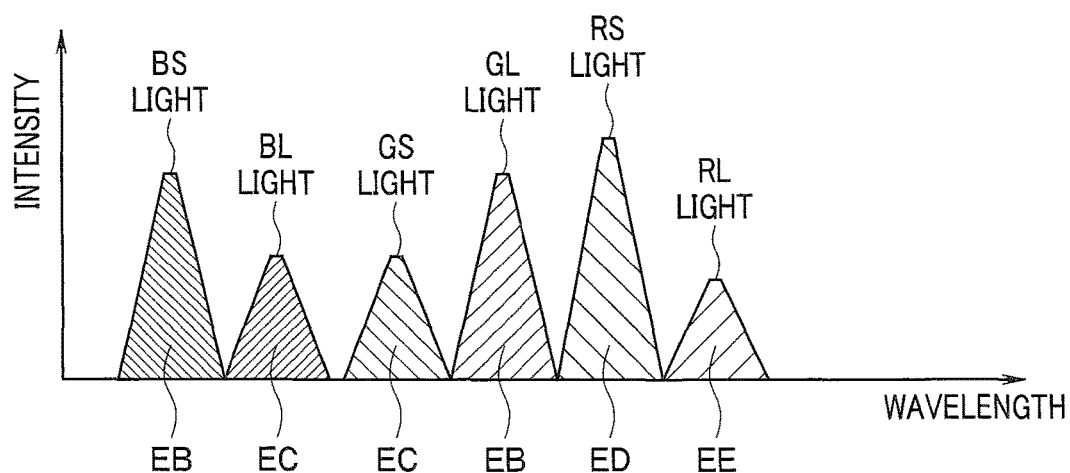
FIG. 20 is a diagram for describing one example of the illumination light supplied from the light source device in the first embodiment.
Figure 21:
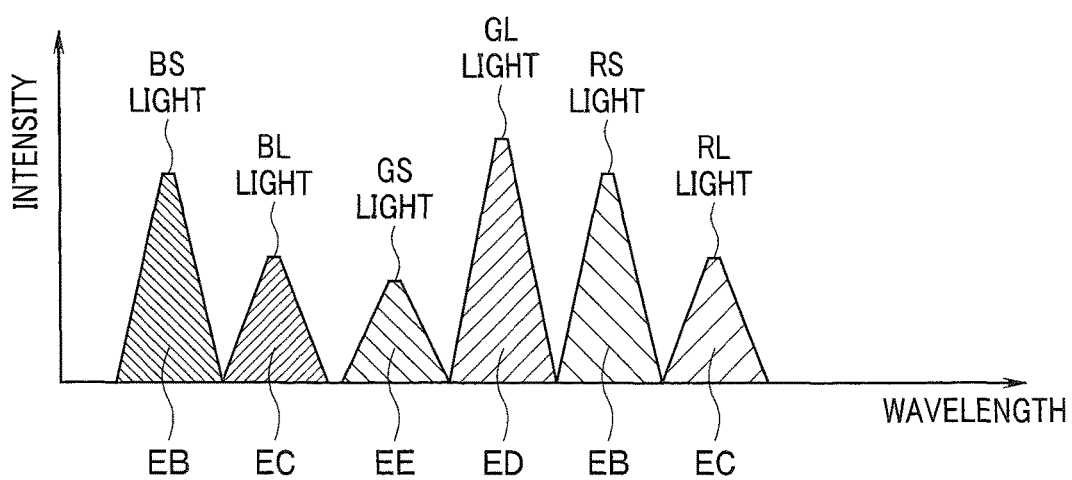
FIG. 21 is a diagram for describing one example of the illumination light supplied from the light source device in the first embodiment.
Figure 22:
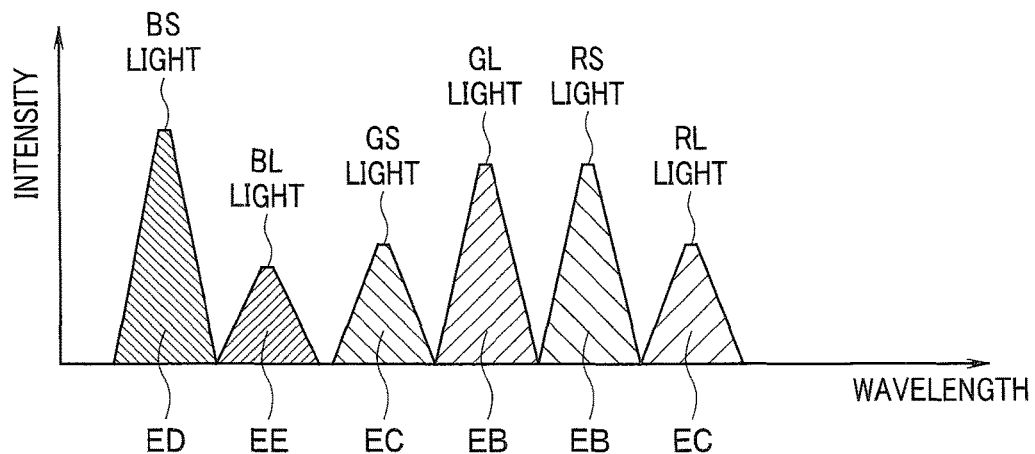
FIG. 22 is a diagram for describing one example of the illumination light supplied from the light source device in the first embodiment.

Note that, in the case of setting the emission light quantities of the respective light sources at the sharpness "off" as in FIG. 9, for example, the control portion 47 of the present embodiment may set the emission light quantities of the respective light sources at the sharpness "for the distant view" as in FIG. 20, set the emission light quantities of the respective light sources at the sharpness "for the intermediate view" as in FIG. 21, and set the emission light quantities of the respective light sources at the sharpness "for the close view" as in FIG. 22.

Specifically, when detecting that the sharpness "for the distant view" is selected in the sharpness emphasizing switch, for example, the control portion 47 generates the emission light quantity ratio control signal for setting the emission light quantity of the blue light source 32a and the green light source 32d to the mutually same emission light quantity EB, setting the emission light quantity of the blue light source 32b and the green light source 32c to the mutually same emission light quantity EC, setting the emission light quantity of the red light source 32e to the emission light quantity ED, and setting the emission light quantity of the red light source 32f to the emission light quantity EE, and outputs the signal to the light source control portion 31. Note that, when setting the emission light quantity at the sharpness "for the distant view", the control portion 47 performs the adjustment for equalizing the value obtained by adding the emission light quantity EB of the red light source 32e and the emission light quantity EC of the red light source 32f at the sharpness "off" and the value obtained by adding the emission light quantities ED and EE.

The light source control portion 31 generates and outputs the light source drive signal for making the blue light source 32a and the green light source 32d emit the light by the emission light quantity EB, making the blue light source 32b and the green light source 32c emit the light by the emission light quantity EC, making the red light source 32e emit the light by the emission light quantity ED, and making the red light source 32f emit the light by the emission light quantity EE, when the sharpness "for the distant view" is selected in the sharpness emphasizing switch, according to the emission light quantity ratio control signal outputted from the control portion 47.

Then, according to the operations of the control portion 47 and the light source control portion 31 as described above, in the illumination period PA of the illumination pattern IP1, for example, as illustrated in FIG. 20, the illumination light including the BS light emitted by the emission light quantity EB and the BL light emitted by the emission light quantity EC is supplied from the light source device 3.

In addition, according to the operations of the control portion 47 and the light source control portion 31 as described above, in the illumination period PB of the illumination pattern IP1, for example, as illustrated in FIG. 20, the illumination light including the GS light emitted by the emission light quantity EC and the GL light emitted by the emission light quantity EB is supplied from the light source device 3.

In addition, according to the operations of the control portion 47 and the light source control portion 31 as described above, in the illumination period PC of the illumination pattern IP1, for example, as illustrated in FIG. 20, the illumination light including the RS light emitted by the emission light quantity ED and the RL light emitted by the emission light quantity EE is supplied from the light source device 3.

Note that, in the case that the emission light quantities of the respective light sources at the sharpness "for the distant view" are set as in FIG. 20, the spatial filter processing using the spatial filter SFE may be performed in the sharpness emphasizing portion 44.

On the other hand, when detecting that the sharpness "for the intermediate view" is selected in the sharpness emphasizing switch, for example, the control portion 47 generates the emission light quantity ratio control signal for setting the emission light quantity of the blue light source 32*a* and the red light source 32*e* to the mutually equal emission light quantity EB, setting the emission light quantity of the blue light source 32*b* and the red light source 32*f* to the mutually equal emission light quantity EC, setting the emission light quantity of the green light source 32*d* to the emission light quantity ED, and setting the emission light quantity of the green light source 32*c* to the emission light quantity EE, and outputs the signal to the light source control portion 31. Note that, when setting the emission light quantity at the sharpness "for the intermediate view", the control portion 47 performs the adjustment for equalizing the value obtained by adding the emission light quantity EB of the green light source 32*d* and the emission light quantity EC of the green light source 32*c* at the sharpness "off" and the value obtained by adding the emission light quantities ED and EE.

The light source control portion 31 generates and outputs the light source drive signal for making the blue light source 32*a* and the red light source 32*e* emit the light by the emission light quantity EB, making the blue light source 32*b* and the red light source 32*f* emit the light by the emission light quantity EC, making the green light source 32*d* emit the light by the emission light quantity ED, and making the green light source 32*c* emit the light by the emission light quantity EE, when the sharpness "for the intermediate view" is selected in the sharpness emphasizing switch, according to the emission light quantity ratio control signal outputted from the control portion 47.

Then, according to the operations of the control portion 47 and the light source control portion 31 as described above, in the illumination period PA of the illumination pattern IP1, for example, as illustrated in FIG. 21, the illumination light including the BS light emitted by the emission light quantity EB and the BL light emitted by the emission light quantity EC is supplied from the light source device 3.

In addition, according to the operations of the control portion 47 and the light source control portion 31 as described above, in the illumination period PB of the illumination pattern IP1, for example, as illustrated in FIG. 21, the illumination light including the GS light emitted by the emission light quantity EE and the GL light emitted by the emission light quantity ED is supplied from the light source device 3.

In addition, according to the operations of the control portion 47 and the light source control portion 31 as described above, in the illumination period PC of the illumination pattern IP1, for example, as illustrated in FIG. 21, the illumination light including the RS light emitted by the emission light quantity EB and the RL light emitted by the emission light quantity EC is supplied from the light source device 3.

Note that, in the case that the emission light quantities of the respective light sources at the sharpness "for the intermediate view" are set as in FIG. 21, the spatial filter processing using the spatial filter SFF may be performed in the sharpness emphasizing portion 44.

On the other hand, when detecting that the sharpness "for the close view" is selected in the sharpness emphasizing switch, for example, the control portion 47 generates the emission light quantity ratio control signal for setting the emission light quantity of the green light source 32*d* and the red light source 32*e* to the mutually same emission light quantity EB, setting the emission light quantity of the green light source 32*c* and the red light source 32*f* to the mutually same emission light quantity EC, setting the emission light quantity of the blue light source 32*a* to the emission light quantity ED, and setting the emission light quantity of the blue light source 32*b* to the emission light quantity EE, and outputs the signal to the light source control portion 31. Note that, when setting the emission light quantity at the sharpness "for the close view", the control portion 47 performs the adjustment for equalizing the value obtained by adding the emission light quantity EB of the blue light source 32*a* and the emission light quantity EC of the blue light source 32*b* at the sharpness "off" and the value obtained by adding the emission light quantities ED and EE.

The light source control portion 31 generates and outputs the light source drive signal for making the green light source 32*d* and the red light source 32*e* emit the light by the emission light quantity EB, making the green light source 32*c* and the red light source 32*f* emit the light by the emission light quantity EC, making the blue light source 32*a* emit the light by the emission light quantity ED, and making the blue light source 32*b* emit the light by the emission light quantity EE, when the sharpness "for the close view" is selected in the sharpness emphasizing switch, according to the emission light quantity ratio control signal outputted from the control portion 47.

Then, according to the operations of the control portion 47 and the light source control portion 31 as described above, in the illumination period PA of the illumination pattern IP1, for example, as illustrated in FIG. 22, the illumination light including the BS light emitted by the emission light quantity ED and the BL light emitted by the emission light quantity EE is supplied from the light source device 3.

In addition, according to the operations of the control portion 47 and the light source control portion 31 as described above, in the illumination period PB of the illumination pattern IP1, for example, as illustrated in FIG. 22, the illumination light including the GS light emitted by the emission light quantity EC and the GL light emitted by the emission light quantity EB is supplied from the light source device 3.

In addition, according to the operations of the control portion 47 and the light source control portion 31 as described above, in the illumination period PC of the illumination pattern IP1, for example, as illustrated in FIG. 22, the illumination light including the RS light emitted by the emission light quantity EB and the RL light emitted by the emission light quantity EC is supplied from the light source device 3.

Note that, in the case that the emission light quantities of the respective light sources at the sharpness "for the close view" are set as in FIG. 22, the spatial filter processing using the spatial filter SFG may be performed in the sharpness emphasizing portion 44.

Here, for example, in the case of considering a situation of performing the spatial filter processing for highlighting the structure such as the blood vessel included in the biological tissue according to the sharpness selected in the sharpness emphasizing switch while the emission light quantity ratio of the respective light sources of the light source unit 32 is fixed at a constant ratio as in FIG. 2, since the spatial filter processing needs to be performed using the spatial filter of a relatively large change rate of the emphasis amount to the spatial frequency depending on the selected sharpness, a problem that an artifact such as color noise is highly frequently generated arises.

In contrast, in the present embodiment, the emission light quantity ratio of the respective light sources of the light source unit 32 and the spatial filter used in the spatial filter processing of the sharpness emphasizing portion 44 are changed together according to the sharpness selected in the sharpness emphasizing switch so that the structure such as the blood vessel included in the biological tissue can be sufficiently highlighted even in the case that the spatial filter processing is performed using the spatial filter of a relatively small change rate of the emphasis amount to the spatial frequency (such as the spatial filters SFB to SFG). Therefore, according to the present embodiment, a generation frequency of the artifact such as the color noise due to the spatial filter processing for highlighting the structure such as the blood vessel included in the biological tissue can be suppressed to a low frequency, that is, decline of image quality which occurs according to the emphasis degree when highlighting the structure can be suppressed.

In addition, according to the present embodiment, the emission light quantities in the respective light sources of the light source unit 32 are adjusted according to the sharpness selected in the sharpness emphasizing switch so that fluctuation of brightness and/or a color tone of the observation image which can occur accompanying changeover of the sharpness in the sharpness emphasizing switch can be suppressed as much as possible.

Note that, by appropriately modifying the configuration or the like relating to the embodiment described above, almost similar operation effects can be obtained even in the case of illuminating the object by the illumination pattern of making the blue light sources 32a and 32b, the green light sources 32c and 32d and the red light sources 32e and 32f simultaneously emit the light, for example.

On the other hand, by modifying the operation relating to the present embodiment, the operation of changing the emission light quantity ratio of the respective light sources of the light source unit 32 and the gradation conversion function used in the gradation conversion processing in the gradation conversion portion 45 together according to the desired contrast selected in the contrast emphasizing switch (not shown in the figure) may be performed. The operation relating to such a modification will be described with the case that the sharpness "off" is selected in the sharpness emphasizing switch as an example.

Specifically, when detecting that the contrast "normal" is selected in the contrast emphasizing switch, the control portion 47 generates the emission light quantity ratio control signal for setting the emission light quantities of the respective light sources of the light source unit 32 to a mutually same emission light quantity EF for example, and outputs the signal to the light source control portion 31.

The light source control portion 31 generates and outputs the light source drive signal for making the respective light sources of the light source unit 32 emit the light by the emission light quantity EF, when the contrast "normal" is selected in the contrast emphasizing switch, according to the emission light quantity ratio control signal outputted from the control portion 47.

Figure 23:
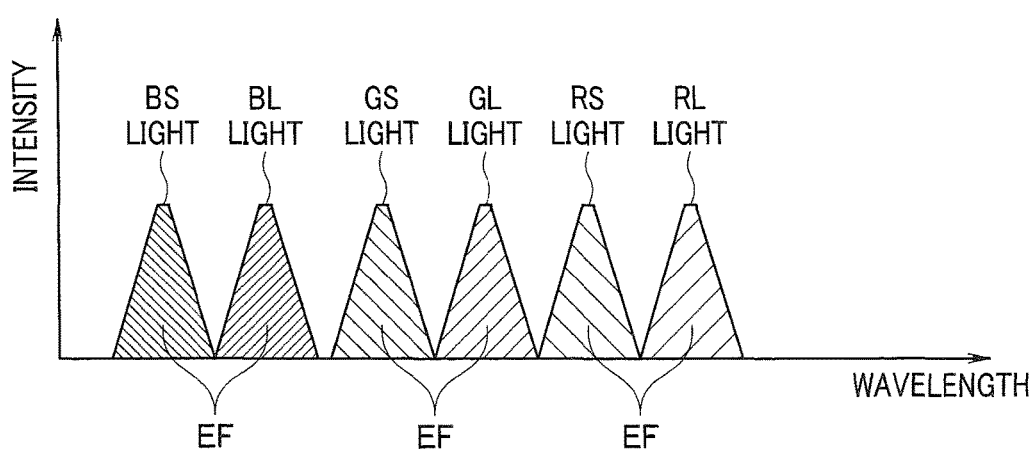
FIG. 23 is a diagram for describing one example of the illumination light supplied from the light source device in a modification of the first embodiment.

Then, according to the operations of the control portion 47 and the light source control portion 31 as described above, in the illumination period PA of the illumination pattern IP1, for example, as illustrated in FIG. 23, the illumination light including the BS light emitted by the emission light quantity EF and the BL light emitted by the emission light quantity EF is supplied from the light source device 3, return light LG including the BS light and the BL light is emitted from the object illuminated by the illumination light, and image data ILG obtained by picking up the image of the return light LG is outputted from the A/D conversion portion 42 to the WB processing portion 43.

In addition, according to the operations of the control portion 47 and the light source control portion 31 as described above, in the illumination period PB of the illumination pattern IP1, for example, as illustrated in FIG. 23, the illumination light including the GS light emitted by the emission light quantity EF and the GL light emitted by the emission light quantity EF is supplied from the light source device 3, return light LH including the GS light and the GL light is emitted from the object illuminated by the illumination light, and image data ILH obtained by picking up the image of the return light LH is outputted from the A/D conversion portion 42 to the WB processing portion 43.

In addition, according to the operations of the control portion 47 and the light source control portion 31 as described above, in the illumination period PC of the illumination pattern IP1, for example, as illustrated in FIG. 23, the illumination light including the RS light emitted by the emission light quantity EF and the RL light emitted by the emission light quantity EF is supplied from the light source device 3, return light LI including the RS light and the RL light is emitted from the object illuminated by the illumination light, and image data ILI obtained by picking up the image of the return light LI is outputted from the A/D conversion portion 42 to the WB processing portion 43.

The control portion 47 performs the control for causing the white balance processing using the predetermined white balance coefficient to be performed to each image data successively outputted from the A/D conversion portion 42 to the WB processing portion 43.

When detecting that the sharpness "off" is selected in the sharpness emphasizing switch, for example, the control portion 47 reads the spatial filter SFA designed to have the filter characteristic as illustrated in FIG. 3 from the memory 47a, and performs the control for causing the spatial filter processing using the read spatial filter SFA to be performed to the sharpness emphasizing portion 44.

The sharpness emphasizing portion 44 executes the spatial filter processing using the spatial filter SFA to each of the image data ILG, ILH and ILI outputted from the WB processing portion 43 when the sharpness "off" is selected in the sharpness emphasizing switch according to the control of the control portion 47, and outputs the image data to which the spatial filter processing is executed to the gradation conversion portion 45.

When detecting that the contrast "normal" is selected in the contrast emphasizing switch, for example, the control portion 47 reads the gradation conversion function TFA having the input/output characteristic as illustrated in FIG. 4 from the memory 47a, and performs the control for causing the gradation conversion processing using the read gradation conversion function TFA to be performed to each image data successively outputted from the sharpness emphasizing portion 44 to the gradation conversion portion 45. Note that the input/output characteristic in FIG. 4 is illustrated as the characteristic of increasing a luminance value of the entire image data area, compared to the case of not performing the gradation conversion processing (the case illustrated by a dotted line in FIG. 4).

The gradation conversion portion 45 executes the gradation conversion processing using the gradation conversion function TFA to each of the image data ILG, ILH and ILI outputted from the sharpness emphasizing portion 44 when the contrast "normal" is selected in the contrast emphasizing switch according to the control of the control portion 47, and outputs the image data to which the gradation conversion processing is executed to the display control portion 46.

The control portion 47 performs the control for making the image data ILG outputted from the gradation conversion portion 45 be allocated to the B channel of the display device 5, making the image data ILH outputted from the gradation conversion portion 45 be allocated to the G channel of the display device 5, and making the image data ILI outputted from the gradation conversion portion 45 be allocated to the R channel of the display device 5 to the display control portion 46.

Then, according to the operation of the control portion 47 or the like as described above, when the contrast "normal" is selected in the contrast emphasizing switch, the observation image in which the structure included in the biological tissue can be observed with the visibility almost equal to the visibility in the natural state that the emphasizing processing is not applied is displayed at the display device 5.

On the other hand, when detecting that contrast "high" which is the contrast higher than "normal" is selected in the contrast emphasizing switch, for example, the control portion 47 generates the emission light quantity ratio control signal for setting the emission light quantity of the blue light source 32a, the green light source 32d and the red light source 32e to an emission light quantity EG larger than the emission light quantity EF, and setting the emission light quantity of the blue light source 32b, the green light source 32c and the red light source 32f to an emission light quantity EH smaller than the emission light quantity EF, and outputs the signal to the light source control portion 31. Note that, when setting the emission light quantity at the contrast "high", the control portion 47 performs the adjustment for equalizing the value obtained by adding the emission light quantity EF of the two light sources of the same color (doubling the emission light quantity EF) at the contrast "normal" and the value obtained by adding the emission light quantities EG and EH of the two light sources of the same color.

The light source control portion 31 generates and outputs the light source drive signal for making the blue light source 32a, the green light source 32d and the red light source 32e emit the light by the emission light quantity EG, and making the blue light source 32b, the green light source 32c and the red light source 32f emit the light by the emission light quantity EH, when the contrast "high" is selected in the contrast emphasizing switch, according to the emission light quantity ratio control signal outputted from the control portion 47.

Figure 24:
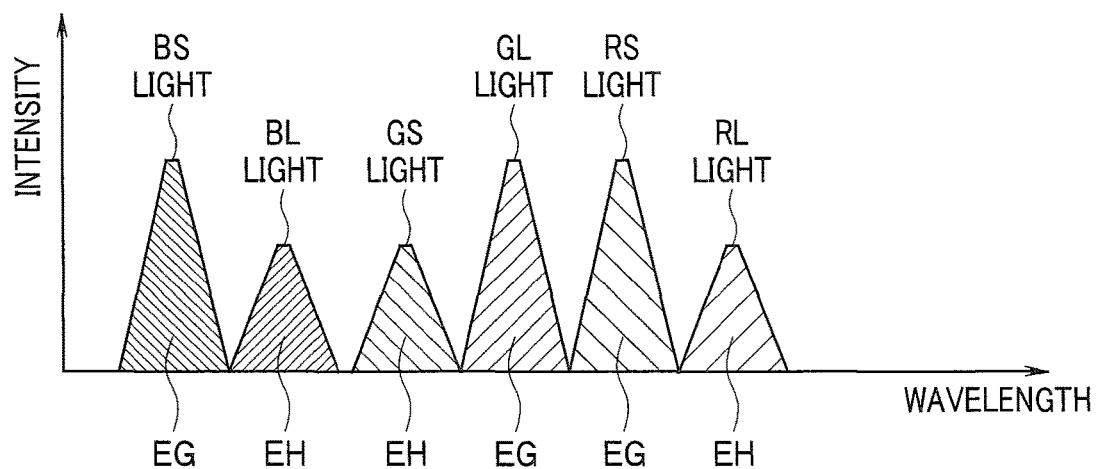
FIG. 24 is a diagram for describing one example of the illumination light supplied from the light source device in the modification of the first embodiment.

Then, according to the operations of the control portion 47 and the light source control portion 31 as described above, in the illumination period PA of the illumination pattern IP1, for example, as illustrated in FIG. 24, the illumination light including the BS light emitted by the emission light quantity EG and the BL light emitted by the emission light quantity EH is supplied from the light source device 3, return light LJ including the BS light and the BL light is emitted from the object illuminated by the illumination light, and image data ILJ obtained by picking up the image of the return light LJ is outputted from the A/D conversion portion 42 to the WB processing portion 43.

In addition, according to the operations of the control portion 47 and the light source control portion 31 as described above, in the illumination period PB of the illumination pattern IP1, for example, as illustrated in FIG. 24, the illumination light including the GS light emitted by the emission light quantity EH and the GL light emitted by the emission light quantity EG is supplied from the light source device 3, return light LK including the GS light and the GL light is emitted from the object illuminated by the illumination light, and image data ILK obtained by picking up the image of the return light LK is outputted from the A/D conversion portion 42 to the WB processing portion 43.

In addition, according to the operations of the control portion 47 and the light source control portion 31 as described above, in the illumination period PC of the illumination pattern IP1, for example, as illustrated in FIG. 24, the illumination light including the RS light emitted by the emission light quantity EG and the RL light emitted by the emission light quantity EH is supplied from the light source device 3, return light LL including the RS light and the RL light is emitted from the object illuminated by the illumination light, and image data ILL obtained by picking up the image of the return light LL is outputted from the A/D conversion portion 42 to the WB processing portion 43.

Figure 25:
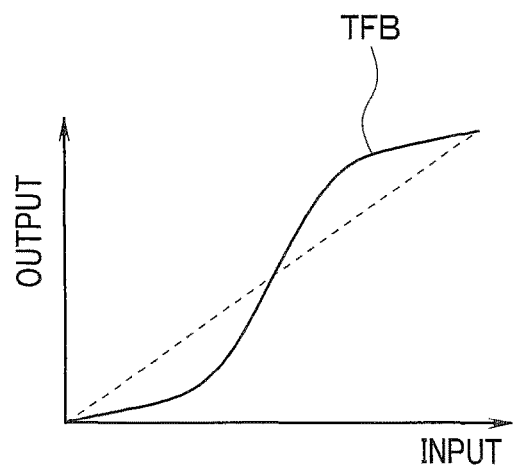
FIG. 25 is a diagram illustrating one example of the gradation conversion function used in the gradation conversion processing in the modification of the first embodiment.

When detecting that the contrast "high" is selected in the contrast emphasizing switch, for example, the control portion 47 reads a gradation conversion function TFB having the input/output characteristic as illustrated in FIG. 25 from the memory 47a, and performs the control for causing the gradation conversion processing using the read gradation conversion function TFB to be performed to each image data successively outputted from the sharpness emphasizing portion 44 to the gradation conversion portion 45. Note that the input/output characteristic in FIG. 25 is illustrated as the characteristic of reducing the luminance value of a dark area within the image data and increasing the luminance value of a bright area within the image data, compared to the case of not performing the gradation conversion processing (the case illustrated by the dotted line in FIG. 25).

The gradation conversion portion 45 executes the gradation conversion processing using the gradation conversion function TFB to each of the image data ILJ, ILK and ILL outputted from the sharpness emphasizing portion 44 when the contrast "high" is selected in the contrast emphasizing switch according to the control of the control portion 47, and outputs the image data to which the gradation conversion processing is executed to the display control portion 46.

The control portion 47 performs the control for making the image data ILJ outputted from the gradation conversion portion 45 be allocated to the B channel of the display device 5, making the image data ILK outputted from the gradation conversion portion 45 be allocated to the G channel of the display device 5, and making the image data ILL outputted from the gradation conversion portion 45 be allocated to the R channel of the display device 5 to the display control portion 46.

Then, according to the operation of the control portion 47 or the like as described above, when the contrast "high" is selected in the contrast emphasizing switch, the observation image in which the blood vessel of the large diameter existing in the deep layer of the biological tissue of the observation target, the blood vessel existing in the middle layer of the biological tissue of the observation target, and the capillary and the mucosal structure existing in the surface layer of the biological tissue of the observation target are respectively emphasized is displayed at the display device 5. In other words, according to the operation of the control portion 47 or the like as described above, when the contrast "high" is selected in the contrast emphasizing switch, the observation image in which the visibility of the blood vessel of the large diameter existing in the deep layer of the biological tissue of the observation target, the blood vessel existing in the middle layer of the biological tissue of the observation target, and the capillary and the mucosal structure existing in the surface layer of the biological tissue of the observation target is improved respectively more than the visibility at the contrast "normal" is displayed at the display device 5.

Here, for example, in the case of considering the situation of performing the gradation conversion processing for highlighting the structure such as the blood vessel included in the biological tissue according to a level of the contrast selected in the contrast emphasizing switch while the emission light quantity ratio of the respective light sources of the light source unit 32 is fixed at the constant ratio as in FIG. 23, since the gradation conversion processing needs to be performed using the gradation conversion function having a relatively steep input/output characteristic depending on the selected level of the contrast, the problem that the artifact such as gradation collapse is highly frequently generated arises.

In contrast, in the present embodiment, the emission light quantity ratio of the respective light sources of the light source unit 32 and the gradation conversion function used in the gradation conversion processing in the gradation conversion portion 45 are changed together according to the level of the contrast selected in the contrast emphasizing switch so that the structure such as the blood vessel included in the biological tissue can be sufficiently highlighted even in the case that the gradation conversion processing is performed using the gradation conversion function having a relatively gentle input/output characteristic (such as the gradation conversion function TFB). Therefore, according to the present embodiment, the generation frequency of the artifact such as the gradation collapse due to the gradation conversion processing for highlighting the structure such as the blood vessel included in the biological tissue can be suppressed to a low frequency, that is, the decline of the image quality which occurs according to the emphasis degree when highlighting the structure can be suppressed.

In addition, according to the present embodiment, the emission light quantities in the respective light sources of the light source unit 32 are adjusted according to the level of the contrast selected in the contrast emphasizing switch so that the fluctuation of the brightness and/or the color tone of the observation image which can occur accompanying the changeover of the level of the contrast in the contrast emphasizing switch can be suppressed as much as possible.

Note that, by appropriately modifying the configuration or the like relating to the modification described above, the almost similar operation effects can be obtained even in the case of illuminating the object by the illumination pattern of making the blue light sources 32a and 32b, the green light sources 32c and 32d and the red light sources 32e and 32f simultaneously emit the light, for example.

(Second Embodiment)

FIG. 26 to FIG. 31 relate to the second embodiment of the present invention.

Note that, in the present embodiment, detailed descriptions related to parts including components or the like similar to the components in the first embodiment are omitted, and parts including the components or the like different from the components in the first embodiment will be mainly described.

Figure 26:
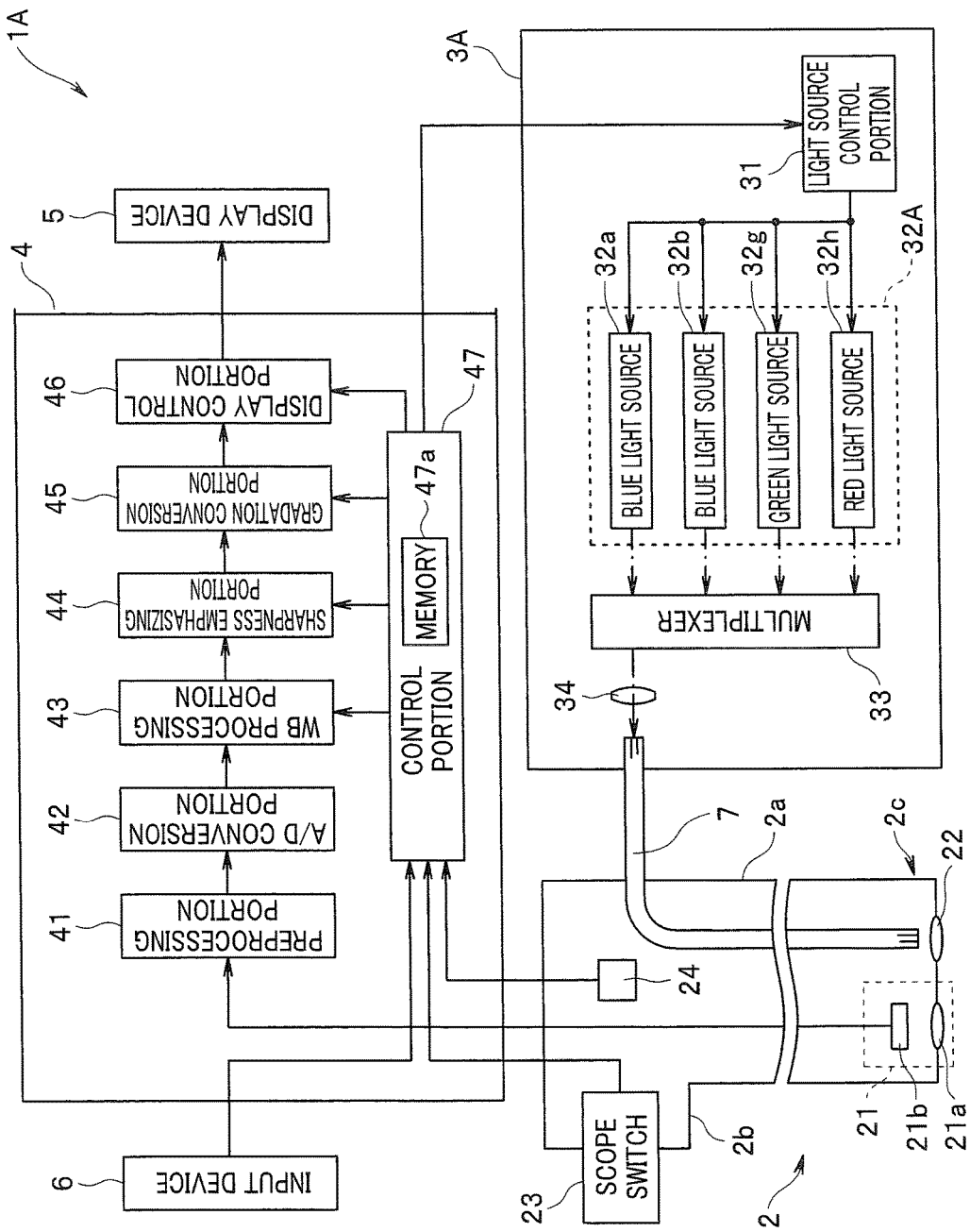
FIG. 26 is a diagram illustrating a configuration of the main part of the observation system relating to a second embodiment.

An observation system 1A is configured including a light source device 3A instead of the light source device 3 of the observation system 1, as illustrated in FIG. 26. FIG. 26 is a diagram illustrating the configuration of the main part of the observation system relating to the second embodiment.

The light source device 3A is configured including a light source unit 32A instead of the light source unit 32 of the light source device 3.

The light source unit 32A is configured including the blue light sources 32a and 32b, a green light source 32g, and a red light source 32h.

The green light source 32g is provided with a blue semiconductor laser and a green fluorescent material for example, and is configured to emit G light which is the green light including the wavelength from 500 nm to 580 nm. Note that the emission light quantity of the green light source 32g is assumed to be stipulated as the total light quantity obtained by integrating the intensity of the light of the respective wavelengths included in the wavelength band of the G light.

The red light source 32h is provided with a near ultraviolet semiconductor laser and a red fluorescent material for example, and is configured to emit R light which is the red light including the wavelength from 590 nm to 700 nm. Note that the emission light quantity of the red light source 32h is assumed to be stipulated as the total light quantity obtained by integrating the intensity of the light of the respective wavelengths included in the wavelength band of the R light.

Subsequently, specific operations or the like of the observation system 1A relating to the present embodiment will be described below. Note that, hereinafter, for simplification, the case that the contrast "normal" is selected in the contrast emphasizing switch will be described as an example.

First, a user connects the respective portions of the observation system 1A, supplies the power, then performs the operation of switching the illumination switch (not shown in the figure) provided in the scope switch 23 and/or the input device 6 from off to on, for example, and thus gives the instruction for causing the illumination light to be supplied from the light source device 3A to the endoscope 2 to the control portion 47. In addition, the user gives the instruction for not highlighting the structure included in the biological tissue to the control portion 47 by performing the operation of selecting the sharpness "off" in the sharpness emphasizing switch provided in the scope switch 23 and/or the input device 6, for example.

When detecting that the power source of the processor 4 is turned on and the illumination switch is turned on, the control portion 47 generates the illumination control signal for illuminating the object by a time division illumination pattern IP2, and outputs the signal to the light source control portion 31. Specifically, when detecting that the power source of the processor 4 is turned on and the illumination switch is turned on, the control portion 47 generates the illumination control signal for illuminating the object by the illumination pattern IP2 of cyclically repeating an illumination period PD of making the blue light sources 32a and 32b simultaneously emit the light, an illumination period PE of making the green light source 32g emit the light and an illumination period PF of making the red light source 32h emit the light in the order for example, and outputs the signal to the light source control portion 31. Note that the order of the respective illumination periods in the illumination pattern IP2 may not be the order of PD→PE→PF.

In addition, when detecting that the sharpness "off" is selected in the sharpness emphasizing switch, for example, the control portion 47 generates the emission light quantity ratio control signal for setting the emission light quantity of the blue light sources 32a and 32b to a mutually same emission light quantity EI, setting the emission light quantity of the green light source 32g to an emission light quantity EJ, and setting the emission light quantity of the red light source 32h to an emission light quantity EK, and outputs the signal to the light source control portion 31.

The light source control portion 31 generates and outputs the light source drive signal for making the blue light sources 32a and 32b simultaneously emit the light while making the green light source 32g and the red light source 32h quench the light in the illumination period PD, making the green light source 32g emit the light while making the blue light source 32a, the blue light source 32b and the red light source 32h quench the light in the illumination period PE, and making the red light source 32h emit the light while making the blue light source 32a, the blue light source 32b and the green light source 32g quench the light in the illumination period PF, according to the illumination control signal outputted from the control portion 47.

In addition, the light source control portion 31 generates and outputs the light source drive signal for making the blue light sources 32a and 32b emit the light by the emission light quantity EI, making the green light source 32g emit the light by the emission light quantity EJ, and making the red light source 32h emit the light by the emission light quantity EK, when the sharpness "off" is selected in the sharpness emphasizing switch, according to the emission light quantity ratio control signal outputted from the control portion 47.

Figure 27:
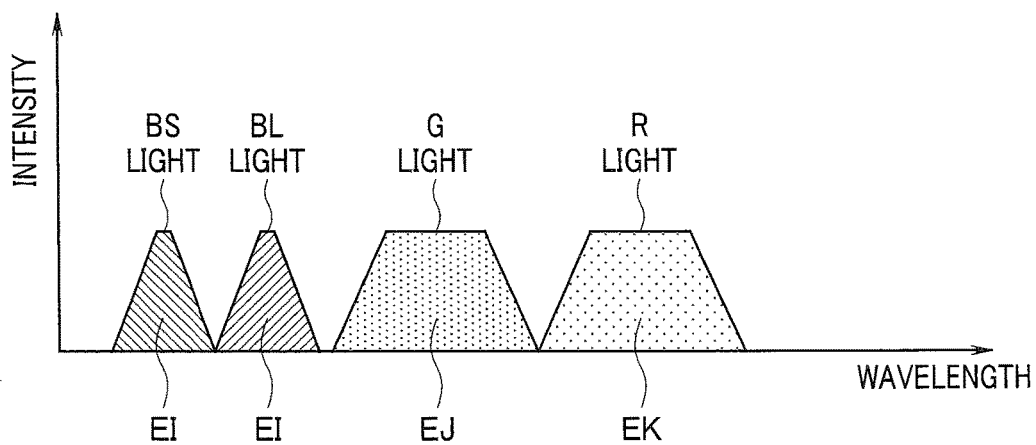
FIG. 27 is a diagram for describing one example of the illumination light supplied from the light source device in the second embodiment.

Then, according to the operations of the control portion 47 and the light source control portion 31 as described above, in the illumination period PD of the illumination pattern IP2, for example, as illustrated in FIG. 27, the illumination light including the BS light emitted by the emission light quantity EI and the BL light emitted by the emission light quantity EI is supplied from the light source device 3A, return light LM including the BS light and the BL light is emitted from the object illuminated by the illumination light, and image data ILM obtained by picking up the image of the return light LM is outputted from the A/D conversion portion 42 to the WB processing portion 43.

In addition, according to the operations of the control portion 47 and the light source control portion 31 as described above, in the illumination period PE of the illumination pattern IP2, for example, as illustrated in FIG. 27, the G light emitted by the emission light quantity EJ is supplied from the light source device 3A as the illumination light, return light LN according to the G light is emitted from the object illuminated by the illumination light, and image data ILN obtained by picking up the image of the return light LN is outputted from the A/D conversion portion 42 to the WB processing portion 43.

In addition, according to the operations of the control portion 47 and the light source control portion 31 as described above, in the illumination period PF of the illumination pattern IP2, for example, as illustrated in FIG. 27, the R light emitted by the emission light quantity EK is supplied from the light source device 3A as the illumination light, return light LO according to the R light is emitted from the object illuminated by the illumination light, and image data ILO obtained by picking up the image of the return light LO is outputted from the A/D conversion portion 42 to the WB processing portion 43.

When detecting that the sharpness "off" is selected in the sharpness emphasizing switch, the control portion 47 performs the control for causing the white balance processing applying a white balance coefficient WBA to the image data ILM, applying a white balance coefficient WGA to the image data ILN, and applying a white balance coefficient WRA to the image data ILO to be performed to the WB processing portion 43. Note that the white balance coefficients WBA, WGA and WRA are assumed to be stored beforehand in the memory 47a as the values that turn a luminance ratio of the image data ILM, ILN and ILO obtained by picking up the image of the white reference object illuminated by the illumination light of the emission light quantity as illustrated in FIGS. 27 to 1:1:1, for example.

The WB processing portion 43 multiplies the luminance value of each pixel included in the image data ILM outputted from the A/D conversion portion 42 by the white balance coefficient WBA and outputs the luminance value to the sharpness emphasizing portion 44, according to the control of the control portion 47. In addition, the WB processing portion 43 multiplies the luminance value of each pixel included in the image data ILN outputted from the A/D conversion portion 42 by the white balance coefficient WGA and outputs the luminance value to the sharpness emphasizing portion 44, according to the control of the control portion 47. Furthermore, the WB processing portion 43 multiplies the luminance value of each pixel included in the image data ILO outputted from the A/D conversion portion 42 by the white balance coefficient WRA and outputs the luminance value to the sharpness emphasizing portion 44, according to the control of the control portion 47.

When detecting that the sharpness "off" is selected in the sharpness emphasizing switch, for example, the control portion 47 reads the spatial filter SFA designed to have the filter characteristic as illustrated in FIG. 3 for example from the memory 47a, and performs the control for causing the spatial filter processing using the read spatial filter SFA to be performed to the sharpness emphasizing portion 44.

The sharpness emphasizing portion 44 executes the spatial filter processing using the spatial filter SFA to each of the image data ILM, ILN and ILO outputted from the WB processing portion 43 when the sharpness "off" is selected in the sharpness emphasizing switch according to the control of the control portion 47, and outputs the image data to which the spatial filter processing is executed to the gradation conversion portion 45.

When detecting that the contrast "normal" is selected in the contrast emphasizing switch, for example, the control portion 47 reads the gradation conversion function TFA having the input/output characteristic as illustrated in FIG. 4 from the memory 47a, and performs the control for causing the gradation conversion processing using the read gradation conversion function TFA to be performed to each image data successively outputted from the sharpness emphasizing portion 44 to the gradation conversion portion 45.

The control portion 47 performs the control for making the image data ILM outputted from the gradation conversion portion 45 be allocated to the B channel of the display device 5, making the image data ILN outputted from the gradation conversion portion 45 be allocated to the G channel of the display device 5, and making the image data ILO outputted from the gradation conversion portion 45 be allocated to the R channel of the display device 5 to the display control portion 46.

Then, according to the operation of the control portion 47 or the like as described above, when the sharpness "off" is selected in the sharpness emphasizing switch, the observation image in which the structure included in the biological tissue can be observed with the visibility almost equal to the visibility in the natural state that the emphasizing processing is not applied is displayed at the display device 5.

On the other hand, the user arranges the distal end portion 2c at the position at which the image of the biological tissue of the observation target existing inside the subject can be picked up, by inserting the insertion portion 2a of the endoscope 2 into the subject. Then, for example, by appropriately selecting the sharpness in the sharpness emphasizing switch according to the observation distance between the distal end portion 2c and the biological tissue of the observation target, the user gives the instruction for highlighting the capillary and the mucosal structure existing in the surface layer of the biological tissue of the observation target at the desired emphasis degree to the control portion 47.

Specifically, for example, in the case that the observation distance between the distal end portion 2c and the biological tissue of the observation target belongs to the distant view, by performing the operation of selecting the sharpness "weak" in the sharpness emphasizing switch, the user gives the instruction for causing highlighting to be performed at such an emphasis degree that the capillary and the mucosal structure existing in the surface layer of the biological tissue of the observation target become easy to view compared to the capillary and the mucosal structure at the sharpness "off" to the control portion 47.

When detecting that the sharpness "weak" is selected in the sharpness emphasizing switch, for example, the control portion 47 generates the emission light quantity ratio control signal for setting the emission light quantity of the blue light sources 32a and 32b to an emission light quantity EL larger than the emission light quantity EI, setting the emission light quantity of the green light source 32g to an emission light quantity EM larger than the emission light quantity EJ, and setting the emission light quantity of the red light source 32h to an emission light quantity EN smaller than the emission light quantity EK, and outputs the signal to the light source control portion 31. Note that, when setting the emission light quantity at the sharpness "weak", the control portion 47 performs the adjustment for satisfying a relational equation indicated in a following numerical equation (1).

$$EI+EI+EJ+EK=EL+EL+EM+EN \quad (1)$$

The light source control portion 31 generates and outputs the light source drive signal for making the blue light sources 32a and 32b emit the light by the emission light quantity EL, making the green light source 32g emit the light by the emission light quantity EM, and making the red light source 32h emit the light by the emission light quantity EN, when the sharpness "weak" is selected in the sharpness emphasizing switch, according to the emission light quantity ratio control signal outputted from the control portion 47.

Figure 28:
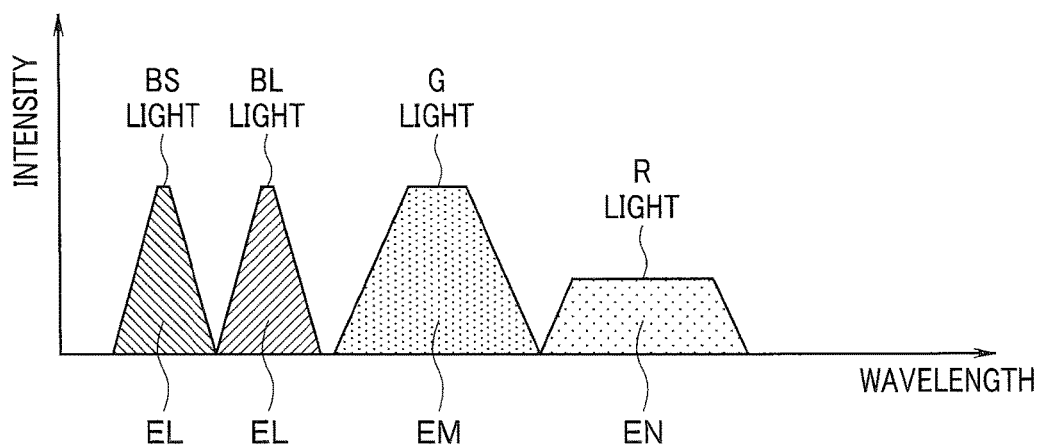
FIG. 28 is a diagram for describing one example of the illumination light supplied from the light source device in the second embodiment.

Then, according to the operations of the control portion 47 and the light source control portion 31 as described above, in the illumination period PD of the illumination pattern IP2, for example, as illustrated in FIG. 28, the illumination light including the BS light emitted by the emission light quantity EL and the BL light emitted by the emission light quantity EL is supplied from the light source device 3A, return light LP including the BS light and the BL light is emitted from the object illuminated by the illumination light, and image data ILP obtained by picking up the image of the return light LP is outputted from the A/D conversion portion 42 to the WB processing portion 43.

In addition, according to the operations of the control portion 47 and the light source control portion 31 as described above, in the illumination period PE of the illumination pattern IP2, for example, as illustrated in FIG. 28, the G light emitted by the emission light quantity EM is supplied from the light source device 3A as the illumination light, return light LQ according to the G light is emitted from the object illuminated by the illumination light, and image data ILQ obtained by picking up the image of the return light LQ is outputted from the A/D conversion portion 42 to the WB processing portion 43.

In addition, according to the operations of the control portion 47 and the light source control portion 31 as described above, in the illumination period PF of the illumination pattern IP2, for example, as illustrated in FIG. 28, the R light emitted by the emission light quantity EN is supplied from the light source device 3A as the illumination light, return light LR according to the R light is emitted from the object illuminated by the illumination light, and image data ILR obtained by picking up the image of the return light LR is outputted from the A/D conversion portion 42 to the WB processing portion 43.

When detecting that the sharpness "weak" is selected in the sharpness emphasizing switch, the control portion 47 performs the control for causing the white balance processing applying a white balance coefficient WBB to the image data ILP, applying a white balance coefficient WGB to the image data ILQ, and applying a white balance coefficient WRB to the image data ILR to be performed to the WB processing portion 43. Note that the white balance coefficients WBB, WGB and WRB are assumed to be calculated beforehand as the values for which the white balance coefficients WBA, WGA and WRA at the sharpness "off" are respectively multiplied by the value of the emission light quantity ratio obtained by dividing the emission light quantity at the sharpness "off" by the emission light quantity at the sharpness "weak", as indicated in following numerical equations (2) to (4), for example.

$$WBB=WBA\times(EI+EI)/(EL+EL)=WBA\times(EI/EL) \quad (2)$$

$$WGB=WGA\times(EJ/EM) \quad (3)$$

$$WRB=WRA\times(EK/EN) \quad (4)$$

The WB processing portion 43 multiplies the luminance value of each pixel included in the image data ILP outputted from the A/D conversion portion 42 by the white balance coefficient WBB and outputs the luminance value to the sharpness emphasizing portion 44, when the sharpness "weak" is selected in the sharpness emphasizing switch according to the control of the control portion 47. In addition, the WB processing portion 43 multiplies the luminance value of each pixel included in the image data ILQ outputted from the A/D conversion portion 42 by the white balance coefficient WGB and outputs the luminance value to the sharpness emphasizing portion 44, when the sharpness "weak" is selected in the sharpness emphasizing switch according to the control of the control portion 47. Furthermore, the WB processing portion 43 multiplies the luminance value of each pixel included in the image data ILR outputted from the A/D conversion portion 42 by the white balance coefficient WRB and outputs the luminance value to the sharpness emphasizing portion 44, when the sharpness "weak" is selected in the sharpness emphasizing switch according to the control of the control portion 47.

When detecting that the sharpness "weak" is selected in the sharpness emphasizing switch, for example, the control portion 47 reads the spatial filter SFB designed to have the filter characteristic as illustrated in FIG. 6 from the memory 47a, and performs the control for causing the spatial filter processing using the read spatial filter SFB to be performed to the sharpness emphasizing portion 44.

The sharpness emphasizing portion 44 executes the spatial filter processing using the spatial filter SFB to each of the image data ILP, ILQ and ILR outputted from the WB processing portion 43 when the sharpness "weak" is selected in the sharpness emphasizing switch according to the control of the control portion 47, and outputs the image data to which the spatial filter processing is executed to the gradation conversion portion 45.

The control portion 47 performs the control for making the image data ILP outputted from the gradation conversion portion 45 be allocated to the B channel of the display device 5, making the image data ILQ outputted from the gradation conversion portion 45 be allocated to the G channel of the display device 5, and making the image data ILR outputted from the gradation conversion portion 45 be allocated to the R channel of the display device 5 to the display control portion 46.

Then, according to the operation of the control portion 47 or the like as described above, when the sharpness "weak" is selected in the sharpness emphasizing switch, the observation image in which the blood vessel existing in the middle layer of the biological tissue of the observation target and the capillary and the mucosal structure existing in the surface layer of the biological tissue are respectively emphasized compared to the blood vessel and the capillary and the mucosal structure at the sharpness "off" is displayed at the display device 5. In other words, according to the operation of the control portion 47 or the like as described above, when the sharpness "weak" is selected in the sharpness emphasizing switch, the observation image in which the visibility of the blood vessel existing in the middle layer of the biological tissue of the observation target and the capillary and the mucosal structure existing in the surface layer of the biological tissue is improved more than the visibility at the sharpness "off" is displayed at the display device 5.

On the other hand, for example, in the case that the observation distance between the distal end portion 2c and the biological tissue of the observation target belongs to the intermediate view, by performing the operation of selecting the sharpness "middle" in the sharpness emphasizing switch, the user gives the instruction for causing highlighting to be performed at such an emphasis degree that the capillary and the mucosal structure existing in the surface layer of the biological tissue of the observation target become easy to view compared to the capillary and the mucosal structure at the sharpness "weak" to the control portion 47.

When detecting that the sharpness "middle" is selected in the sharpness emphasizing switch, for example, the control portion 47 generates the emission light quantity ratio control signal for setting the emission light quantity of the blue light sources 32a and 32b to an emission light quantity EO larger than the emission light quantity EL, setting the emission light quantity of the green light source 32g to the emission light quantity EJ, and setting the emission light quantity of the red light source 32h to the emission light quantity EN, and outputs the signal to the light source control portion 31. Note that, when setting the emission light quantity at the sharpness "middle", the control portion 47 performs the adjustment for satisfying the relational equation indicated in a following numerical equation (5).

$$EL+EL+EM+EN=EO+EO+EJ+EN \tag{5}$$

The light source control portion 31 generates and outputs the light source drive signal for making the blue light sources 32a and 32b emit the light by the emission light quantity EO, making the green light source 32g emit the light by the emission light quantity EJ, and making the red light source 32h emit the light by the emission light quantity EN, when the sharpness "middle" is selected in the sharpness emphasizing switch, according to the emission light quantity ratio control signal outputted from the control portion 47.

Figure 29:
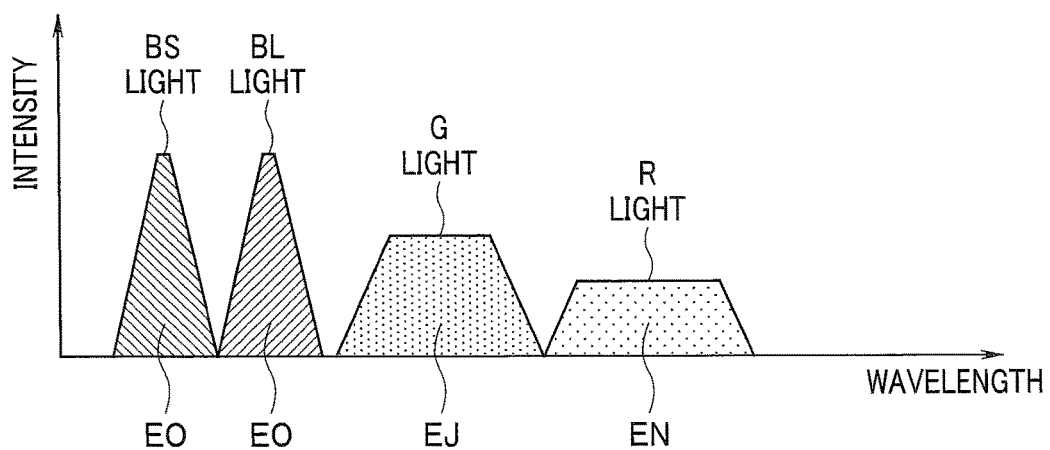
FIG. 29 is a diagram for describing one example of the illumination light supplied from the light source device in the second embodiment.

Then, according to the operations of the control portion 47 and the light source control portion 31 as described above, in the illumination period PD of the illumination pattern IP2, for example, as illustrated in FIG. 29, the illumination light including the BS light emitted by the emission light quantity EO and the BL light emitted by the emission light quantity EO is supplied from the light source device 3A, return light LS including the BS light and the BL light is emitted from the object illuminated by the illumination light, and image data ILS obtained by picking up the image of the return light LS is outputted from the A/D conversion portion 42 to the WB processing portion 43.

In addition, according to the operations of the control portion 47 and the light source control portion 31 as described above, in the illumination period PE of the illumination pattern IP2, for example, as illustrated in FIG. 29, the G light emitted by the emission light quantity EJ is supplied from the light source device 3A as the illumination light, the return light LN according to the G light is emitted from the object illuminated by the illumination light, and the image data ILN obtained by picking up the image of the return light LN is outputted from the A/D conversion portion 42 to the WB processing portion 43.

In addition, according to the operations of the control portion 47 and the light source control portion 31 as described above, in the illumination period PF of the illumination pattern IP2, for example, as illustrated in FIG. 29, the R light emitted by the emission light quantity EN is supplied from the light source device 3A as the illumination light, the return light LR according to the R light is emitted from the object illuminated by the illumination light, and the image data ILR obtained by picking up the image of the return light LR is outputted from the A/D conversion portion 42 to the WB processing portion 43.

When detecting that the sharpness "middle" is selected in the sharpness emphasizing switch, the control portion 47 performs the control for causing the white balance processing applying a white balance coefficient WBC to the image data ILS, applying a white balance coefficient WGC to the image data ILN, and applying a white balance coefficient WRC to the image data ILR to be performed to the WB processing portion 43. Note that the white balance coefficients WBC, WGC and WRC are assumed to be calculated beforehand as the values for which the white balance coefficients WBA, WGA and WRA at the sharpness "off" are respectively multiplied by the value of the emission light quantity ratio obtained by dividing the emission light quantity at the sharpness "off" by the emission light quantity at the sharpness "middle", as indicated in following numerical equations (6) to (8), for example.

$$WBC=WBA\times(EI+EI)/(EO+EO)=WBA\times(EI/EO) \tag{6}$$

$$WGC=WGA\times(EJ/EJ)=WGA \tag{7}$$

$$WRC=WRA\times(EK/EN) \tag{8}$$

The WB processing portion 43 multiplies the luminance value of each pixel included in the image data ILS outputted from the A/D conversion portion 42 by the white balance coefficient WBC and outputs the luminance value to the sharpness emphasizing portion 44, when the sharpness "middle" is selected in the sharpness emphasizing switch according to the control of the control portion 47. In addition, the WB processing portion 43 multiplies the luminance value of each pixel included in the image data ILN outputted from the A/D conversion portion 42 by the white balance coefficient WGC and outputs the luminance value to the sharpness emphasizing portion 44, when the sharpness "middle" is selected in the sharpness emphasizing switch according to the control of the control portion 47. Furthermore, the WB processing portion 43 multiplies the luminance value of each pixel included in the image data ILR outputted from the A/D conversion portion 42 by the white balance coefficient WRC and outputs the luminance value to the sharpness emphasizing portion 44, when the sharpness "middle" is selected in the sharpness emphasizing switch according to the control of the control portion 47.

When detecting that the sharpness "middle" is selected in the sharpness emphasizing switch, for example, the control portion 47 reads the spatial filter SFC designed to have the filter characteristic as illustrated in FIG. 8 from the memory 47a, and performs the control for causing the spatial filter processing using the read spatial filter SFC to be performed to the sharpness emphasizing portion 44.

The sharpness emphasizing portion 44 executes the spatial filter processing using the spatial filter SFC to each of the image data ILS, ILN and ILR outputted from the WB processing portion 43 when the sharpness "middle" is selected in the sharpness emphasizing switch according to the control of the control portion 47, and outputs the image data to which the spatial filter processing is executed to the gradation conversion portion 45.

The control portion 47 performs the control for making the image data ILS outputted from the gradation conversion portion 45 be allocated to the B channel of the display device 5, making the image data ILN outputted from the gradation conversion portion 45 be allocated to the G channel of the display device 5, and making the image data ILR outputted from the gradation conversion portion 45 be allocated to the R channel of the display device 5 to the display control portion 46.

Then, according to the operation of the control portion 47 or the like as described above, when the sharpness "middle" is selected in the sharpness emphasizing switch, the observation image in which the capillary and the mucosal structure existing in the surface layer of the biological tissue are emphasized compared to the capillary and the mucosal structure at the sharpness "weak" is displayed at the display device 5. In other words, according to the operation of the control portion 47 or the like as described above, when the sharpness "middle" is selected in the sharpness emphasizing switch, the observation image in which the visibility of the capillary and the mucosal structure existing in the surface layer of the biological tissue of the observation target is improved more than the visibility at the sharpness "weak" is displayed at the display device 5.

On the other hand, for example, in the case that the observation distance between the distal end portion 2c and the biological tissue of the observation target belongs to the close view, by performing the operation of selecting the sharpness "strong" in the sharpness emphasizing switch, the user gives the instruction for causing highlighting to be performed at such an emphasis degree that the capillary and the mucosal structure existing in the surface layer of the biological tissue of the observation target become easy to view compared to the capillary and the mucosal structure at the sharpness "middle" to the control portion 47.

When detecting that the sharpness "strong" is selected in the sharpness emphasizing switch, for example, the control portion 47 generates the emission light quantity ratio control signal for setting the emission light quantity of the blue light source 32a to an emission light quantity EP larger than the emission light quantity EO, setting the emission light quantity of the blue light source 32b to the emission light quantity EL, setting the emission light quantity of the green light source 32g to the emission light quantity EJ, and setting the emission light quantity of the red light source 32h to the emission light quantity EN, and outputs the signal to the light source control portion 31. Note that, when setting the emission light quantity at the sharpness "strong", the control portion 47 performs the adjustment for satisfying the relational equation indicated in a following numerical equation (9).

$$EO+EO+EJ+EN=EP+EL+EJ+EN \qquad (9)$$

The light source control portion 31 generates and outputs the light source drive signal for making the blue light source 32a emit the light by the emission light quantity EP, making the blue light source 32b emit the light by the emission light quantity EL, making the green light source 32g emit the light by the emission light quantity EJ, and making the red light source 32h emit the light by the emission light quantity EN, when the sharpness "strong" is selected in the sharpness emphasizing switch, according to the emission light quantity ratio control signal outputted from the control portion 47.

Figure 30:
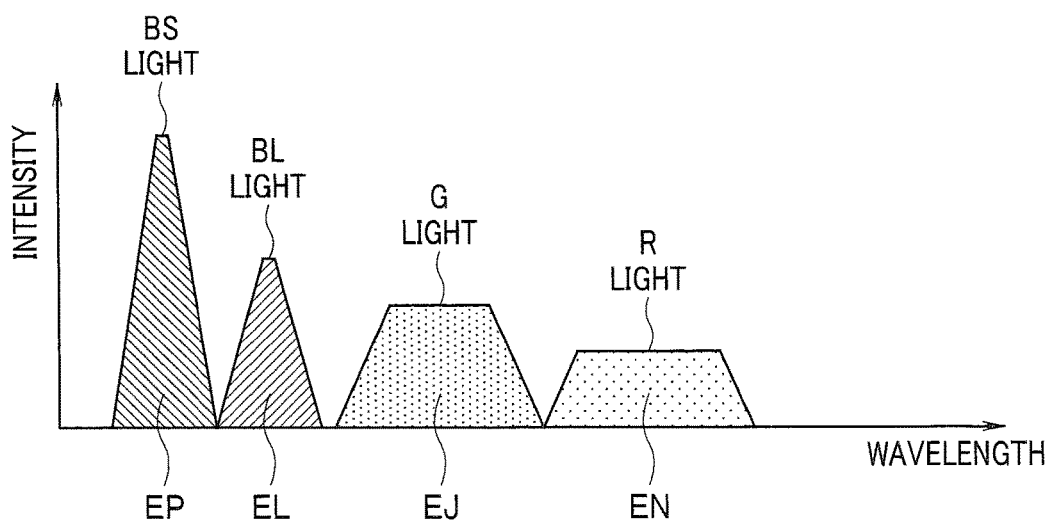
FIG. 30 is a diagram for describing one example of the illumination light supplied from the light source device in the second embodiment.

Then, according to the operations of the control portion 47 and the light source control portion 31 as described above, in the illumination period PD of the illumination pattern IP2, for example, as illustrated in FIG. 30, the illumination light including the BS light emitted by the emission light quantity EP and the BL light emitted by the emission light quantity EL is supplied from the light source device 3A, return light LT including the BS light and the BL light is emitted from the object illuminated by the illumination light, and image data ILT obtained by picking up the image of the return light LT is outputted from the A/D conversion portion 42 to the WB processing portion 43.

In addition, according to the operations of the control portion 47 and the light source control portion 31 as described above, in the illumination period PE of the illumination pattern IP2, for example, as illustrated in FIG. 30, the G light emitted by the emission light quantity EJ is supplied from the light source device 3A as the illumination light, the return light LN according to the G light is emitted from the object illuminated by the illumination light, and the image data ILN obtained by picking up the image of the return light LN is outputted from the A/D conversion portion 42 to the WB processing portion 43.

In addition, according to the operations of the control portion 47 and the light source control portion 31 as described above, in the illumination period PF of the illumination pattern IP2, for example, as illustrated in FIG. 30, the R light emitted by the emission light quantity EN is supplied from the light source device 3A as the illumination light, the return light LR according to the R light is emitted from the object illuminated by the illumination light, and the image data ILR obtained by picking up the image of the return light LR is outputted from the A/D conversion portion 42 to the WB processing portion 43.

When detecting that the sharpness "strong" is selected in the sharpness emphasizing switch, the control portion 47 performs the control for causing the white balance processing applying a white balance coefficient WBD to the image data ILT, applying a white balance coefficient WGD to the image data ILN, and applying a white balance coefficient WRD to the image data ILR to be performed to the WB processing portion 43. Note that the white balance coefficients WBD, WGD and WRD are assumed to be calculated beforehand as the values for which the white balance coefficients WBA, WGA and WRA at the sharpness "off" are respectively multiplied by the value of the emission light quantity ratio obtained by dividing the emission light quantity at the sharpness "off" by the emission light quantity at the sharpness "strong", as indicated in following numerical equations (10) to (12), for example.

$$WBD=WBA\times(EI+EI)/(EP+EL) \quad (10)$$

$$WGD=WGA\times(EJ/EJ)=WGA \quad (11)$$

$$WRD=WRA\times(EK/EN) \quad (12)$$

The WB processing portion 43 multiplies the luminance value of each pixel included in the image data ILT outputted from the A/D conversion portion 42 by the white balance coefficient WBD and outputs the luminance value to the sharpness emphasizing portion 44, when the sharpness "strong" is selected in the sharpness emphasizing switch according to the control of the control portion 47. In addition, the WB processing portion 43 multiplies the luminance value of each pixel included in the image data ILN outputted from the A/D conversion portion 42 by the white balance coefficient WGD and outputs the luminance value to the sharpness emphasizing portion 44, when the sharpness "strong" is selected in the sharpness emphasizing switch according to the control of the control portion 47. Furthermore, the WB processing portion 43 multiplies the luminance value of each pixel included in the image data ILR outputted from the A/D conversion portion 42 by the white balance coefficient WRD and outputs the luminance value to the sharpness emphasizing portion 44, when the sharpness "strong" is selected in the sharpness emphasizing switch according to the control of the control portion 47.

Figure 31:
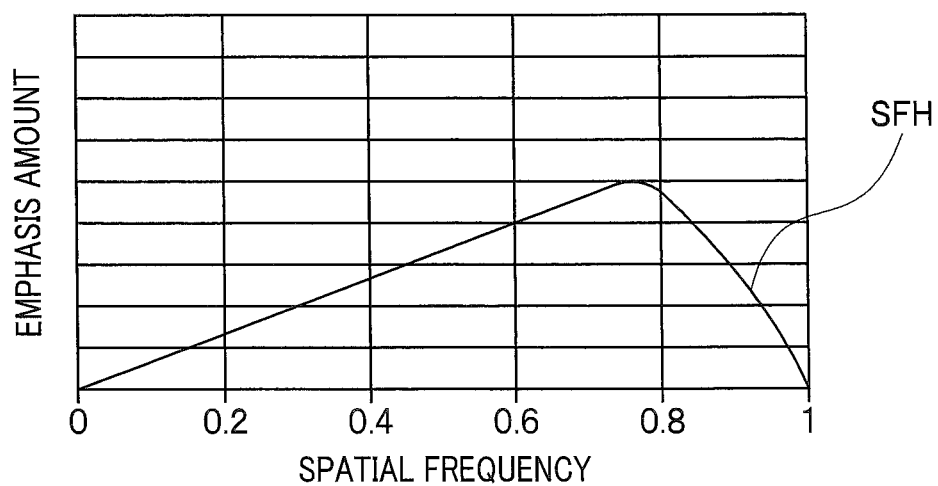
FIG. 31 is a diagram illustrating one example of the filter characteristic of the spatial filter used in the spatial filter processing in the second embodiment.

When detecting that the sharpness "strong" is selected in the sharpness emphasizing switch, for example, the control portion 47 reads a spatial filter SFH designed to have the filter characteristic as illustrated in FIG. 31 for example from the memory 47a, and performs the control for causing the spatial filter processing using the read spatial filter SFH to be performed to the sharpness emphasizing portion 44. Note that the filter characteristic in FIG. 31 is illustrated as the characteristic that the spatial frequency emphasized by the maximum emphasis amount is shifted to the high band side more than the spatial frequency of the spatial filter SFA and the emphasis amount at the spatial frequency of the middle band to the high band is equal to or larger than the emphasis amount of the spatial filter SFG (and SFA).

The sharpness emphasizing portion 44 executes the spatial filter processing using the spatial filter SFH to each of the image data ILT, ILN and ILR outputted from the WB processing portion 43 when the sharpness "strong" is selected in the sharpness emphasizing switch according to the control of the control portion 47, and outputs the image data to which the spatial filter processing is executed to the gradation conversion portion 45.

The control portion 47 performs the control for making the image data ILT outputted from the gradation conversion portion 45 be allocated to the B channel of the display device 5, making the image data ILN outputted from the gradation conversion portion 45 be allocated to the G channel of the display device 5, and making the image data ILR outputted from the gradation conversion portion 45 be allocated to the R channel of the display device 5 to the display control portion 46.

Then, according to the operation of the control portion 47 or the like as described above, when the sharpness "strong" is selected in the sharpness emphasizing switch, the observation image in which the capillary and the mucosal structure existing in the surface layer of the biological tissue are emphasized compared to the capillary and the mucosal structure at the sharpness "middle" is displayed at the display device 5. In other words, according to the operation of the control portion 47 or the like as described above, when the sharpness "strong" is selected in the sharpness emphasizing switch, the observation image in which the visibility of the capillary and the mucosal structure existing in the surface layer of the biological tissue of the observation target is improved more than the visibility at the sharpness "middle" is displayed at the display device 5.

According to the configuration and operations or the like of the present embodiment as described above, the generation frequency of the artifact such as the color noise due to the spatial filter processing for highlighting the structure such as the blood vessel included in the biological tissue can be suppressed to the low frequency, that is, the decline of the image quality which occurs according to the emphasis degree when highlighting the structure can be suppressed.

In addition, according to the present embodiment, the emission light quantities in the respective light sources of the light source unit 32A are adjusted according to the sharpness selected in the sharpness emphasizing switch so that the fluctuation of the brightness and/or the color tone of the observation image which can occur accompanying the changeover of the sharpness in the sharpness emphasizing switch can be suppressed as much as possible.

(Third Embodiment)

FIG. 32 to FIG. 36 relate to the third embodiment of the present invention.

Note that, in the present embodiment, the detailed descriptions related to parts including components or the like similar to the components in at least either one of the first and second embodiments are omitted, and parts including the components or the like different from the components in both of the first and second embodiments will be mainly described.

Figure 32:
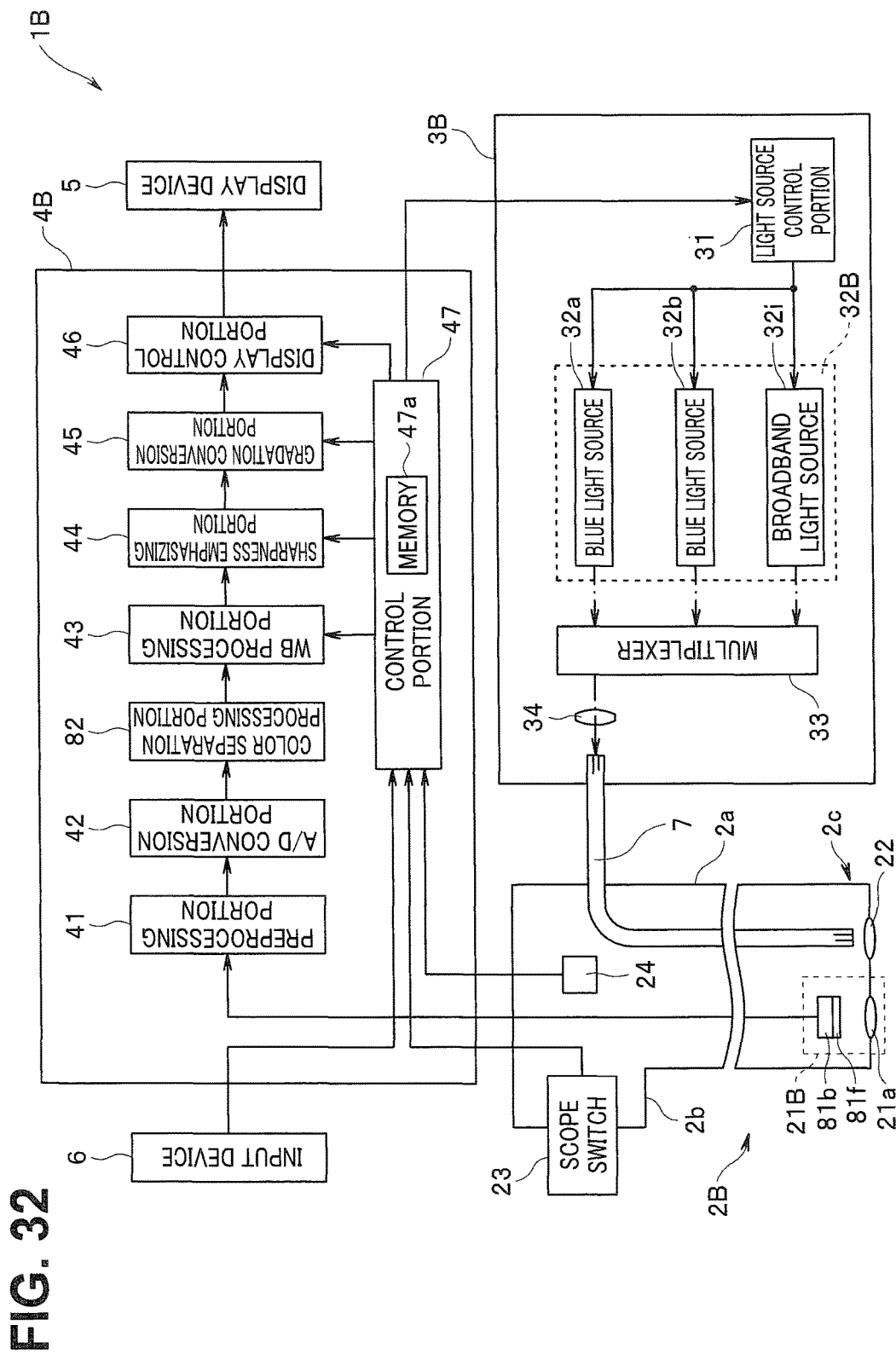
FIG. 32 is a diagram illustrating a configuration of the main part of the observation system relating to a third embodiment.

An observation system 1B is configured including an endoscope 2B instead of the endoscope 2 of the observation system 1, including a light source device 3B instead of the light source device 3 of the observation system 1, and including a processor 4B instead of the processor 4 of the observation system 1, as illustrated in FIG. 32. FIG. 32 is a diagram illustrating the configuration of the main part of the observation system relating to the third embodiment.

The endoscope 2B is configured including an image pickup portion 21B instead of the image pickup portion 21 of the endoscope 2.

The image pickup portion 21B is configured including an image pickup device 81b configured by disposing the plurality of pixels for receiving the return light emitted from the object and picking up the image in the matrix shape in accordance with the image forming position of the objective optical system 21a, and disposing a primary color filter 81f on a front surface of the plurality of pixels, instead of the image pickup device 21b of the image pickup portion 21.

The image pickup device 81b includes the image sensor such as a CCD or a CMOS for example, and is configured to generate the image pickup signal by picking up the image of the return light which has passed through the primary color filter 81*f*, and output the generated image pickup signal to the processor 4B.

The primary color filter 81*f* is formed by arranging an R filter formed such that a transmittance of a red region to a near infrared region becomes relatively higher than the transmittance of the other wavelength band, a G filter formed such that the transmittance of a green region becomes relatively higher than the transmittance of the other wavelength band, and a B filter formed such that the transmittance of a blue region becomes relatively higher than the transmittance of the other wavelength band in a mosaic shape in a Bayer array at positions corresponding to the respective pixels of the image pickup device 81*b*.

The light source device 3B is configured including a light source unit 32B instead of the light source unit 32 of the light source device 3.

The light source unit 32B is configured including the blue light sources 32*a* and 32*b* and a broadband light source 32*i*.

The broadband light source 32*i* is provided with a blue LED and a fluorescent material which is excited by the blue LED and emits yellow fluorescence for example, and is configured to emit GR light which is broadband light including the wavelength from 500 nm to 700 nm. Note that the emission light quantity of the broadband light source 32*i* is assumed to be stipulated as the total light quantity obtained by integrating the intensity of the light of the respective wavelengths included in the wavelength band of the GR light.

The processor 4B is configured including a color separation processing portion 82 between the A/D conversion portion 42 and the WB processing portion 43 in the processor 4.

The color separation processing portion 82 is configured including an arithmetic processing circuit capable of performing color separation processing, for example. In addition, the color separation processing portion 82 is configured to perform the color separation processing for respectively separating the image data of a blue component obtained by picking up the image of the return light which has passed through the B filter of the primary color filter 81*f*, the image data of a green component obtained by picking up the image of the return light which has passed through the G filter of the primary color filter 81*f*, and the image data of a red component obtained by picking up the image of the return light which has passed through the R filter of the primary color filter 81*f*, from the image data outputted from the A/D conversion portion 42. Furthermore, the color separation processing portion 82 is configured to output the image data of the respective color components obtained by the color separation processing described above to the WB processing portion 43.

Subsequently, the specific operations or the like of the observation system 1B relating to the present embodiment will be described below. Note that, hereinafter, for the simplification, the case that the contrast "normal" is selected in the contrast emphasizing switch will be described as an example.

First, a user connects the respective portions of the observation system 1B, supplies the power, then performs the operation of switching the illumination switch (not shown in the figure) provided in the scope switch 23 and/or the input device 6 from off to on, for example, and thus gives the instruction for causing the illumination light to be supplied from the light source device 3B to the endoscope 2B to the control portion 47. In addition, the user gives the instruction for not highlighting the structure included in the biological tissue to the control portion 47 by performing the operation of selecting the sharpness "off" in the sharpness emphasizing switch provided in the scope switch 23 and/or the input device 6, for example.

When detecting that the power source of the processor 4B is turned on and the illumination switch is turned on, the control portion 47 generates the illumination control signal for illuminating the object by an illumination pattern IP3 of simultaneous irradiation, and outputs the signal to the light source control portion 31. Specifically, when detecting that the power source of the processor 4B is turned on and the illumination switch is turned on, the control portion 47 generates the illumination control signal for illuminating the object by the illumination pattern IP3 of making the blue light source 32*a*, the blue light source 32*b* and the broadband light source 32*i* simultaneously emit the light, and outputs the signal to the light source control portion 31.

In addition, when detecting that the sharpness "off" is selected in the sharpness emphasizing switch, for example, the control portion 47 generates the emission light quantity ratio control signal for setting the emission light quantity of the blue light sources 32*a* and 32*b* to a mutually same emission light quantity EQ, and setting the emission light quantity of the broadband light source 32*i* to an emission light quantity ER, and outputs the signal to the light source control portion 31.

The light source control portion 31 generates and outputs the light source drive signal for making the blue light source 32*a*, the blue light source 32*b* and the broadband light source 32*i* simultaneously emit the light, according to the illumination control signal outputted from the control portion 47.

In addition, the light source control portion 31 generates and outputs the light source drive signal for making the blue light sources 32*a* and 32*b* emit the light by the emission light quantity EQ, and making the broadband light source 32*i* emit the light by the emission light quantity ER, when the sharpness "off" is selected in the sharpness emphasizing switch, according to the emission light quantity ratio control signal outputted from the control portion 47.

Figure 33:
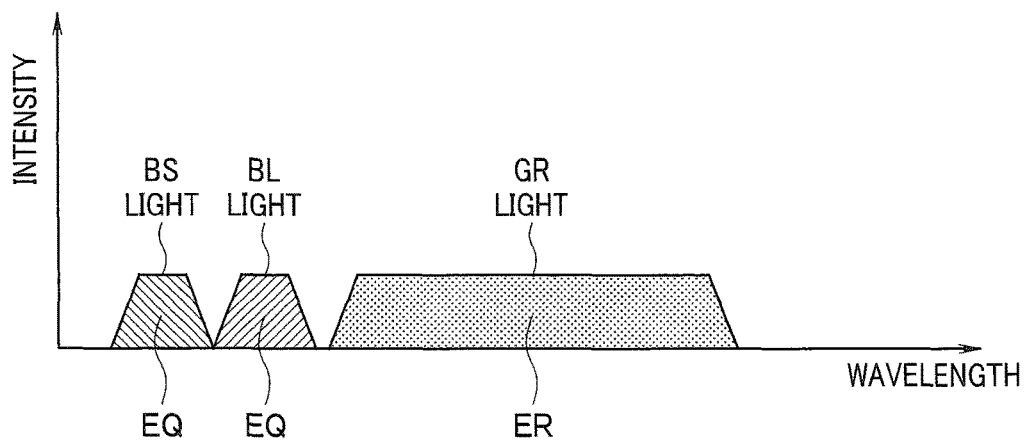
FIG. 33 is a diagram for describing one example of the illumination light supplied from the light source device in the third embodiment.

Then, according to the operations of the control portion 47 and the light source control portion 31 as described above, when the sharpness "off" is selected in the sharpness emphasizing switch, for example, as illustrated in FIG. 33, the illumination light including the BS light emitted by the emission light quantity EQ, the BL light emitted by the emission light quantity EQ, and the GR light emitted by the emission light quantity ER is supplied from the light source device 3B, return light LU including the BS light, the BL light and the GR light is emitted from the object illuminated by the illumination light, and image data ILU obtained by picking up the image of the return light LU is outputted from the A/D conversion portion 42 to the color separation processing portion 82.

The color separation processing portion 82 performs the color separation processing for respectively separating image data ILUB of the blue component obtained by picking up the image of the return light which has passed through the B filter of the primary color filter 81*f*, image data ILUG of the green component obtained by picking up the image of the return light which has passed through the G filter of the primary color filter 81*f*, and image data ILUR of the red component obtained by picking up the image of the return light which has passed through the R filter of the primary color filter 81*f*, from the image data ILU outputted from the A/D conversion portion 42. In addition, the color separation processing portion 82 outputs the respective image data ILUB, ILUG and ILUR obtained by the color separation processing described above to the WB processing portion 43.

The control portion 47 performs the control for causing the white balance processing using the predetermined white balance coefficient to be performed to each image data successively outputted from the color separation processing portion 82 to the WB processing portion 43.

When detecting that the sharpness "off" is selected in the sharpness emphasizing switch, for example, the control portion 47 reads the spatial filter SFA designed to have the filter characteristic as illustrated in FIG. 3 for example from the memory 47*a*, and performs the control for causing the spatial filter processing using the read spatial filter SFA to be performed to the sharpness emphasizing portion 44.

The sharpness emphasizing portion 44 executes the spatial filter processing using the spatial filter SFA to each of the image data ILUB ILUG and ILUR outputted from the WB processing portion 43 when the sharpness "off" is selected in the sharpness emphasizing switch according to the control of the control portion 47, and outputs the image data to which the spatial filter processing is executed to the gradation conversion portion 45.

When detecting that the contrast "normal" is selected in the contrast emphasizing switch, for example, the control portion 47 reads the gradation conversion function TFA having the input/output characteristic as illustrated in FIG. 4 from the memory 47*a*, and performs the control for causing the gradation conversion processing using the read gradation conversion function TFA to be performed to each image data successively outputted from the sharpness emphasizing portion 44 to the gradation conversion portion 45.

The control portion 47 performs the control for making the image data ILUB outputted from the gradation conversion portion 45 be allocated to the B channel of the display device 5, making the image data ILUG outputted from the gradation conversion portion 45 be allocated to the G channel of the display device 5, and making the image data ILUR outputted from the gradation conversion portion 45 be allocated to the R channel of the display device 5 to the display control portion 46.

Then, according to the operation of the control portion 47 or the like as described above, when the sharpness "off" is selected in the sharpness emphasizing switch, the observation image in which the structure included in the biological tissue can be observed with the visibility almost equal to the visibility in the natural state that the emphasizing processing is not applied is displayed at the display device 5.

On the other hand, the user arranges the distal end portion 2*c* at the position at which the image of the biological tissue of the observation target existing inside the subject can be picked up, by inserting the insertion portion 2*a* of the endoscope 2B into the subject. Then, for example, by appropriately selecting the sharpness in the sharpness emphasizing switch according to the observation distance between the distal end portion 2*c* and the biological tissue of the observation target, the user gives the instruction for highlighting the capillary existing in the surface layer of the biological tissue of the observation target at the desired emphasis degree to the control portion 47.

Specifically, for example, in the case that the observation distance between the distal end portion 2*c* and the biological tissue of the observation target belongs to the distant view, by performing the operation of selecting the sharpness "weak" in the sharpness emphasizing switch, the user gives the instruction for causing highlighting to be performed at such an emphasis degree that a part where the capillaries are distributed in a high density in the surface layer of the biological tissue of the observation target becomes easy to view compared to the part at the sharpness "off" to the control portion 47.

When detecting that the sharpness "weak" is selected in the sharpness emphasizing switch, for example, the control portion 47 generates the emission light quantity ratio control signal for setting the emission light quantity of the blue light source 32*a* to an emission light quantity ES larger than the emission light quantity EQ, setting the emission light quantity of the blue light source 32*b* to an emission light quantity ET smaller than the emission light quantity EQ, and setting the emission light quantity of the broadband light source 32*i* to the emission light quantity ER, and outputs the signal to the light source control portion 31. Note that, when setting the emission light quantity at the sharpness "weak", the control portion 47 performs the adjustment for equalizing the value obtained by adding the emission light quantity EQ of the two blue light sources 32*a* and 32*b* (doubling the emission light quantity EQ) at the sharpness "off" and the value obtained by adding the emission light quantities ES and ET.

The light source control portion 31 generates and outputs the light source drive signal for making the blue light source 32*a* emit the light by the emission light quantity ES, making the blue light source 32*b* emit the light by the emission light quantity ET, and making the broadband light source 32*i* emit the light by the emission light quantity ER, when the sharpness "weak" is selected in the sharpness emphasizing switch, according to the emission light quantity ratio control signal outputted from the control portion 47.

Figure 34:
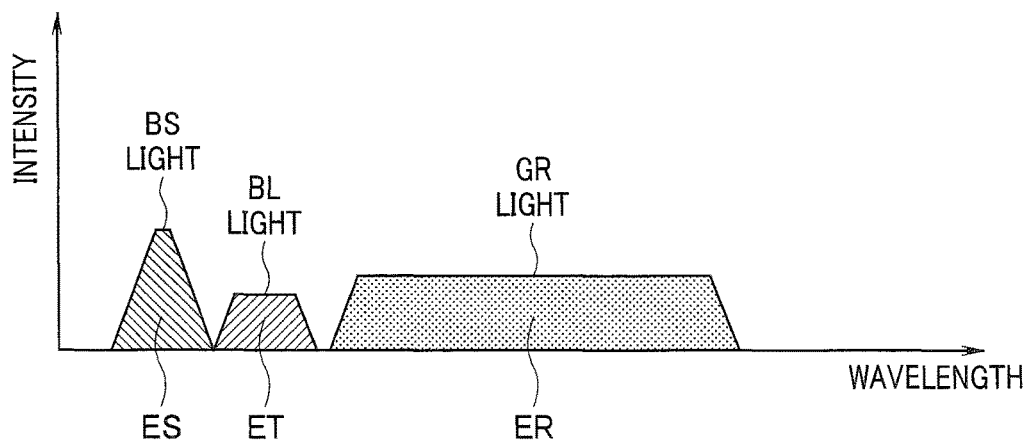
FIG. 34 is a diagram for describing one example of the illumination light supplied from the light source device in the third embodiment.

Then, according to the operations of the control portion 47 and the light source control portion 31 as described above, when the sharpness "weak" is selected in the sharpness emphasizing switch, for example, as illustrated in FIG. 34, the illumination light including the BS light emitted by the emission light quantity ES, the BL light emitted by the emission light quantity ET, and the GR light emitted by the emission light quantity ER is supplied from the light source device 3B, return light LV including the BS light, the BL light and the GR light is emitted from the object illuminated by the illumination light, and image data ILV obtained by picking up the image of the return light LV is outputted from the A/D conversion portion 42 to the color separation processing portion 82.

The color separation processing portion 82 performs the color separation processing for respectively separating image data ILVB of the blue component obtained by picking up the image of the return light which has passed through the B filter of the primary color filter 81*f*, image data ILVG of the green component obtained by picking up the image of the return light which has passed through the G filter of the primary color filter 81*f*, and image data ILVR of the red component obtained by picking up the image of the return light which has passed through the R filter of the primary color filter 81*f*, from the image data ILV outputted from the A/D conversion portion 42. In addition, the color separation processing portion 82 outputs the respective image data ILVB, ILVG and ILVR obtained by the color separation processing described above to the WB processing portion 43.

When detecting that the sharpness "weak" is selected in the sharpness emphasizing switch, for example, the control portion 47 reads the spatial filter SFE designed to have the filter characteristic as illustrated in FIG. 15 for example from the memory 47*a*, and performs the control for causing the spatial filter processing using the read spatial filter SFE to be performed to the sharpness emphasizing portion 44.

The sharpness emphasizing portion 44 executes the spatial filter processing using the spatial filter SFE to each of the image data ILVB, ILVG and ILVR outputted from the WB processing portion 43 when the sharpness "weak" is selected in the sharpness emphasizing switch according to the control of the control portion 47, and outputs the image data to which the spatial filter processing is executed to the gradation conversion portion 45.

The control portion 47 performs the control for making the image data ILVB outputted from the gradation conversion portion 45 be allocated to the B channel of the display device 5, making the image data ILVG outputted from the gradation conversion portion 45 be allocated to the G channel of the display device 5, and making the image data ILVR outputted from the gradation conversion portion 45 be allocated to the R channel of the display device 5 to the display control portion 46.

Then, according to the operation of the control portion 47 or the like as described above, when the sharpness "weak" is selected in the sharpness emphasizing switch, the observation image in which the part where the capillaries are distributed in the high density in the surface layer of the biological tissue is emphasized compared to the part at the sharpness "off" is displayed at the display device 5. In other words, according to the operation of the control portion 47 or the like as described above, when the sharpness "weak" is selected in the sharpness emphasizing switch, the observation image in which the visibility of the part where the capillaries are distributed in the high density in the surface layer of the biological tissue of the observation target is improved more than the visibility at the sharpness "off" is displayed at the display device 5.

On the other hand, for example, in the case that the observation distance between the distal end portion 2c and the biological tissue of the observation target belongs to the intermediate view, by performing the operation of selecting the sharpness "middle" in the sharpness emphasizing switch, the user gives the instruction for causing highlighting to be performed at such an emphasis degree that the part where the capillaries are distributed in the high density in the surface layer of the biological tissue of the observation target becomes easy to view compared to the part at the sharpness "weak" to the control portion 47.

When detecting that the sharpness "middle" is selected in the sharpness emphasizing switch, for example, the control portion 47 generates the emission light quantity ratio control signal for setting the emission light quantity of the blue light sources 32a to an emission light quantity EU larger than the emission light quantity ES, setting the emission light quantity of blue light source 32b to an emission light quantity EV smaller than the emission light quantity ET, and setting the emission light quantity of the broadband light source 32i to the emission light quantity ER, and outputs the signal to the light source control portion 31. Note that, when setting the emission light quantity at the sharpness "middle", the control portion 47 performs the adjustment for equalizing the value obtained by adding the emission light quantity ES of the blue light source 32a and the emission light quantity ET of the blue light source 32b at the sharpness "weak" and the value obtained by adding the emission light quantities EU and EV.

The light source control portion 31 generates and outputs the light source drive signal for making the blue light source 32a emit the light by the emission light quantity EU, making the blue light source 32b emit the light by the emission light quantity EV, and making the broadband light source 32i emit the light by the emission light quantity ER, when the sharpness "middle" is selected in the sharpness emphasizing switch, according to the emission light quantity ratio control signal outputted from the control portion 47.

Figure 35:
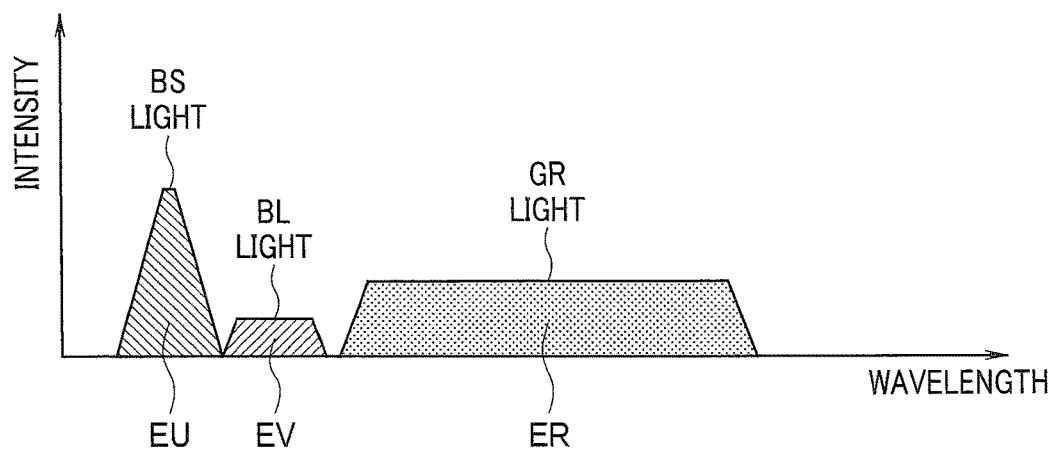
FIG. 35 is a diagram for describing one example of the illumination light supplied from the light source device in the third embodiment.

Then, according to the operations of the control portion 47 and the light source control portion 31 as described above, when the sharpness "middle" is selected in the sharpness emphasizing switch, for example, as illustrated in FIG. 35, the illumination light including the BS light emitted by the emission light quantity EU, the BL light emitted by the emission light quantity EV, and the GR light emitted by the emission light quantity ER is supplied from the light source device 3B, return light LW including the BS light, the BL light and the GR light is emitted from the object illuminated by the illumination light, and image data ILW obtained by picking up the image of the return light LW is outputted from the A/D conversion portion 42 to the color separation processing portion 82.

The color separation processing portion 82 performs the color separation processing for respectively separating image data ILWB of the blue component obtained by picking up the image of the return light which has passed through the B filter of the primary color filter 81f, image data ILWG of the green component obtained by picking up the image of the return light which has passed through the G filter of the primary color filter 81f, and image data ILWR of the red component obtained by picking up the image of the return light which has passed through the R filter of the primary color filter 81f, from the image data ILW outputted from the A/D conversion portion 42. In addition, the color separation processing portion 82 outputs the respective image data ILWB, ILWG and ILWR obtained by the color separation processing described above to the WB processing portion 43.

When detecting that the sharpness "middle" is selected in the sharpness emphasizing switch, for example, the control portion 47 reads the spatial filter SFF designed to have the filter characteristic as illustrated in FIG. 17 for example from the memory 47a, and performs the control for causing the spatial filter processing using the read spatial filter SFF to be performed to the sharpness emphasizing portion 44.

The sharpness emphasizing portion 44 executes the spatial filter processing using the spatial filter SFF to each of the image data ILWB, ILWG and ILWR outputted from the WB processing portion 43 when the sharpness "middle" is selected in the sharpness emphasizing switch according to the control of the control portion 47, and outputs the image data to which the spatial filter processing is executed to the gradation conversion portion 45.

The control portion 47 performs the control for making the image data ILWB outputted from the gradation conversion portion 45 be allocated to the B channel of the display device 5, making the image data ILWG outputted from the gradation conversion portion 45 be allocated to the G channel of the display device 5, and making the image data ILWR outputted from the gradation conversion portion 45 be allocated to the R channel of the display device 5 to the display control portion 46.

Then, according to the operation of the control portion 47 or the like as described above, when the sharpness "middle" is selected in the sharpness emphasizing switch, the observation image in which the part where the capillaries are distributed in the high density in the surface layer of the biological tissue is emphasized compared to the part at the sharpness "weak" is displayed at the display device 5. In other words, according to the operation of the control portion 47 or the like as described above, when the sharpness "middle" is selected in the sharpness emphasizing switch, the observation image in which the visibility of the part where the capillaries are distributed in the high density in the surface layer of the biological tissue of the observation target is improved more than the visibility at the sharpness "weak" is displayed at the display device 5.

On the other hand, for example, in the case that the observation distance between the distal end portion 2c and the biological tissue of the observation target belongs to the close view, by performing the operation of selecting the sharpness "strong" in the sharpness emphasizing switch, the user gives the instruction for causing highlighting to be performed at such an emphasis degree that the capillary existing in the surface layer of the biological tissue of the observation target becomes easy to view compared to the capillary at the sharpness "middle" to the control portion 47.

When detecting that the sharpness "strong" is selected in the sharpness emphasizing switch, for example, the control portion 47 generates the emission light quantity ratio control signal for setting the emission light quantity of the blue light sources 32a to an emission light quantity EW larger than the emission light quantity EU, setting the emission light quantity of blue light source 32b to an emission light quantity EX smaller than the emission light quantity EV, and setting the emission light quantity of the broadband light source 32i to the emission light quantity ER, and outputs the signal to the light source control portion 31. Note that, when setting the emission light quantity at the sharpness "strong", the control portion 47 performs the adjustment for equalizing the value obtained by adding the emission light quantity EU of the blue light source 32a and the emission light quantity EV of the blue light source 32b at the sharpness "middle" and the value obtained by adding the emission light quantities EW and EX.

The light source control portion 31 generates and outputs the light source drive signal for making the blue light source 32a emit the light by the emission light quantity EW, making the blue light source 32b emit the light by the emission light quantity EX, and making the broadband light source 32i emit the light by the emission light quantity ER, when the sharpness "strong" is selected in the sharpness emphasizing switch, according to the emission light quantity ratio control signal outputted from the control portion 47.

Figure 36:
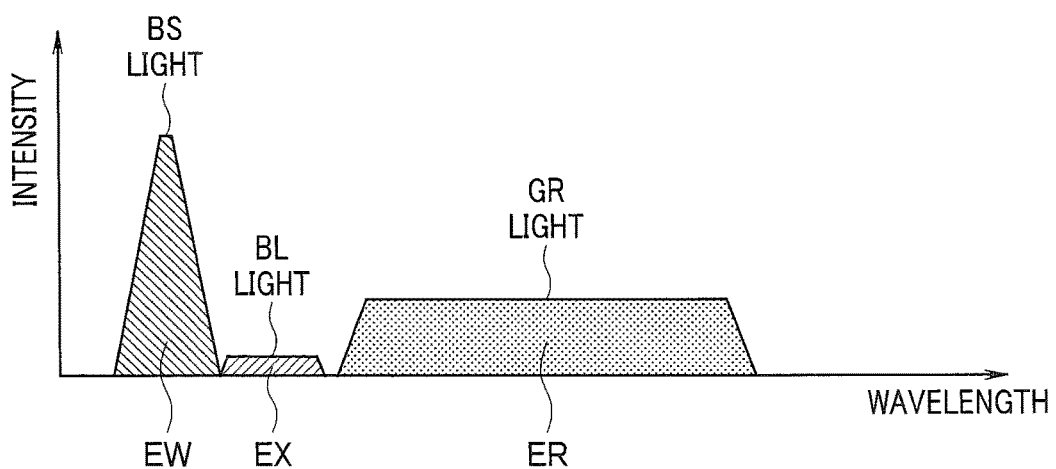
FIG. 36 is a diagram for describing one example of the illumination light supplied from the light source device in the third embodiment.

Then, according to the operations of the control portion 47 and the light source control portion 31 as described above, when the sharpness "strong" is selected in the sharpness emphasizing switch, for example, as illustrated in FIG. 36, the illumination light including the BS light emitted by the emission light quantity EW, the BL light emitted by the emission light quantity EX, and the GR light emitted by the emission light quantity ER is supplied from the light source device 3B, return light LX including the BS light, the BL light and the GR light is emitted from the object illuminated by the illumination light, and image data ILX obtained by picking up the image of the return light LX is outputted from the A/D conversion portion 42 to the color separation processing portion 82.

The color separation processing portion 82 performs the color separation processing for respectively separating image data ILXB of the blue component obtained by picking up the image of the return light which has passed through the B filter of the primary color filter 81f, image data ILXG of the green component obtained by picking up the image of the return light which has passed through the G filter of the primary color filter 81f, and image data ILXR of the red component obtained by picking up the image of the return light which has passed through the R filter of the primary color filter 81f, from the image data ILX outputted from the A/D conversion portion 42. In addition, the color separation processing portion 82 outputs the respective image data ILXB, ILXG and ILXR obtained by the color separation processing described above to the WB processing portion 43.

When detecting that the sharpness "strong" is selected in the sharpness emphasizing switch, for example, the control portion 47 reads the spatial filter SFG designed to have the filter characteristic as illustrated in FIG. 19 for example from the memory 47a, and performs the control for causing the spatial filter processing using the read spatial filter SFG to be performed to the sharpness emphasizing portion 44.

The sharpness emphasizing portion 44 executes the spatial filter processing using the spatial filter SFG to each of the image data ILXB, ILXG and ILXR outputted from the WB processing portion 43 when the sharpness "strong" is selected in the sharpness emphasizing switch according to the control of the control portion 47, and outputs the image data to which the spatial filter processing is executed to the gradation conversion portion 45.

The control portion 47 performs the control for making the image data ILXB outputted from the gradation conversion portion 45 be allocated to the B channel of the display device 5, making the image data ILXG outputted from the gradation conversion portion 45 be allocated to the G channel of the display device 5, and making the image data ILXR outputted from the gradation conversion portion 45 be allocated to the R channel of the display device 5 to the display control portion 46.

Then, according to the operation of the control portion 47 or the like as described above, when the sharpness "strong" is selected in the sharpness emphasizing switch, the observation image in which the capillary existing in the surface layer of the biological tissue is emphasized compared to the capillary at the sharpness "middle" is displayed at the display device 5. In other words, according to the operation of the control portion 47 or the like as described above, when the sharpness "strong" is selected in the sharpness emphasizing switch, the observation image in which the visibility of the capillary existing in the surface layer of the biological tissue of the observation target is improved more than the visibility at the sharpness "middle" is displayed at the display device 5.

According to the configuration and operations or the like of the present embodiment as described above, the generation frequency of the artifact such as the color noise due to the spatial filter processing for highlighting the structure such as the blood vessel included in the biological tissue can be suppressed to the low frequency, that is, the decline of the image quality which occurs according to the emphasis degree when highlighting the structure can be suppressed.

In addition, according to the present embodiment, the emission light quantities in the respective light sources of the light source unit 32B are adjusted according to the sharpness selected in the sharpness emphasizing switch so that the fluctuation of the brightness and/or the color tone of the observation image which can occur accompanying the changeover of the sharpness in the sharpness emphasizing switch can be suppressed as much as possible.

(Fourth Embodiment)

FIG. 37 to FIG. 45 relate to the fourth embodiment of the present invention.

Note that, in the present embodiment, the detailed descriptions related to parts including the components or the like similar to the components in at least one of the first to third embodiments are omitted, and parts including the components or the like different from the components in all of the first to third embodiments will be mainly described.

Figure 37:
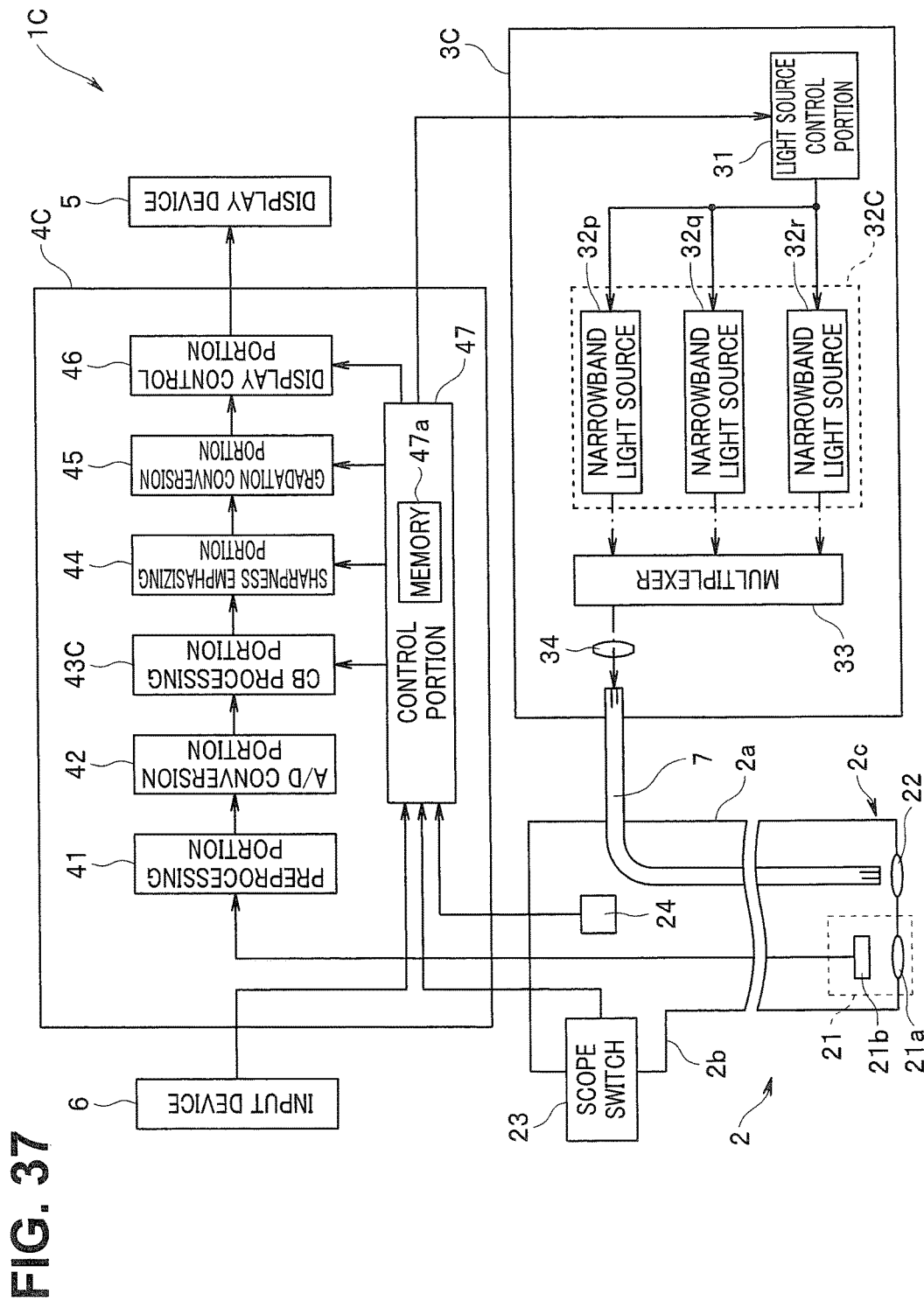
FIG. 37 is a diagram illustrating a configuration of the main part of the observation system relating to a fourth embodiment.

An observation system 1C is configured including a light source device 3C instead of the light source device 3 of the observation system 1, and a processor 4C instead of the processor 4 of the observation system 1, as illustrated in FIG. 37. FIG. 37 is a diagram illustrating the configuration of the main part of the observation system relating to the fourth embodiment.

The light source device 3C is configured including a light source unit 32C instead of the light source unit 32 of the light source device 3.

The light source unit 32C is configured including three narrowband light sources 32p, 32q and 32r instead of the respective light sources of the light source device 3.

The narrowband light source 32p is provided with the blue LED for example, and is configured to emit NBS light which is blue narrowband light, the center wavelength of which is set at 415 nm. That is, the NBS light has the characteristic that the NBS light is scattered and/or reflected in the surface layer of the biological tissue and the extinction coefficient with respect to blood becomes high compared to NBL light to be described later. Note that the emission light quantity of the narrowband light source 32p is assumed to be stipulated as the total light quantity obtained by integrating the intensity of the light of the respective wavelengths included in the wavelength band of the NBS light.

The narrowband light source 32q is provided with the blue LED for example, and is configured to emit the NBL light which is the blue narrowband light, the center wavelength of which is set at 450 nm. That is, the NBL light has the characteristic that the NBL light is scattered and/or reflected in the surface layer of the biological tissue and the extinction coefficient with respect to blood becomes low compared to the NBS light. Note that the emission light quantity of the narrowband light source 32q is assumed to be stipulated as the total light quantity obtained by integrating the intensity of the light of the respective wavelengths included in the wavelength band of the NBL light.

The narrowband light source 32r is provided with the green LED for example, and is configured to emit NG light which is green narrowband light, the center wavelength of which is set at 540 nm. That is, the NG light has the characteristic that the NG light is scattered and/or reflected in the middle layer more on the surface layer side than the deep layer of the biological tissue and the extinction coefficient with respect to blood becomes relatively high. Note that the emission light quantity of the narrowband light source 32r is assumed to be stipulated as the total light quantity obtained by integrating the intensity of the light of the respective wavelengths included in the wavelength band of the NG light.

The processor 4C is configured including a color balance processing portion (abbreviated as a CB processing portion, hereinafter) 43C instead of the WB processing portion 43 in the processor 4.

The CB processing portion 43C is configured to execute color balance processing to the image data outputted from the A/D conversion portion 42 according to the control of the control portion 47, and output the image data to which the color balance processing is executed to the sharpness emphasizing portion 44.

Subsequently, specific operations or the like of the observation system 1C relating to the present embodiment will be described below. Note that, hereinafter, for the simplification, the case that the contrast "normal" is selected in the contrast emphasizing switch will be described as an example.

First, a user connects the respective portions of the observation system 1C, supplies the power, then performs the operation of switching the illumination switch (not shown in the figure) provided in the scope switch 23 and/or the input device 6 from off to on, for example, and thus gives the instruction for causing the illumination light to be supplied from the light source device 3C to the endoscope 2 to the control portion 47. In addition, the user gives the instruction for not highlighting the structure included in the biological tissue by performing the operation of selecting the sharpness "off" in the sharpness emphasizing switch provided in the scope switch 23 and/or the input device 6, for example.

When detecting that the power source of the processor 4C is turned on and the illumination switch is turned on, the control portion 47 generates the illumination control signal for illuminating the object by a time division illumination pattern IP4, and outputs the signal to the light source control portion 31. Specifically, when detecting that the power source of the processor 4C is turned on and the illumination switch is turned on, the control portion 47 generates the illumination control signal for illuminating the object by the illumination pattern IP4 of cyclically repeating an illumination period PG of making the narrowband light source 32p emit the light, an illumination period PH of making the narrowband light source 32q emit the light and an illumination period PI of making the narrowband light source 32r emit the light in the order for example, and outputs the signal to the light source control portion 31. Note that the order of the respective illumination periods in the illumination pattern IP4 may not be the order of PG→PH→PI.

In addition, when detecting that the sharpness "off" is selected in the sharpness emphasizing switch, for example, the control portion 47 generates the emission light quantity ratio control signal for setting the emission light quantity of the narrowband light sources 32p, 32q and 32r to a mutually same emission light quantity Ea, and outputs the signal to the light source control portion 31.

The light source control portion 31 generates and outputs the light source drive signal for making the narrowband light source 32p emit the light while making the narrowband light sources 32q and 32r quench the light in the illumination period PG, making the narrowband light source 32q emit the light while making the narrowband light sources 32p and 32r quench the light in the illumination period PH, and making the narrowband light source 32r emit the light while making the narrowband light sources 32p and 32q quench the light in the illumination period PI, according to the illumination control signal outputted from the control portion 47.

In addition, the light source control portion 31 generates and outputs the light source drive signal for making the respective narrowband light sources of the light source unit 32C emit the light by the emission light quantity Ea, when the sharpness "off" is selected in the sharpness emphasizing switch, according to the emission light quantity ratio control signal outputted from the control portion 47.

Figure 38:
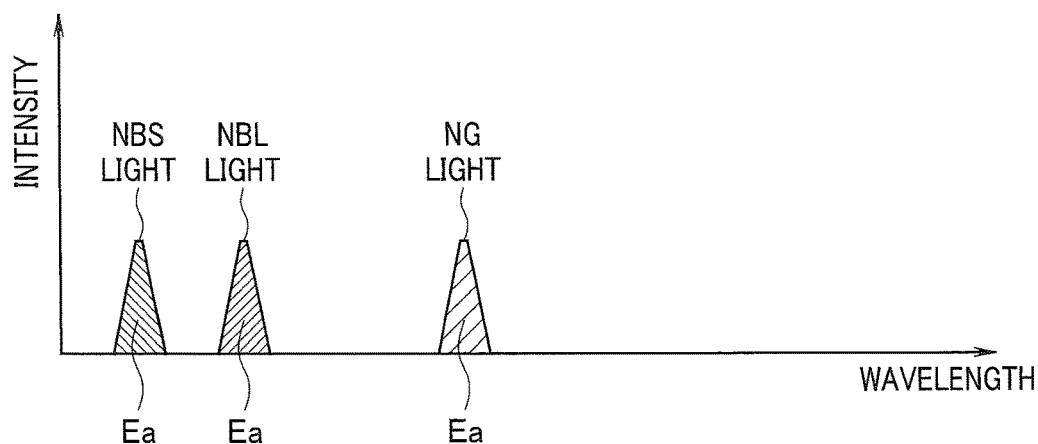
FIG. 38 is a diagram for describing one example of the illumination light supplied from the light source device in the fourth embodiment.

Then, according to the operations of the control portion 47 and the light source control portion 31 as described above, in the illumination period PG of the illumination pattern IP4, for example, as illustrated in FIG. 38, the NBS light emitted by the emission light quantity Ea is supplied from the light source device 3C as the illumination light, return light La according to the NBS light is emitted from the object illuminated by the illumination light, and image data ILa obtained by picking up the image of the return light La is outputted from the A/D conversion portion 42 to the CB processing portion 43C.

In addition, according to the operations of the control portion 47 and the light source control portion 31 as described above, in the illumination period PH of the illumination pattern IP4, for example, as illustrated in FIG. 38, the NBL light emitted by the emission light quantity Ea is supplied from the light source device 3C as the illumination light, return light Lb according to the NBL light is emitted from the object illuminated by the illumination light, and image data ILb obtained by picking up the image of the return light Lb is outputted from the A/D conversion portion 42 to the CB processing portion 43C.

In addition, according to the operations of the control portion 47 and the light source control portion 31 as described above, in the illumination period PI of the illumination pattern IP4, for example, as illustrated in FIG. 38, the NG light emitted by the emission light quantity Ea is supplied from the light source device 3C as the illumination light, return light Lc according to the NG light is emitted from the object illuminated by the illumination light, and image data ILc obtained by picking up the image of the return light Lc is outputted from the A/D conversion portion 42 to the CB processing portion 43C.

The control portion 47 performs the control for causing the color balance processing using a predetermined color balance coefficient to be performed to the CB processing portion 43C. Note that the above-described predetermined color balance coefficient is assumed to be stored beforehand in the memory 47a as the value used for causing the image data obtained by picking up the image of a predetermined reference object to be displayed (visually recognized) at the display device 5 as the observation image of a predetermined color tone.

Figure 39:
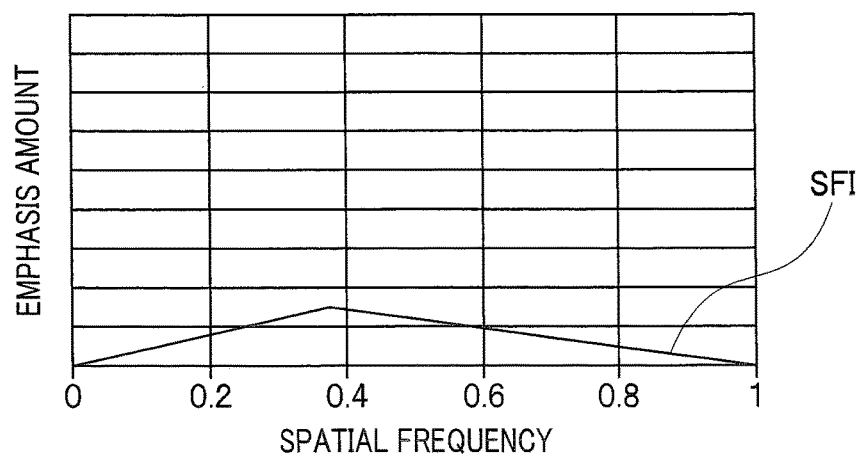
FIG. 39 is a diagram illustrating one example of the filter characteristic of the spatial filter used in the spatial filter processing in the fourth embodiment.

When detecting that the sharpness "off" is selected in the sharpness emphasizing switch, for example, the control portion 47 reads a spatial filter SFI designed to have the filter characteristic as illustrated in FIG. 39 for example from the memory 47a, and performs the control for causing the spatial filter processing using the read spatial filter SFI to be performed to the sharpness emphasizing portion 44. Note that the filter characteristic in FIG. 39 is illustrated as the characteristic of such a mountain shape that the spatial frequency emphasized by the maximum emphasis amount is present in the low band.

The sharpness emphasizing portion 44 executes the spatial filter processing using the spatial filter SFI to each of the image data ILa, ILb and ILc outputted from the CB processing portion 43C when the sharpness "off" is selected in the sharpness emphasizing switch according to the control of the control portion 47, and outputs the image data to which the spatial filter processing is executed to the gradation conversion portion 45.

When detecting that the contrast "normal" is selected in the contrast emphasizing switch, for example, the control portion 47 reads the gradation conversion function TFA having the input/output characteristic as illustrated in FIG. 4 from the memory 47a, and performs the control for causing the gradation conversion processing using the read gradation conversion function TFA to be performed to each image data successively outputted from the sharpness emphasizing portion 44 to the gradation conversion portion 45.

The control portion 47 performs the control for making the image data ILa outputted from the gradation conversion portion 45 be allocated to the B channel of the display device 5, making the image data ILb outputted from the gradation conversion portion 45 be allocated to the G channel of the display device 5, and making the image data ILc outputted from the gradation conversion portion 45 be allocated to the R channel of the display device 5 to the display control portion 46.

Then, according to the operation of the control portion 47 or the like as described above, when the sharpness "off" is selected in the sharpness emphasizing switch, the observation image in which a state of the capillary and the musical structure existing in the surface layer of the biological tissue can be confirmed is displayed at the display device 5.

On the other hand, the user arranges the distal end portion 2c at the position at which the image of the biological tissue of the observation target existing inside the subject can be picked up, by inserting the insertion portion 2a of the endoscope 2 into the subject. Then, for example, by appropriately selecting the sharpness in the sharpness emphasizing switch according to the observation distance between the distal end portion 2c and the biological tissue of the observation target, the user gives the instruction for highlighting the capillary and the mucosal structure existing in the surface layer of the biological tissue of the observation target at the desired emphasis degree to the control portion 47.

Specifically, for example, in the case that the observation distance between the distal end portion 2c and the biological tissue of the observation target belongs to the distant view, by performing the operation of selecting the sharpness "weak" in the sharpness emphasizing switch, the user gives the instruction for causing highlighting to be performed at such an emphasis degree that the capillary and the mucosal structure existing in the surface layer of the biological tissue of the observation target become easy to view compared to the capillary and the mucosal structure at the sharpness "off" to the control portion 47.

When detecting that the sharpness "weak" is selected in the sharpness emphasizing switch, for example, the control portion 47 generates the emission light quantity ratio control signal for setting the emission light quantity of the narrowband light source 32p to an emission light quantity Eb larger than the emission light quantity Ea, setting the emission light quantity of the narrowband light source 32q to an emission light quantity Ec smaller than the emission light quantity Ea, and setting the emission light quantity of the narrowband light source 32r to the emission light quantity Ea, and outputs the signal to the light source control portion 31. Note that, when setting the emission light quantity at the sharpness "weak", the control portion 47 performs the adjustment for equalizing the value obtained by adding the emission light quantity Ea of the two narrowband light sources 32p and 32q (doubling the emission light quantity Ea) at the sharpness "off" and the value obtained by adding the emission light quantities Eb and Ec.

The light source control portion 31 generates and outputs the light source drive signal for making the narrowband light source 32p emit the light by the emission light quantity Eb, making the narrowband light source 32q emit the light by the emission light quantity Ec, and making the narrowband light source 32r emit the light by the emission light quantity Ea, when the sharpness "weak" is selected in the sharpness emphasizing switch, according to the emission light quantity ratio control signal outputted from the control portion 47.

Figure 40:
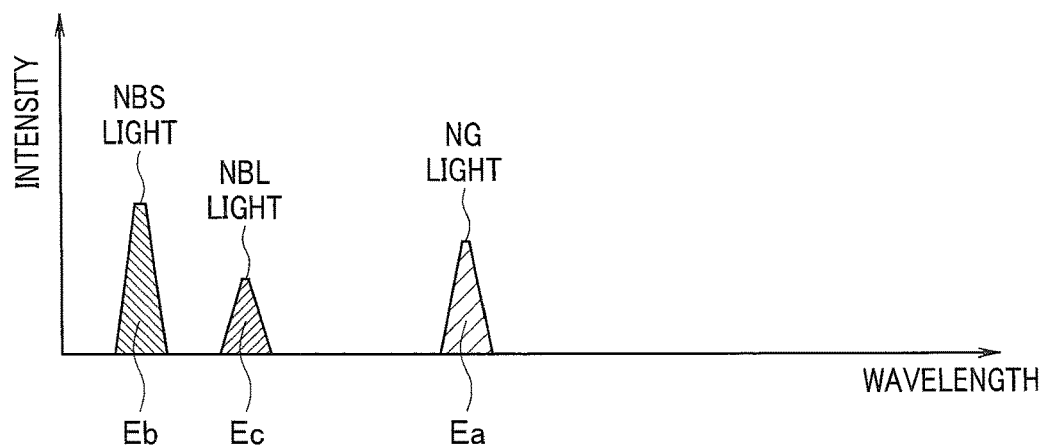
FIG. 40 is a diagram for describing one example of the illumination light supplied from the light source device in the fourth embodiment.

Then, according to the operations of the control portion 47 and the light source control portion 31 as described above, in the illumination period PG of the illumination pattern IP4, for example, as illustrated in FIG. 40, the NBS light emitted by the emission light quantity Eb is supplied from the light source device 3C as the illumination light, return light Ld according to the NBS light is emitted from the object illuminated by the illumination light, and image data ILd obtained by picking up the image of the return light Ld is outputted from the A/D conversion portion 42 to the CB processing portion 43C.

In addition, according to the operations of the control portion 47 and the light source control portion 31 as described above, in the illumination period PH of the illumination pattern IP4, for example, as illustrated in FIG. 40, the NBL light emitted by the emission light quantity Ec is supplied from the light source device 3C as the illumination light, return light Le according to the NBL light is emitted from the object illuminated by the illumination light, and image data ILe obtained by picking up the image of the return light Le is outputted from the A/D conversion portion 42 to the CB processing portion 43C.

In addition, according to the operations of the control portion 47 and the light source control portion 31 as described above, in the illumination period PI of the illumination pattern IP4, for example, as illustrated in FIG. 40, the NG light emitted by the emission light quantity Ea is supplied from the light source device 3C as the illumination light, the return light Lc according to the NG light is emitted from the object illuminated by the illumination light, and the image data ILc obtained by picking up the image of the return light Lc is outputted from the A/D conversion portion 42 to the CB processing portion 43C.

Figure 41:
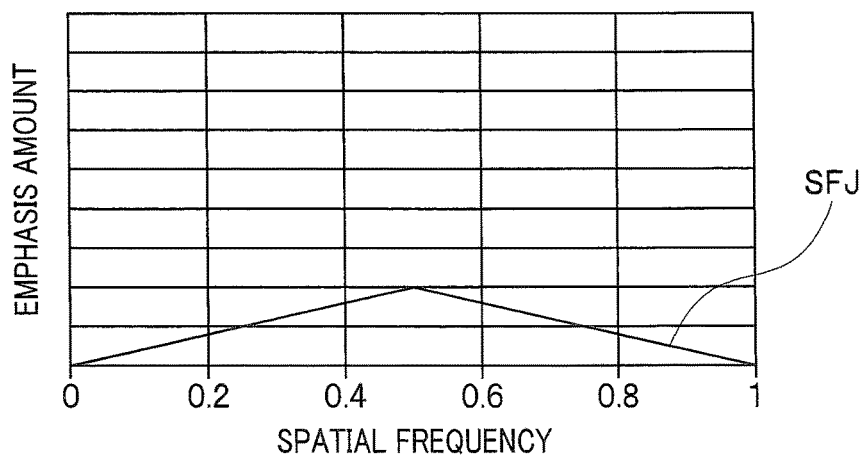
FIG. 41 is a diagram illustrating one example of the filter characteristic of the spatial filter used in the spatial filter processing in the fourth embodiment.

When detecting that the sharpness "weak" is selected in the sharpness emphasizing switch, for example, the control portion 47 reads a spatial filter SFJ designed to have the filter characteristic as illustrated in FIG. 41 for example from the memory 47a, and performs the control for causing the spatial filter processing using the read spatial filter SFJ to be performed to the sharpness emphasizing portion 44. Note that the filter characteristic in FIG. 41 is illustrated as the characteristic that the spatial frequency emphasized by the maximum emphasis amount exists in the middle band and the emphasis amount at the spatial frequency around the maximum emphasis amount is equal to or larger than the emphasis amount of the spatial filter SFI.

The sharpness emphasizing portion 44 executes the spatial filter processing using the spatial filter SFJ to each of the image data ILd, ILe and ILc outputted from the CB processing portion 43C when the sharpness "weak" is selected in the sharpness emphasizing switch according to the control of the control portion 47, and outputs the image data to which the spatial filter processing is executed to the gradation conversion portion 45.

The control portion 47 performs the control for making the image data ILd outputted from the gradation conversion portion 45 be allocated to the B channel of the display device 5, making the image data ILe outputted from the gradation conversion portion 45 be allocated to the G channel of the display device 5, and making the image data ILc outputted from the gradation conversion portion 45 be allocated to the R channel of the display device 5 to the display control portion 46.

Then, according to the operation of the control portion 47 or the like as described above, when the sharpness "weak" is selected in the sharpness emphasizing switch, the observation image in which the capillary and the mucosal structure existing in the surface layer of the biological tissue are emphasized compared to the capillary and the mucosal structure at the sharpness "off" is displayed at the display device 5. In other words, according to the operation of the control portion 47 or the like as described above, when the sharpness "weak" is selected in the sharpness emphasizing switch, the observation image in which the visibility of the capillary and the mucosal structure existing in the surface layer of the biological tissue of the observation target is improved more than the visibility at the sharpness "off" is displayed at the display device 5.

On the other hand, for example, in the case that the observation distance between the distal end portion 2c and the biological tissue of the observation target belongs to the intermediate view, by performing the operation of selecting the sharpness "middle" in the sharpness emphasizing switch, the user gives the instruction for causing highlighting to be performed at such an emphasis degree that the capillary and the mucosal structure existing in the surface layer of the biological tissue of the observation target become easy to view compared to the capillary and the mucosal structure at the sharpness "weak" to the control portion 47.

When detecting that the sharpness "middle" is selected in the sharpness emphasizing switch, for example, the control portion 47 generates the emission light quantity ratio control signal for setting the emission light quantity of the narrowband light source 32p to an emission light quantity Ed larger than the emission light quantity Eb, setting the emission light quantity of the narrowband light source 32q to an emission light quantity Ee smaller than the emission light quantity Ec, and setting the emission light quantity of the narrowband light source 32r to the emission light quantity Ea, and outputs the signal to the light source control portion 31. Note that, when setting the emission light quantity at the sharpness "middle", the control portion 47 performs the adjustment for equalizing the value obtained by adding the emission light quantity Ea of the two narrowband light sources 32p and 32q (doubling the emission light quantity Ea) at the sharpness "off" and the value obtained by adding the emission light quantities Ed and Ee.

The light source control portion 31 generates and outputs the light source drive signal for making the narrowband light source 32p emit the light by the emission light quantity Ed, making the narrowband light source 32q emit the light by the emission light quantity Ee, and making the narrowband light source 32r emit the light by the emission light quantity Ea, when the sharpness "middle" is selected in the sharpness emphasizing switch, according to the emission light quantity ratio control signal outputted from the control portion 47.

Figure 42:
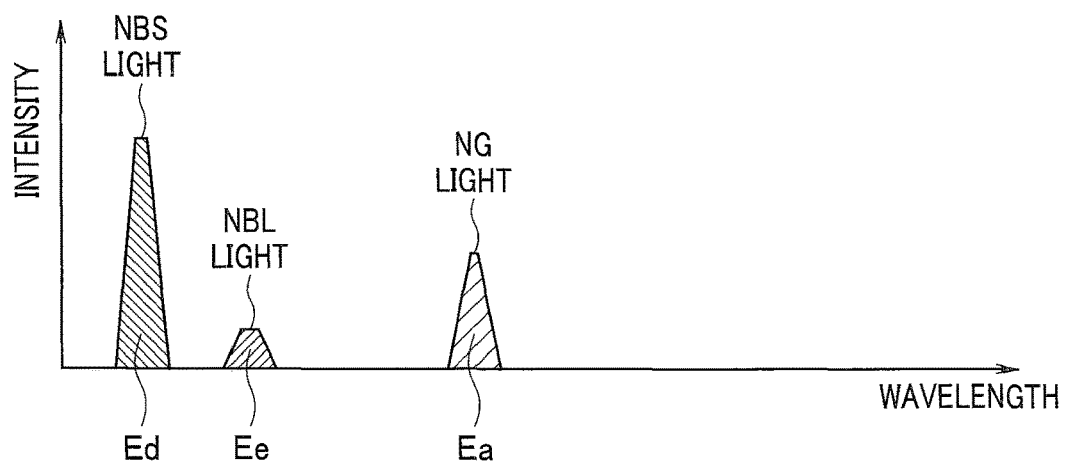
FIG. 42 is a diagram for describing one example of the illumination light supplied from the light source device in the fourth embodiment.

Then, according to the operations of the control portion 47 and the light source control portion 31 as described above, in the illumination period PG of the illumination pattern IP4, for example, as illustrated in FIG. 42, the NBS light emitted by the emission light quantity Ed is supplied from the light source device 3C as the illumination light, return light Lf according to the NB S light is emitted from the object illuminated by the illumination light, and image data ILf obtained by picking up the image of the return light Lf is outputted from the A/D conversion portion 42 to the CB processing portion 43C.

In addition, according to the operations of the control portion 47 and the light source control portion 31 as described above, in the illumination period PH of the illumination pattern IP4, for example, as illustrated in FIG. 42, the NBL light emitted by the emission light quantity Ee is supplied from the light source device 3C as the illumination light, return light Lg according to the NBL light is emitted from the object illuminated by the illumination light, and image data ILg obtained by picking up the image of the return light Lg is outputted from the A/D conversion portion 42 to the CB processing portion 43C.

In addition, according to the operations of the control portion 47 and the light source control portion 31 as described above, in the illumination period PI of the illumination pattern IP4, for example, as illustrated in FIG. 42, the NG light emitted by the emission light quantity Ea is supplied from the light source device 3C as the illumination light, the return light Lc according to the NG light is emitted from the object illuminated by the illumination light, and the image data ILc obtained by picking up the image of the return light Lc is outputted from the A/D conversion portion 42 to the CB processing portion 43C.

Figure 43:
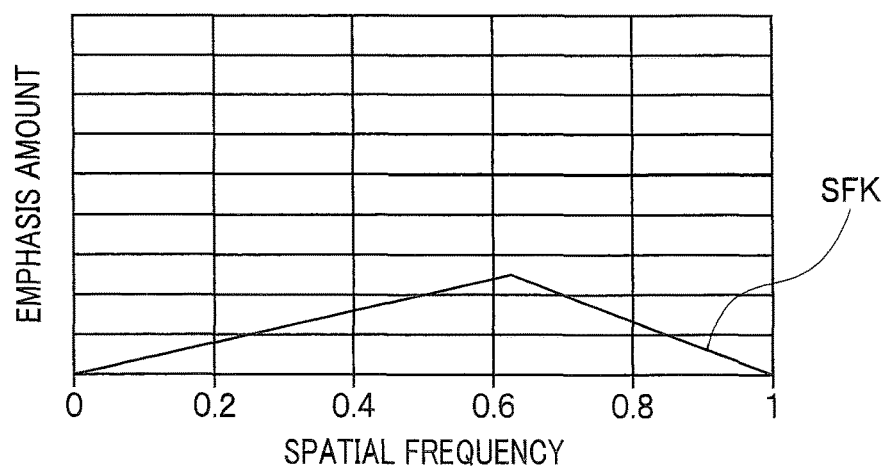
FIG. 43 is a diagram illustrating one example of the filter characteristic of the spatial filter used in the spatial filter processing in the fourth embodiment.

When detecting that the sharpness "middle" is selected in the sharpness emphasizing switch, for example, the control portion 47 reads a spatial filter SFK designed to have the filter characteristic as illustrated in FIG. 43 for example from the memory 47a, and performs the control for causing the spatial filter processing using the read spatial filter SFK to be performed to the sharpness emphasizing portion 44. Note that the filter characteristic in FIG. 43 is illustrated as the characteristic that the spatial frequency emphasized by the maximum emphasis amount exists in the high band and the emphasis amount at the spatial frequency around the maximum emphasis amount is equal to or larger than the emphasis amount of the spatial filter SFJ.

The sharpness emphasizing portion 44 executes the spatial filter processing using the spatial filter SFK to each of the image data ILf, ILg and ILc outputted from the CB processing portion 43C when the sharpness "middle" is selected in the sharpness emphasizing switch according to the control of the control portion 47, and outputs the image data to which the spatial filter processing is executed to the gradation conversion portion 45.

The control portion 47 performs the control for making the image data ILf outputted from the gradation conversion portion 45 be allocated to the B channel of the display device 5, making the image data ILg outputted from the gradation conversion portion 45 be allocated to the G channel of the display device 5, and making the image data ILc outputted from the gradation conversion portion 45 be allocated to the R channel of the display device 5 to the display control portion 46.

Then, according to the operation of the control portion 47 or the like as described above, when the sharpness "middle" is selected in the sharpness emphasizing switch, the observation image in which the capillary and the mucosal structure existing in the surface layer of the biological tissue are emphasized compared to the capillary and the mucosal structure at the sharpness "weak" is displayed at the display device 5. In other words, according to the operation of the control portion 47 or the like as described above, when the sharpness "middle" is selected in the sharpness emphasizing switch, the observation image in which the visibility of the capillary and the mucosal structure existing in the surface layer of the biological tissue of the observation target is improved more than the visibility at the sharpness "weak" is displayed at the display device 5.

On the other hand, for example, in the case that the observation distance between the distal end portion 2c and the biological tissue of the observation target belongs to the close view, by performing the operation of selecting the sharpness "strong" in the sharpness emphasizing switch, the user gives the instruction for causing highlighting to be performed at such an emphasis degree that the capillary and the mucosal structure existing in the surface layer of the biological tissue of the observation target become easy to view compared to the capillary and the mucosal structure at the sharpness "middle" to the control portion 47.

When detecting that the sharpness "strong" is selected in the sharpness emphasizing switch, for example, the control portion 47 generates the emission light quantity ratio control signal for setting the emission light quantity of the narrowband light source 32p to the emission light quantity Ed, setting the emission light quantity of the narrowband light source 32q to the emission light quantity Ee, and setting the emission light quantity of the narrowband light source 32r to an emission light quantity Ef smaller than the emission light quantity Ea, and outputs the signal to the light source control portion 31. Note that, when setting the emission light quantity at the sharpness "strong", the control portion 47 performs the adjustment for equalizing the value obtained by adding the emission light quantity Ea of the two narrowband light sources 32p and 32q (doubling the emission light quantity Ea) at the sharpness "off" and the value obtained by adding the emission light quantities Ed and Ee.

The light source control portion 31 generates and outputs the light source drive signal for making the narrowband light source 32p emit the light by the emission light quantity Ed, making the narrowband light source 32q emit the light by the emission light quantity Ee, and making the narrowband light source 32r emit the light by the emission light quantity Ef, when the sharpness "strong" is selected in the sharpness emphasizing switch, according to the emission light quantity ratio control signal outputted from the control portion 47.

Figure 44:
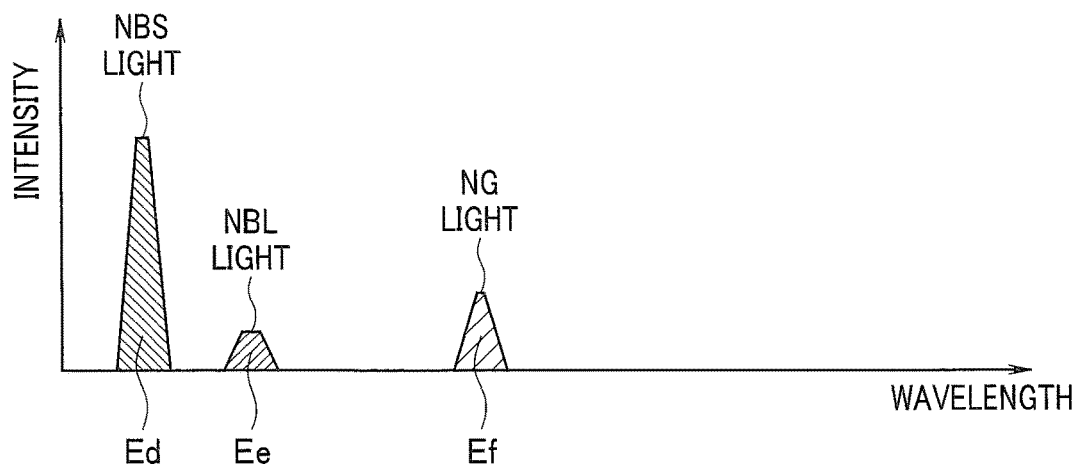
FIG. 44 is a diagram for describing one example of the illumination light supplied from the light source device in the fourth embodiment.

Then, according to the operations of the control portion 47 and the light source control portion 31 as described above, in the illumination period PG of the illumination pattern IP4, for example, as illustrated in FIG. 44, the NBS light emitted by the emission light quantity Ed is supplied from the light source device 3C as the illumination light, the return light Lf according to the NBS light is emitted from the object illuminated by the illumination light, and the image data ILf obtained by picking up the image of the return light Lf is outputted from the A/D conversion portion 42 to the CB processing portion 43C.

In addition, according to the operations of the control portion 47 and the light source control portion 31 as described above, in the illumination period PH of the illumination pattern IP4, for example, as illustrated in FIG. 44, the NBL light emitted by the emission light quantity Ee is supplied from the light source device 3C as the illumination light, the return light Lg according to the NBL light is emitted from the object illuminated by the illumination light, and the image data ILg obtained by picking up the image of the return light Lg is outputted from the A/D conversion portion 42 to the CB processing portion 43C.

In addition, according to the operations of the control portion 47 and the light source control portion 31 as described above, in the illumination period PI of the illumination pattern IP4, for example, as illustrated in FIG. 44, the NG light emitted by the emission light quantity Ef is supplied from the light source device 3C as the illumination light, return light Lh according to the NG light is emitted from the object illuminated by the illumination light, and image data ILh obtained by picking up the image of the return light Lh is outputted from the A/D conversion portion 42 to the CB processing portion 43C.

Figure 45:
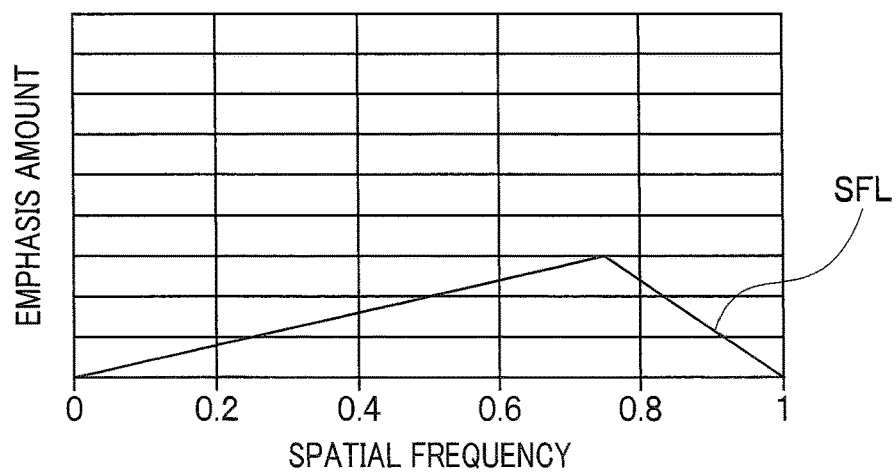
FIG. 45 is a diagram illustrating one example of the filter characteristic of the spatial filter used in the spatial filter processing in the fourth embodiment.

When detecting that the sharpness "strong" is selected in the sharpness emphasizing switch, for example, the control portion 47 reads a spatial filter SFL designed to have the filter characteristic as illustrated in FIG. 45 for example from the memory 47a, and performs the control for causing the spatial filter processing using the read spatial filter SFL to be performed to the sharpness emphasizing portion 44. Note that the filter characteristic in FIG. 45 is illustrated as the characteristic that the spatial frequency emphasized by the maximum emphasis amount exists in the higher band than the band of the spatial frequency of the spatial filter SFK and the emphasis amount at the spatial frequency around the maximum emphasis amount is equal to or larger than the emphasis amount of the spatial filter SFK.

The sharpness emphasizing portion 44 executes the spatial filter processing using the spatial filter SFL to each of the image data ILf, ILg and ILh outputted from the CB processing portion 43C when the sharpness "strong" is selected in the sharpness emphasizing switch according to the control of the control portion 47, and outputs the image data to which the spatial filter processing is executed to the gradation conversion portion 45.

The control portion 47 performs the control for making the image data ILf outputted from the gradation conversion portion 45 be allocated to the B channel of the display device 5, making the image data ILg outputted from the gradation conversion portion 45 be allocated to the G channel of the display device 5, and making the image data ILh outputted from the gradation conversion portion 45 be allocated to the R channel of the display device 5 to the display control portion 46.

Then, according to the operation of the control portion 47 or the like as described above, when the sharpness "strong" is selected in the sharpness emphasizing switch, the observation image in which the capillary and the mucosal structure existing in the surface layer of the biological tissue are emphasized compared to the capillary and the mucosal structure at the sharpness "middle" is displayed at the display device 5. In other words, according to the operation of the control portion 47 or the like as described above, when the sharpness "strong" is selected in the sharpness emphasizing switch, the observation image in which the visibility of the capillary and the mucosal structure existing in the surface layer of the biological tissue of the observation target is improved more than the visibility at the sharpness "middle" is displayed at the display device 5.

According to the configuration and operations or the like of the present embodiment as described above, the generation frequency of the artifact such as the color noise due to the spatial filter processing for highlighting the structure such as the blood vessel included in the biological tissue can be suppressed to the low frequency, that is, the decline of the image quality which occurs according to the emphasis degree when highlighting the structure can be suppressed.

In addition, according to the present embodiment, the emission light quantities in the respective light sources of the light source unit 32C are adjusted according to the sharpness selected in the sharpness emphasizing switch so that the fluctuation of the brightness and/or the color tone of the observation image which can occur accompanying the changeover of the sharpness in the sharpness emphasizing switch can be suppressed as much as possible.

Note that the present invention is not limited to the respective embodiments and modifications described above and can be variously changed and modified without deviating from a subject matter of the invention.

What is claimed is:

1. An observation system comprising:
   a light source portion configured to generate:
   light of a first wavelength band, which is green light, scattered or absorbed in a layer of a predetermined depth in biological tissue,
   light of a second wavelength band, which is green light, having a center wavelength on a long-wavelength side with respect to the light of the first wavelength band,
   light of a third wavelength band, which is blue light, scattered or absorbed in a layer shallower than the predetermined depth in the biological tissue, and
   light of a fourth wavelength band, which is blue light, having a center wavelength on a short-wavelength side with respect to the light of the third wavelength band, as illumination light for illuminating the biological tissue;
   an emphasizing processing portion configured to perform emphasizing processing for highlighting a structure positioned in the layer of the predetermined depth in the biological tissue, in an image obtained by picking up an image of return light from the biological tissue illuminated by the illumination light;
   a selecting portion configured to select an emphasis amount of the emphasizing processing performed in the emphasizing processing portion from:
   a first emphasis amount,
   a second emphasis amount larger than the first emphasis amount, and
   a third emphasis amount larger than the second emphasis amount; and
   a control portion configured to:
   when the first emphasis amount is selected by the selecting portion, set a ratio of a light quantity of the light of the second wavelength band to a light quantity of the light of the first wavelength band to a first ratio, and set a ratio of a light quantity of the light of the fourth wavelength band to a light quantity of the light of the third wavelength band to a second ratio,
   when the second emphasis amount is selected by the selecting portion, set a ratio of the light quantity of the light of the fourth wavelength band to the light quantity of the light of the third wavelength band to the second ratio, and set a ratio of the light quantity of the light of the second wavelength band to the light quantity of the light of the first wavelength band to a third ratio larger than the first ratio, and
   when the third emphasis amount is selected by the selecting portion, set a ratio of the light quantity of the light of the second wavelength band to the light quantity of the light of the first wavelength band to the third ratio, and set a ratio of the light quantity of the light of the fourth wavelength band to the light quantity of the light of the third wavelength band to a fourth ratio larger than the second ratio.

2. The observation system according to claim 1, wherein the control portion equalizes an added value of the light quantity of the light of the first wavelength band and the light quantity of the light of the second wavelength band before and after changing the ratio of the light quantity of the light of the second wavelength band to the light quantity of the light of the first wavelength band.

3. The observation system according to claim 1, wherein the control portion performs control for changing the ratio of the light quantity of the light of the second wavelength band to the light quantity of the light of the first wavelength band according to the emphasis amount selected by the selecting portion, and also performs control for changing a gradation conversion function used in gradation conversion processing corresponding to the emphasizing processing.

4. The observation system according to claim 1, further comprising a white balance processing portion configured to execute white balance processing to the image,
wherein the control portion changes a white balance coefficient applied in the white balance processing, based on a value of a light quantity ratio after the light quantity of the light of the second wavelength band to the light quantity of the light of the first wavelength band is changed.

5. An observation system comprising:
a light source portion configured to generate:
light of a first wavelength band, which is red light, scattered or absorbed in a layer of a predetermined depth in biological tissue,
light of a second wavelength band, which is red light, having a center wavelength on a short-wavelength side with respect to the light of the first wavelength band,
light of a third wavelength band, which is green light, scattered or absorbed in a layer shallower than the predetermined depth in the biological tissue, and
light of a fourth wavelength band, which is green light, having a center wavelength on a long-wavelength side with respect to the light of the third wavelength band, as illumination light for illuminating the biological tissue;
an emphasizing processing portion configured to perform emphasizing processing for highlighting a structure positioned in the layer of the predetermined depth in the biological tissue, in an image obtained by picking up an image of return light from the biological tissue illuminated by the illumination light;
a selecting portion configured to select an emphasis amount of the emphasizing processing performed in the emphasizing processing portion from:
a first emphasis amount,
a second emphasis amount larger than the first emphasis amount, and
a third emphasis amount larger than the second emphasis amount; and
a control portion configured to:
when the first emphasis amount is selected by the selecting portion, set a ratio of a light quantity of the light of the second wavelength band to a light quantity of the light of the first wavelength band to a first ratio, and set a ratio of a light quantity of the light of the fourth wavelength band to a light quantity of the light of the third wavelength band to a second ratio,
when the second emphasis amount is selected by the selecting portion, set a ratio of the light quantity of the light of the fourth wavelength band to the light quantity of the light of the third wavelength band to the second ratio, and set a ratio of the light quantity of the light of the second wavelength band to the light quantity of the light of the first wavelength band to a third ratio larger than the first ratio, and
when the third emphasis amount is selected by the selecting portion, set a ratio of the light quantity of the light of the second wavelength band to the light quantity of the light of the first wavelength band to the third ratio, and set a ratio of the light quantity of the light of the fourth wavelength band to the light quantity of the light of the third wavelength band to a fourth ratio larger than the second ratio.

6. An observation system comprising:
a light source portion configured to generate:
light of a first wavelength band, which is red light, scattered or absorbed in a layer of a predetermined depth in biological tissue,
light of a second wavelength band, which is red light, having a center wavelength on a short-wavelength side with respect to the light of the first wavelength band,
light of a third wavelength band, which is blue light, scattered or absorbed in a layer shallower than the predetermined depth in the biological tissue, and
light of a fourth wavelength band, which is blue light, having a center wavelength on a short-wavelength side with respect to the light of the third wavelength band, as illumination light for illuminating the biological tissue;
an emphasizing processing portion configured to perform emphasizing processing for highlighting a structure positioned in the layer of the predetermined depth in the biological tissue, in an image obtained by picking up an image of return light from the biological tissue illuminated by the illumination light;
a selecting portion configured to be capable of selecting an emphasis amount of the emphasizing processing performed in the emphasizing processing portion from:
a first emphasis amount,
a second emphasis amount larger than the first emphasis amount, and
a third emphasis amount larger than the second emphasis amount; and
a control portion configured to:
when the first emphasis amount is selected by the selecting portion, set a ratio of a light quantity of the light of the second wavelength band to a light quantity of the light of the first wavelength band to a first ratio, and set a ratio of a light quantity of the light of the fourth wavelength band to a light quantity of the light of the third wavelength band to a second ratio,
when the second emphasis amount is selected by the selecting portion, set a ratio of the light quantity of the light of the fourth wavelength band to the light quantity of the light of the third wavelength band to the second ratio, and set a ratio of the light quantity of the light of the second wavelength band to the light quantity of the light of the first wavelength band to a third ratio larger than the first ratio, and
when the third emphasis amount is selected by the selecting portion, set a ratio of the light quantity of the light of the second wavelength band to the light quantity of the light of the first wavelength band to the third ratio, and set a ratio of the light quantity of the light of the fourth wavelength band to the light quantity of the light of the third wavelength band to a fourth ratio larger than the second ratio.

* * * * *